US008846636B2

(12) United States Patent
Guindon

(10) Patent No.: US 8,846,636 B2
(45) Date of Patent: Sep. 30, 2014

(54) NUCLEOSIDE ANALOGUES WITH QUATERNARY CARBON STEREOGENIC CENTERS AND METHODS OF USE

(75) Inventor: Yvan Guindon, Montreal (CA)

(73) Assignee: LCB Pharma Inc., Montreal, Quebec (CA)

( * ) Notice: Subject to any disclaimer, the term of this patent is extended or adjusted under 35 U.S.C. 154(b) by 671 days.

(21) Appl. No.: 12/933,291

(22) PCT Filed: Mar. 18, 2009

(86) PCT No.: PCT/IB2009/005470
§ 371 (c)(1),
(2), (4) Date: Nov. 30, 2010

(87) PCT Pub. No.: WO2009/115927
PCT Pub. Date: Sep. 24, 2009

(65) Prior Publication Data
US 2011/0092451 A1    Apr. 21, 2011

Related U.S. Application Data

(60) Provisional application No. 61/037,483, filed on Mar. 18, 2008.

(51) Int. Cl.
*A61K 31/70* (2006.01)
*A01N 43/04* (2006.01)
*C07H 19/00* (2006.01)
*C07H 19/167* (2006.01)
*C07H 19/173* (2006.01)
*C07F 9/02* (2006.01)
*C07D 473/00* (2006.01)
*C07H 19/20* (2006.01)
*C07H 19/16* (2006.01)
*C07H 19/06* (2006.01)
*C07H 19/23* (2006.01)
*C07H 19/10* (2006.01)

(52) U.S. Cl.
CPC ............... *C07H 19/06* (2013.01); *C07H 19/20* (2013.01); *C07H 19/16* (2013.01); *C07H 19/23* (2013.01); *C07H 19/10* (2013.01)
USPC .............. 514/45; 514/46; 514/47; 514/48; 514/49; 514/50; 514/51; 536/27.6; 536/27.81; 536/28.5; 536/28.53; 544/243; 544/264

(58) Field of Classification Search
None
See application file for complete search history.

(56) References Cited

U.S. PATENT DOCUMENTS 3,558,595 A * 1/1971 Jones et al. ............... 536/17.1
8,361,988 B2 * 1/2013 Guindon ...................... 514/45

FOREIGN PATENT DOCUMENTS

| WO | WO 01/90121 | 11/2001 |
| WO | WO 01/92282 | 12/2001 |
| WO | WO 02/32920 | 4/2002 |
| WO | WO 2004/096286 | 11/2004 |
| WO | WO 2008/087558 | 7/2008 |

OTHER PUBLICATIONS

Cardinal-David, B., et al., "Synthesis of Tertiary and Quaternary Stereogenic Centers: A Diastereoselective Tandem Reaction Sequence Combining Mukaiyama and Free Radical-Based Alylation", J. Org. Chem., vol. 70, pp. 776-784 (2005).
Cardinal-David, B., et al., "Phenylseleneothers as Precursors of Acyclic Free Radicals. Creating Tertiary and Quaternary Centers Using Free Radical-Based Intermediates", Curr. Org. Chem., vol. 10, (2006), pp. 1939-1961.
Guindon, Y., et al., "Synthesis of N-Glycosides. An Alternative Approach Based on Diastereoselective Base Coupling and $S_N2$ Cyclization", Org. Lett., vol. 4, No. 2, pp. 241-244, (2002).
Hong, J., et al, "Synthesis of novel 3'-C-methyl-4'-thio apionucleosides via highly enantioselective elaboration of quaternary carbon by [3,3]-sigmatropic rearrangement", Tet. Lett., vol. 40, pp. 231-234 (1999).
Hong, J., et al., "Synthesis of novel 3'-C-methyl-apionucleosides: an asymmetric construction of a quaternary carbon by Claisen rearrangement", Carbohydr. Res., vol. 328, pp. 37-48 (2000).
Kim, A., et al., "Racemic synthesis and antiviral evaluation of 4'(alpha)-hydroxymethyl and 6'(alpha)-methyl substituted apiosyl nucleosides", Nucleosides, Nucleotides Nucleic Acids, vol. 26, pp. 291-302 (2007).
Oh, C. H., et al., "Simple synthesis and anti-HIV activity of novel 3'-vinyl branched apiosyl pyrimidine nucleosides", Nucleosides Nucleotides Nucleic Acids, vol. 25, pp. 871-878 (2006).
Zhong, J. -H., et al., "Photochemistry on Soluble Polymer Supports: Synthesis of Nucleotides", Orig. Lett., vol. 4, No. 25, pp. 4415-4417 (2002).
PCT/IB2009 005470, European Search Report, Dec. 16, 2013.

* cited by examiner

*Primary Examiner* — Lawrence E Crane
(74) *Attorney, Agent, or Firm* — McDonnell Boehnen Hulbert & Berghoff LLP

(57) ABSTRACT

The disclosure provides nucleotide analogues that comprise tetrahydrofuranyl or tetrahydrothienyl moieties with quaternary centers at the 3' position, the pharmaceutical formulations comprising the analogues, and methods of using the analogues and formulations for treating, preventing, and/or inhibiting diseases or conditions associated with cancers and viruses.

14 Claims, No Drawings

NUCLEOSIDE ANALOGUES WITH QUATERNARY CARBON STEREOGENIC CENTERS AND METHODS OF USE

CROSS-REFERENCE TO RELATED APPLICATIONS

This application is a National Entry Application of PCT application no PCT/IB2009/005470 filed on Mar. 18, 2009 and published in English under PCT Article 21(2), which itself claims priority on U.S. provisional application Ser. No. 61/037,483, filed on Mar. 18, 2008. All documents above are incorporated herein in their entirety by reference.

FIELD OF THE INVENTION

This invention relates to the field of nucleotide analogues useful as antiviral and antitumor agents. In particular, the invention relates to compounds comprising tetrahydrofuranyl or tetrahydrothienyl moeities with quaternary carbon centers at the 3' position.

BACKGROUND OF THE INVENTION

Nucleotides are one of the most important cellular metabolites. Nucleotides are found primarily as the monomeric units comprising the major nucleic acids of the cell, RNA and DNA. However, they also are required for numerous other important functions within the cell. These functions include energy stores in phosphate transfer reactions (ATP); as coenzymes (for example, NAD+, NADP+, FAD and coenzyme A); mediators cellular processes (such as cyclic-AMP); allosteric effector on enzyme activity; and activated intermediates (S-adenosylmethionine).

Nucleotide analogues are chemically synthesized and used as therapeutics. Nucleotide analogues can be utilized to inhibit specific enzymatic activities, for example, as antitumor agents that interfere with the synthesis of DNA and thereby preferentially kill rapidly dividing cells such as tumor cells. Some commonly used nucleotide analogues in chemotherapy are 6-mercaptopurine, 5-fluorouracil, 5-iodo-2'-deoxyuridine and 6-thioguanine. Synthesis of DNA is disrupted because the nucleotide analogues prevent correct Watson-Crick base-pairing.

Nucleotide analogues are also used as antiviral agents. Example are abacavir, didanosine, emtricitabine, lamivudine, stavudine, tenofovir, zalcitabine, and zidovudine. For example, AZT (azidothymidine) and ddI (dideoxyinosine) are use to inhibit replication of HIV. Purine-containing nucleotide analogues are used to treat gout, for example, allopurinol that inhibits the activity of xanthine oxidase, an enzyme involved in de novo purine biosynthesis. Additionally, nucleotide analogues are used to suppress the immune system after organ transplantation and reduce transplant rejection.

Nucleotide analogues, in their phosphorylated form, are also included in small polymeric sequences used as antisense RNA, siRNA (small interfering RNA) or miRNA (micro RNA) to control the transcription and translation of genes related to cancer or viral infections.

Antisense mRNA is an mRNA transcript that is complementary to endogenous mRNA, that is, the noncoding strand complement to the coding strand. A strategy to block expression of a gene of interest is to introduce a transgene coding for antisense mRNA. Analogous molecules with modified backbones using nucleotide analogues have been designed which change various characteristics of antisense RNA, such as instability to degradative enzymes or ability to form stable double strands with the complementary sense RNA. Some alternative antisense molecules include phosphorothioate, morpholino, PNA (peptide nucleic acid), LNA (locked nucleic acid), and 2'-O alkyl oligos.

Small interfering RNA (siRNA), sometimes known as short interfering RNA or silencing RNA, are a class of 20-25 nucleotide-long RNA molecules that play a variety of roles. SiRNAs have a well defined structure that consist of a short, usually 21-nt, double-strand of RNA with 2-nt 3' overhangs on either end. Most notably, siRNA is involved in the RNA interference pathway (RNAi) where the siRNA interferes with the expression of specific genes. In addition, siRNAs also act in RNAi-related pathways, e.g. as an antiviral mechanism or in shaping the chromatin structure of a genome; the complexity of these pathways is only now being elucidated. SiRNAs were first discovered as part of post-transcriptional gene silencing (PTGS) in plants (see U.S. Pat. No. 7,056,704 and Hamilton and Baulcombe, Science, 1999, 286, 950-952). Synthetic siRNAs have also been shown to induce RNAi in mammalian cells (see Elbashir et al., Nature, 2001, 411, 494-498) with led to interest in harnessing RNAi for biomedical research and drug development.

Micro RNA (miRNA) are small ribonucleic acid chains, about 22 nt long that are implicated in cell growth and apoptosis, embryonic development, neuronal plasticity and remodeling, and even insulin secretion. An overabundance of miRNA has been reported in cases of Fragile X Mental Retardation while some cancers have been reported to have down-regulated miRNA genes.

Antisense RNA, siRNA and miRNA are being experimentally applied as antisense therapy or to create knockout organisms to study gene function. For example, the suppression of protein synthesis by introducing antisense RNA, siRNA or miRNA into a cell may be useful to inhibit a number of infections or diseases in both plants and animals. A gene encoding the antisense RNA, siRNA or miRNA can be introduced fairly easily into organisms by using a plasmid vector or using a gene gun that shoots microscopic tungsten pellets coated with the gene into cells. Once the antisense RNA, siRNA or miRNA is introduced, it will specifically inhibit the synthesis of the target protein by binding to mRNA. Antisense RNA, siRNA or miRNA can be use in therapy, for example, for treating B-cell lymphomas and leukemias, treating HIV-1, cytomegalovirus, herpesvirus, asthma and cancers. Antisense RNA, siRNA or miRNA can also be used for commercial food production, for example, disease control and produce preservation. For example, siRNAs may be used as important tools for transcriptional modulating in silencing of mammalian genes by guiding DNA methylation.

Thus, an object of this invention is the identification of novel nucleotide analogues that can be used as antiviral or antitumor agents to inhibit diseases and conditions associated viruses and cancers.

SUMMARY OF THE INVENTION

The invention comprises compounds and pharmaceutical compositions of the compounds useful as antiviral or antitumor agents. The compounds of the invention comprise nucleotide analogues that comprise tetrahydrofuranyl or tetrahydrothienyl moeities with quaternary carbon centers at the 3' position.

The first aspect of the invention provides compounds that are antiviral or antitumor agents. The compounds are exemplified by formulae I-XVI.

In a second aspect, the invention comprises pharmaceutical compositions comprising a pharmaceutically acceptable carrier, excipient, or diluent and compounds according to formula I-XVI or pharmaceutically acceptable salts thereof.

In a third aspect, the invention comprises methods for inhibiting a virus or tumor comprising contacting a cell in which inhibition is desired with a compound according to formula I-XVI or a pharmaceutical composition according to the second aspect of the invention.

In a fourth aspect, the invention comprises methods for inhibiting a virus or tumor in a patient comprising administering to the patient a pharmaceutical composition according to formula I-XVI.

In a fifth aspect, the invention comprises methods for treating a disease or condition in a patient, wherein the disease or condition involves a virus or is a tumor, comprising administering to the patient a pharmaceutical composition according to the second aspect of the invention. The disease or condition may be selected from ovarian cancer, cervical cancer, breast cancer, skin cancer, brain cancer, colorectal cancer, lung cancer, bone cancer, glioblastomas, influenza, or diseases caused by HPV, HIV, or HCV.

The foregoing only summarizes certain aspects of the invention and is not intended to be limiting in nature. These aspects and other aspects and embodiments are described more fully below. All references any sort referred to in this specification are hereby incorporated by reference in their entirety. In the event of a discrepancy between the express disclosure of this specification and the references incorporated by reference, the express disclosure of this specification shall control.

DETAILED DESCRIPTION OF THE INVENTION

The first aspect of the invention provides compounds of the formula

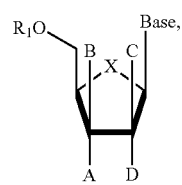

I

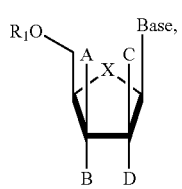

II

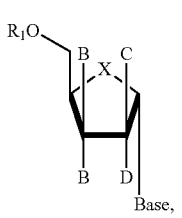

III

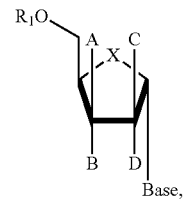

IV

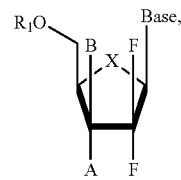

I-F

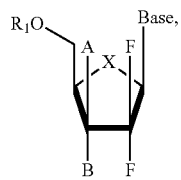

II-F

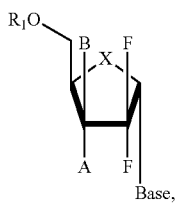

III-F

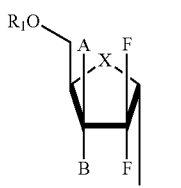

IV-F

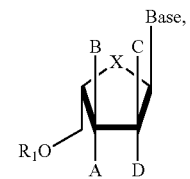

V

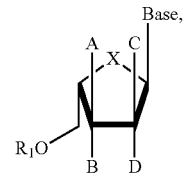

VI

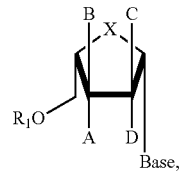

VII

VIII
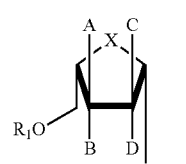
V-F
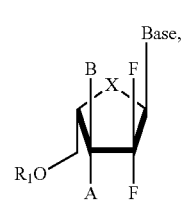
VI-F
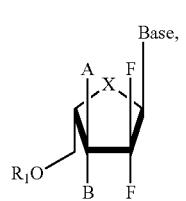
VII-F
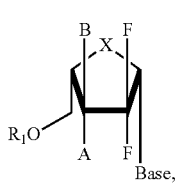
VIII-F
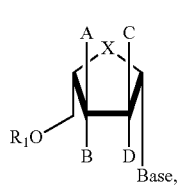
IX
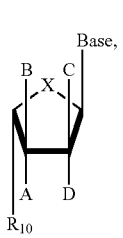
X
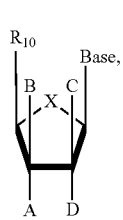
XI
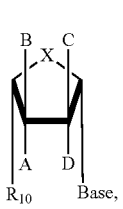
XII
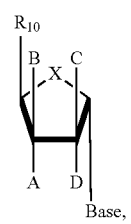
IX-F
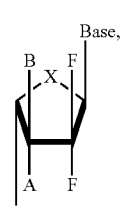
X-F
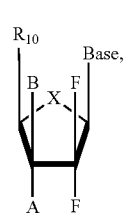
XI-F
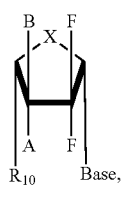
XII-F
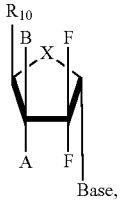
XIII
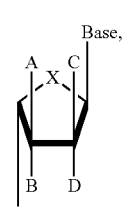
XIV
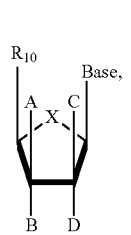

XV

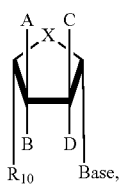

XVI

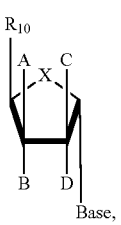

XIII-F

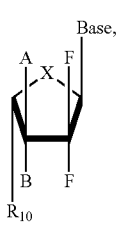

XIV-F

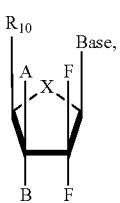

XV-F

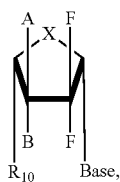

XVI-F

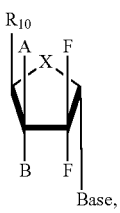

XVII

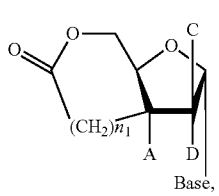

XVIII

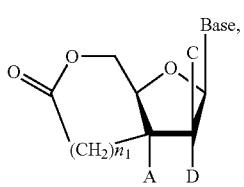

XIX

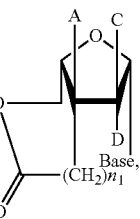

XX

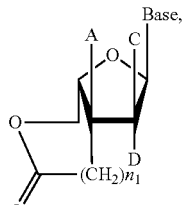

XVII-F

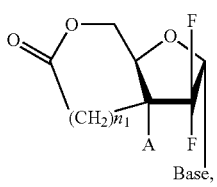

XVIII-F

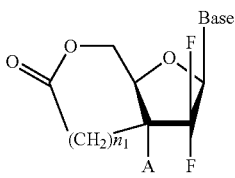

XIX-F

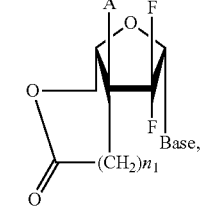

XX-F

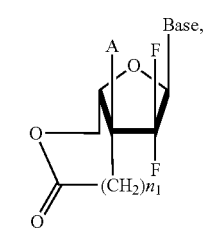

or pharmaceutically acceptable salts thereof, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —C(O)—$NR_4R_{4a}$, —C(O)$OR_2$, —$(CH_2)n_1C(O)OR_2$, —C(O)—$R_3$, or —$(CH_2)_nM$;

M is —$OR_1$, halo, mono- to per-halo $C_1$-$C_6$ alkyl, —$SR_1$, aryl, —$CO_2R_2$, —$COR_3$, heterocyclyl, heteroaryl, —NH(CO)$R_5$, —$NR_6R_{6a}$, —$CONR_4R_{4a}$, —$NHSO_2R_7$, —CO—$CH_2OH$, —$SOR_8$, —$SO_2NR_5R_{5a}$, —O(CO)$R_3$, —$N_3$, or $C_2$-$C_6$ alkynyl, wherein each of the alkyl, heterocyclyl, aryl, and heteroaryl is optionally substituted with one or more groups selected from $C_1$-$C_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

n is 1 to 3;

n$_1$ is 0 to 3

R$_1$ is —H, —CH$_2$—P(O)(OH)$_2$, —P(O)(OH)$_2$, —P(O)(OR$_2$)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

R$_2$ is —H, aryl, —C$_1$-C$_6$ alkylaryl, or C$_1$-C$_6$ alkyl;

R$_3$ is —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_2$, —C$_1$-C$_6$ alkyl-C(O)OR$_2$, C$_1$-C$_6$ alkoxy, and mono- to per-halo C$_1$-C$_6$ alkyl;

R$_4$ and R$_{4a}$ are independently —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl; or R$_4$ and R$_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

R$_5$ and R$_{5a}$ are independently —H, aryl, C$_1$-C$_6$ alkylaryl, C$_1$-C$_6$ alkyl, or C$_1$-C$_6$ alkoxy;

R$_6$ and R$_{6a}$ are independently —H, aryl, C$_1$-C$_6$ alkylaryl, or C$_1$-C$_6$ alkyl;

R$_7$ is C$_1$-C$_6$ alkyl, aryl, C$_1$-C$_6$ alkylaryl, or mono- to per-halo C$_1$-C$_6$ alkyl;

R$_8$ is C$_1$-C$_6$ alkyl, aryl, C$_1$-C$_6$ alkylaryl, or mono- to per-halo C$_1$-C$_6$ alkyl;

R$_9$ is H or C$_1$-C$_6$ alkyl

C and D are independently —H, halo, azide, —OR$_2$, CN, CF$_3$, (CH$_2$)nCO$_2$R$_9$, C(O)NR$_4$R$_{4a}$, or —CONR$_6$R$_{6a}$;

X is O or S;

R$_{10}$ is —C(O)OR$_3$, —CH$_2$—C(O)OR$_3$, —CONH$_2$, —CONHR$_6$, —CONHNH$_2$, —CONHNHR$_6$, —CONR$_4$R$_{4a}$, —CONR$_6$R$_{6a}$, —CH$_2$—P(O)(OH)$_2$, —P(O)(OH)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

and Base is a purine derivative or a pyrimidine derivative.

Embodiment A provides compounds according to formula I to XX, and I-F to XX-F, wherein at least one of C and D is —H.

Embodiment B provides compounds according to formula I-VIII, wherein one of C and D is —H and the other is fluoro, azide, —OR$_2$ or —NR$_4$R$_{4a}$.

Embodiment C provides compounds according to formula I to XX, and I-F to XX-F, wherein A and B are independently C$_1$-C$_6$ alkyl, C$_2$-C$_6$ alkenyl, C$_2$-C$_6$ alkynyl, mono- to per-halo C$_1$-C$_6$ alkyl, —CONH$_2$, —CONR$_6$R$_{6a}$, —CONHNH$_2$, —CONHNHR$_6$, —C(O)—NR$_4$R$_{4a}$, —C(O)OR$_2$, —(CH$_2$)n$_1$C(O)OR$_2$, —C(O)—R$_3$, or —(CH$_2$)$_n$M;

M is —OR$_1$, halo, mono- to per-halo C$_1$-C$_6$ alkyl, —SR$_1$, aryl, —CO$_2$R$_2$, —COR$_3$, heterocyclyl, heteroaryl, —NH(CO)R$_5$, —NR$_6$R$_{6a}$, —CONR$_4$R$_{4a}$, —NHSO$_2$R$_7$, —CO—CH$_2$OH, —SOR$_8$, —SO$_2$NR$_5$R$_{5a}$, —O(CO)R$_3$, —N$_3$, or C$_2$-C$_6$ alkynyl, wherein each of the alkyl, heterocyclyl, aryl and heteroaryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

n is 1 to 3;

n$_1$ is 0 to 3

R$_1$ is —H, —CH$_2$—P(O)(OH)$_2$, —P(O)(OH)$_2$, —P(O)(OR$_2$)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

R$_2$ is —H, aryl, —C$_1$-C$_6$ alkylaryl, or C$_1$-C$_6$ alkyl;

R$_3$ is —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_2$, —C$_1$-C$_6$ alkyl-C(O)OR$_2$, C$_1$-C$_6$ alkoxy, and mono- to per-halo C$_1$-C$_6$ alkyl;

R$_4$ and R$_{4a}$ are independently —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl; or R$_4$ and R$_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

R$_5$ and R$_{5a}$ are independently —H, aryl, C$_1$-C$_6$ alkylaryl, C$_1$-C$_6$ alkyl, or C$_1$-C$_6$ alkoxy;

R$_6$ and R$_{6a}$ are independently —H, aryl, C$_1$-C$_6$ alkylaryl, or C$_1$-C$_6$ alkyl;

R$_7$ is C$_1$-C$_6$ alkyl, aryl, C$_1$-C$_6$ alkylaryl, or mono- to per-halo C$_1$-C$_6$ alkyl;

R$_8$ is C$_1$-C$_6$ alkyl, aryl, C$_1$-C$_6$ alkylaryl, or mono- to per-halo C$_1$-C$_6$ alkyl;

R$_9$ is H or C$_1$-C$_6$ alkyl

C and D are independently —H, halo, azide, —OR$_2$, —CN, —CF$_3$, —(CH$_2$)nCO$_2$R$_9$, —C(O)NR$_4$R$_{4a}$, or —CONR$_6$R$_{6a}$ X is O or S; and R$_{10}$ is —C(O)OR$_3$, —CH$_2$—C(O)OR$_3$, —CONH$_2$, —CONHR$_6$, —CONHNH$_2$, —CONHNHR$_6$, —CONR$_4$R$_{4a}$, —CONR$_6$R$_{6a}$, —CH$_2$—P(O)(OH)$_2$, —P(O)(OH)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl; and
Base is selected from
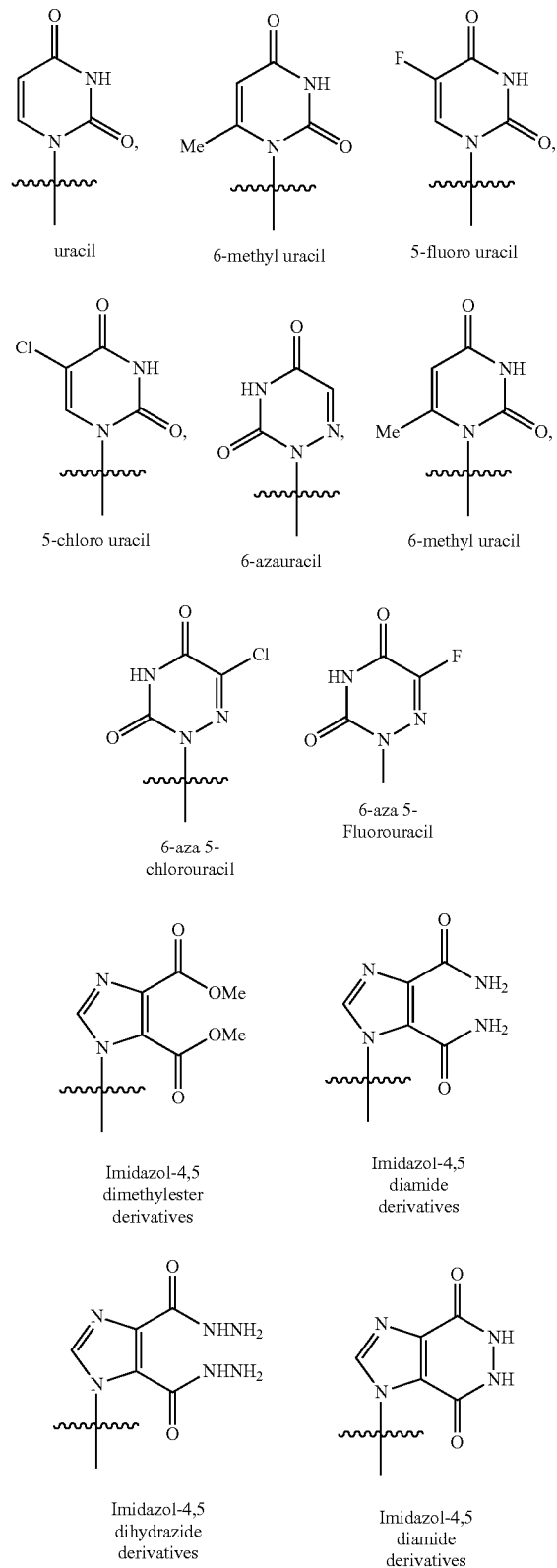
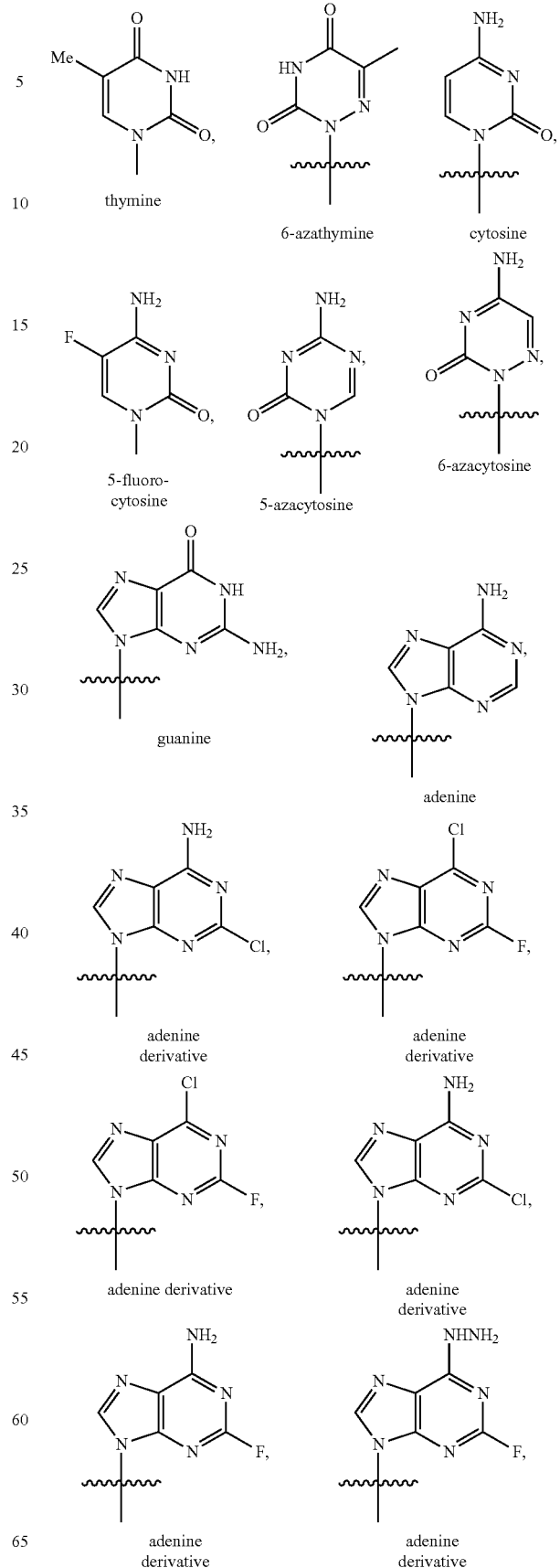

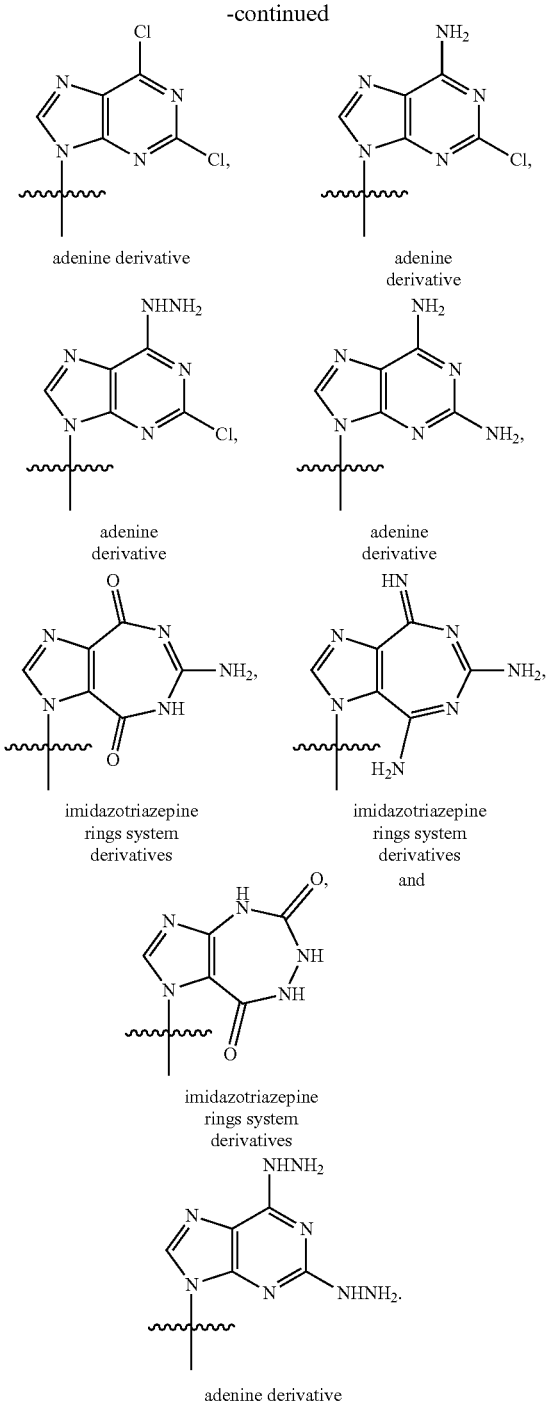

Embodiment D provides compounds according to Embodiment C, wherein A and B are independently —CH₃, —CH(CH₃)₂, —CF₃, —(CH₂)ₙ—CF₃, —(CH₂)ₙ-tetrazole, —(CH₂)ₙ-phenyl wherein the phenyl is optionally substituted with one or more groups selected from $C_1$-$C_3$ alkyl, —$C_1$-$C_3$ alkyl-C(O)OR₃, $C_1$-$C_3$ alkoxy, and mono- to per-halo $C_1$-$C_3$ alkyl.

Embodiment E provides compounds according to Embodiment C, wherein R₁ is —CF₃, —CH₂-phenyl, phenyl optionally substituted with halo, —CN, —CF₃, —C(O)OR₃, —CH₂—COOR₃, $C_1$-$C_3$ alkoxy, $C_1$-$C_4$ perfluoroalkyl, or $C_1$-$C_3$ alkyl.

Embodiment F provides compounds according to Embodiment C, wherein R₂ is phenyl or —CH₂-phenyl.

Embodiment G provides compounds according to Embodiment C, wherein R₃ is —CF₃, phenyl optionally substituted with halo, —CN, —CF₃, —C(O)OR₃, —CH₂—COOR₃, $C_1$-$C_3$ alkoxy, $C_1$-$C_4$ perfluoroalkyl, or $C_1$-$C_3$ alkyl.

Embodiment H provides compounds according to Embodiment C, wherein R₄ and R₄ₐ together with the nitrogen to which they are attached form -(AA)₁₋₄.

Embodiment I provides compounds according to Embodiment H, wherein R₄ and R₄ₐ together with the nitrogen to which they are attached form -(AA)₃.

Embodiment J provides compounds according to Embodiment I, wherein R₄ and R₄ₐ together with the nitrogen to which they are attached form -Arg-Arg-Arg.

Embodiment K provides compounds according to Embodiment C, wherein R₅ and R₅ₐ are independently —CH₂-phenyl or phenyl.

Embodiment L provides compounds according to Embodiment C, wherein R₆ and R₆ₐ are —CH₂-phenyl or phenyl.

Embodiment M provides compounds according to Embodiment C, wherein R₇ is 4-methylphenyl, phenyl or —CF₃

Embodiment N provides compounds according to Embodiment C, wherein Base is selected from

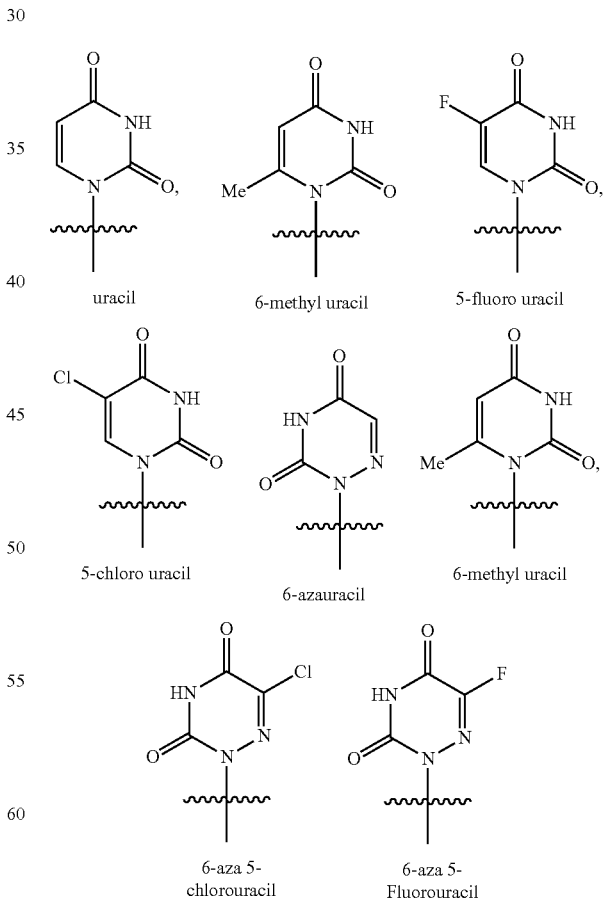

Embodiment O provides compounds according to Embodiment C, wherein Base is selected from

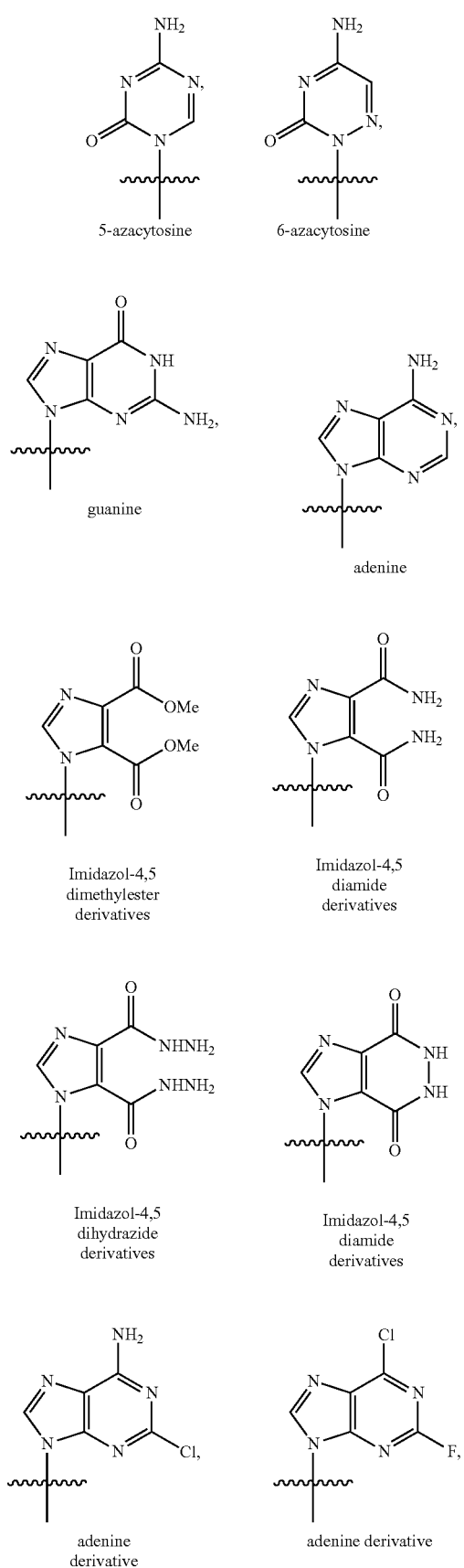
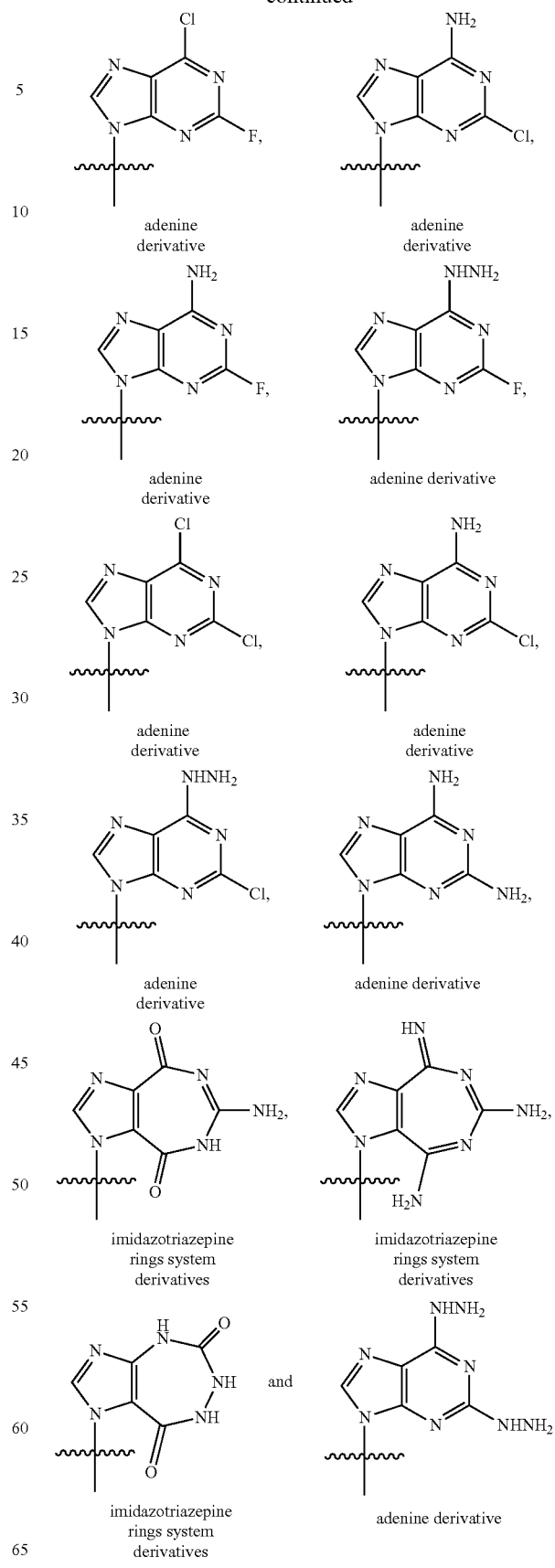

Embodiment P provides compounds having the formula

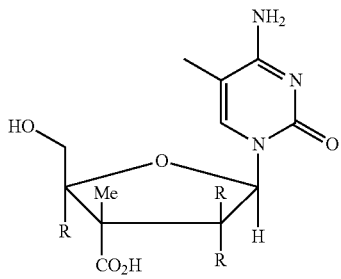
IX

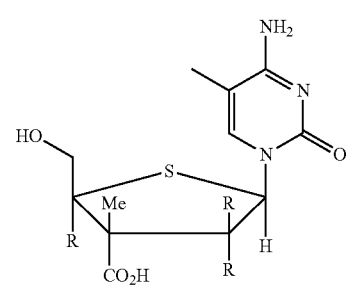
X or pharmaceutically acceptable salts thereof, wherein
R is —H or —OH.

Embodiment Q provides compounds having the formula

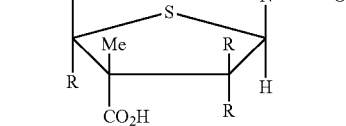
XI

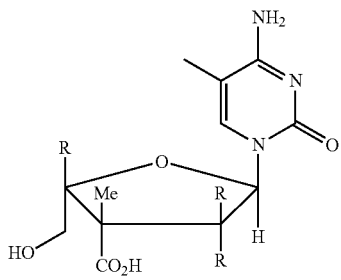
XII or pharmaceutically acceptable salts thereof, wherein
R is —H or —OH.

The invention also provides acyclic derivatives of the formula I to XX, and I-F to XX-F. Accordingly, Embodiment R provides compounds of the formula

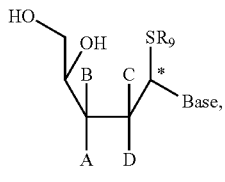
XXIII

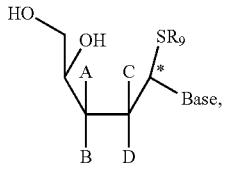
XXIV

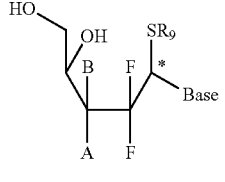
XIII-F

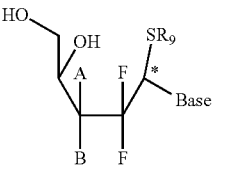
XXIV-F

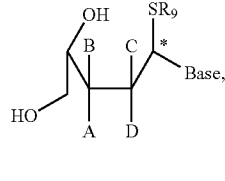
XXV

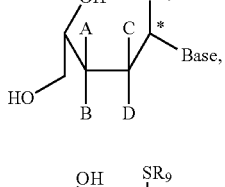
XXVI

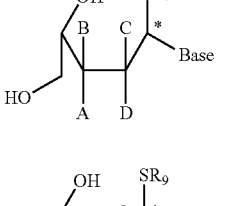
XXV-F

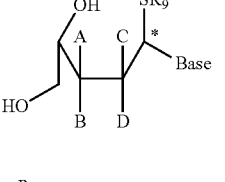
XXVI-F

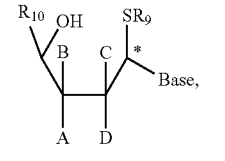
XXVIII

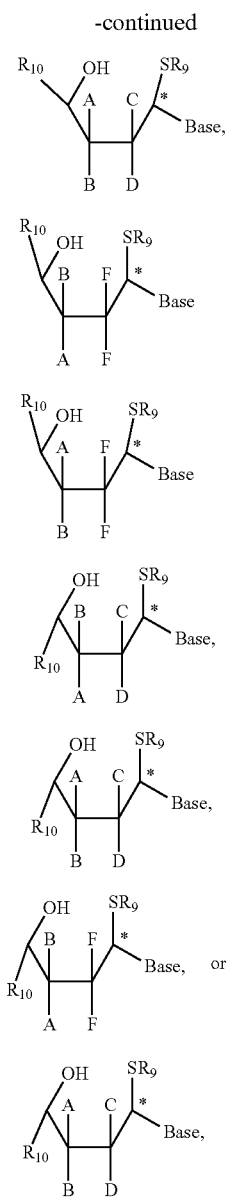

or pharmaceutically acceptable salts thereof, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —C(O)—$NR_4R_{4a}$, —C(O)$OR_2$, —$(CH_2)n_1C(O)OR_2$, —C(O)—$R_3$, or —$(CH_2)_nM$;

M is —$OR_1$, halo, mono- to per-halo $C_1$-$C_6$ alkyl, —$SR_1$, aryl, —$CO_2R_2$, —$COR_3$, heterocyclyl, heteroaryl, —NH(CO)$R_5$, —$NR_6R_{6a}$, —$CONR_4R_{4a}$, —$NHSO_2R_7$, —CO—$CH_2OH$, —$SOR_8$, —$SO_2NR_5R_{5a}$, —O(CO)$R_3$, —$N_3$, or $C_2$-$C_6$ alkynyl, wherein each of the alkyl, heterocyclyl, aryl and heteroaryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

n is 1 to 3;

$n_1$ is 0 to 3

$R_1$ is —H, —$CH_2$—P(O)(OH)$_2$, —P(O)(OH)$_2$, —P(O)(OR$_2$)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_2$ is —H, aryl, —$C_1$-$C_6$ alkylaryl, or $C_1$-$C_6$ alkyl;

$R_3$ is —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_2$, —$C_1$-$C_6$ alkyl-C(O)$OR_2$, $C_1$-$C_6$ alkoxy, and mono- to per-halo $C_1$-$C_6$ alkyl;

$R_4$ and $R_{4a}$ are independently —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl; or $R_4$ and $R_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

$R_5$ and $R_{5a}$ are independently —H, aryl, $C_1$-$C_6$ alkylaryl, $C_1$-$C_6$ alkyl, or $C_1$-$C_6$ alkoxy;

$R_6$ and $R_{6a}$ are independently —H, aryl, $C_1$-$C_6$ alkylaryl, or $C_1$-$C_6$ alkyl;

$R_7$ is $C_1$-$C_6$ alkyl, aryl, $C_1$-$C_6$ alkylaryl, or mono- to per-halo $C_1$-$C_6$ alkyl;

$R_8$ is $C_1$-$C_6$ alkyl, aryl, $C_1$-$C_6$ alkylaryl, or mono- to per-halo $C_1$-$C_6$ alkyl;

$R_9$ is H or $C_1$-$C_6$ alkyl;

C and D are independently —H, halo, azide, —$OR_2$, —CN, —$CF_3$, —$(CH_2)nCO_2R_9$, —C(O)$NR_4R_{4a}$, —$CONR_6R_{6a}$;

X is O or S; and $R_{10}$ is —C(O)$OR_3$, —$CH_2$—C(O)$OR_3$, —$CONH_2$, —$CONHR_6$, —$CONHNH_2$, —$CONHNHR_6$, —$CONR_4R_{4a}$, $CONR_6R_{6a}$, —$CH_2$—P(O)(OH)$_2$, —P(O)(OH)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

and Base is a purine or a pyrimidine derivative.

Embodiment S provides compounds according to Embodiment R, wherein at least one of C and D is —H.

Embodiment T provides compounds according to Embodiment R, wherein one of C and D is —H and the other is fluoro, azide, —$NR_4R_{4a}$, or $OR_2$.

Embodiment U provides compounds according to Embodiment T, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —C(O)—$NR_4R_{4a}$, —C(O)$OR_2$, —$(CH_2)n_1C(O)OR_2$, —C(O)—$R_3$, or —$(CH_2)_nM$;

M is —$OR_1$, halo, mono- to per-halo $C_1$-$C_6$ alkyl, —$SR_1$, aryl, —$CO_2R_2$, —$COR_3$, heterocyclyl, heteroaryl, —NH(CO)$R_5$, —$NR_6R_{6a}$, —$CONR_4R_{4a}$, —$NHSO_2R_7$, —CO—$CH_2OH$, —$SOR_8$, —$SO_2NR_5R_{5a}$, —O(CO)$R_3$, —$N_3$, or $C_2$-$C_6$ alkynyl, wherein each of the alkyl, heterocyclyl, aryl and heteroaryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

n is 1 to 3;

$n_1$ is 0 to 3

$R_1$ is —H, —CH$_2$—P(O)(OH)$_2$, —P(O)(OH)$_2$, —P(O)(OR$_2$)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

$R_2$ is —H, aryl, —C$_1$-C$_6$ alkylaryl, or C$_1$-C$_6$ alkyl;

$R_3$ is —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_2$, —C$_1$-C$_6$ alkyl-C(O)OR$_2$, C$_1$-C$_6$ alkoxy, and mono- to per-halo C$_1$-C$_6$ alkyl;

$R_4$ and $R_{4a}$ are independently —H, C$_1$-C$_6$ alkyl, —(CH$_2$)$_m$C(O)OR$_2$ wherein m is 0 to 4, mono- to per-halo C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl; or $R_4$ and $R_{4a}$ together with the nitrogen to which they are attached form -(AA)$_x$, wherein x is 1 to 5, and AA is a natural, non-natural, D- or L-amino acid, wherein -(AA)$_x$ comprises a terminal —COOR$_3$ group wherein the carbonyl is protected or unprotected;

$R_5$ and $R_{5a}$ are independently —H, aryl, C$_1$-C$_6$ alkylaryl, C$_1$-C$_6$ alkyl, or C$_1$-C$_6$ alkoxy;

$R_6$ and $R_{6a}$ are independently —H, aryl, C$_1$-C$_6$ alkylaryl, or C$_1$-C$_6$ alkyl;

$R_7$ is C$_1$-C$_6$ alkyl, aryl, C$_1$-C$_6$ alkylaryl, or mono- to per-halo C$_1$-C$_6$ alkyl;

$R_8$ is C$_1$-C$_6$ alkyl, aryl, C$_1$-C$_6$ alkylaryl, or mono- to per-halo C$_1$-C$_6$ alkyl;

$R_9$ is H or C$_1$-C$_6$ alkyl;

C and D are independently —H, halo, azide, —OR$_2$, —CN, —CF$_3$, —(CH$_2$)nCO$_2$R$_9$, —C(O)NR$_4$R$_{4a}$, or —CONR$_6$R$_{6a}$ X is O or S; and $R_{10}$ is —C(O)OR$_3$, —CH$_2$—C(O)OR$_3$, —CONH$_2$, —CONHR$_6$, —CONHNH$_2$, —CONHNHR$_6$, —CONR$_4$R$_{4a}$, —CONR$_6$R$_{6a}$, —CH$_2$—P(O)(OH)$_2$, —P(O)(OH)$_2$, C$_1$-C$_6$ alkyl, aryl, or —C$_1$-C$_6$ alkylaryl, wherein each of the alkyl and aryl is optionally substituted with one or more groups selected from C$_1$-C$_6$ alkyl, halo, —CN, —C(O)OR$_3$, —C$_1$-C$_6$ alkyl-C(O)OR$_3$, C$_1$-C$_6$ alkoxy, and mono- to per-halo C$_1$-C$_6$ alkyl;

and Base is selected from

-continued

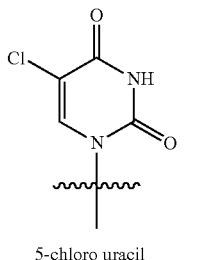
5-chloro uracil

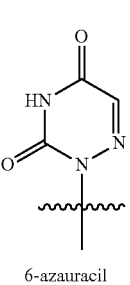
6-azauracil

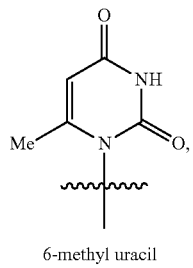
6-methyl uracil

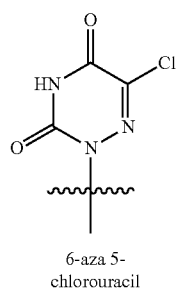
6-aza 5-chlorouracil

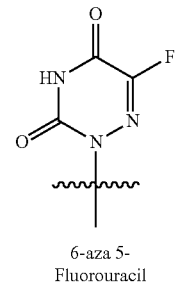
6-aza 5-Fluorouracil

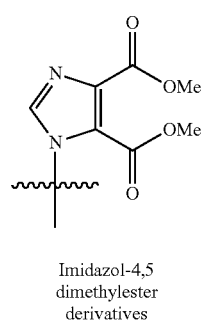
Imidazol-4,5 dimethylester derivatives

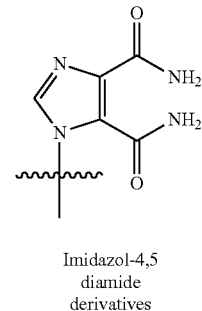
Imidazol-4,5 diamide derivatives

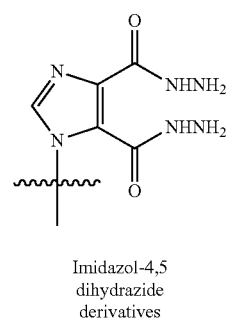
Imidazol-4,5 dihydrazide derivatives

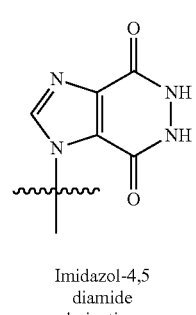
Imidazol-4,5 diamide derivatives

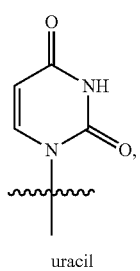
uracil

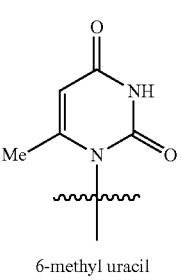
6-methyl uracil

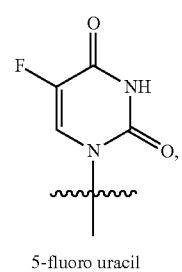
5-fluoro uracil

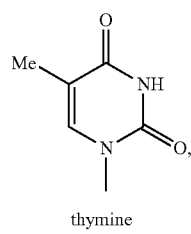
thymine

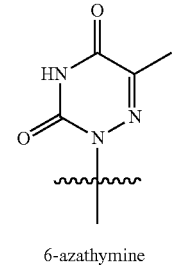
6-azathymine

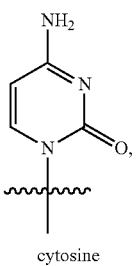
cytosine

-continued

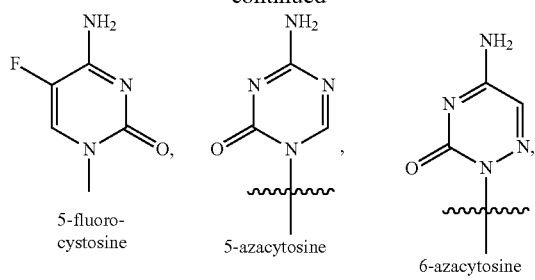

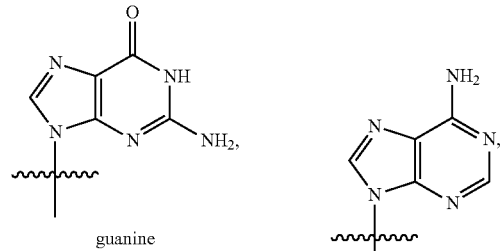

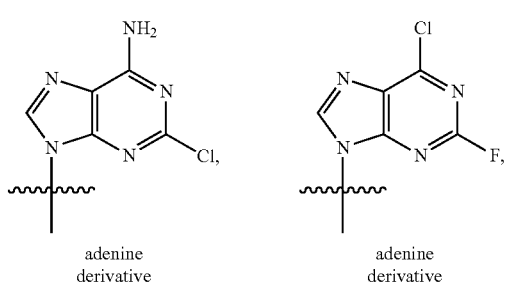

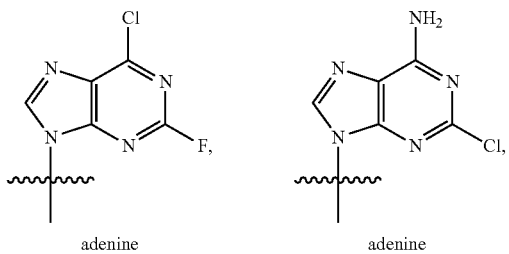

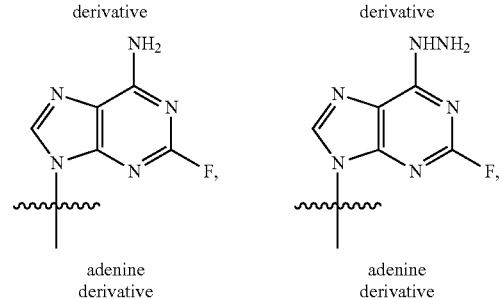

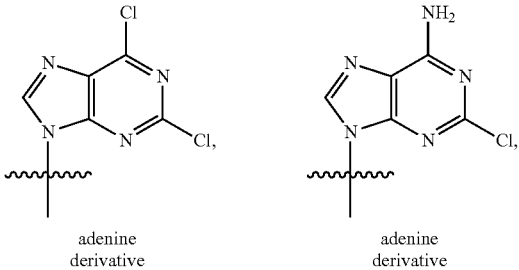

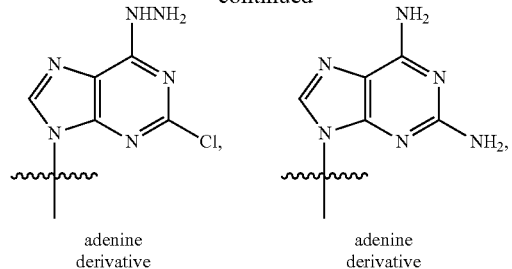

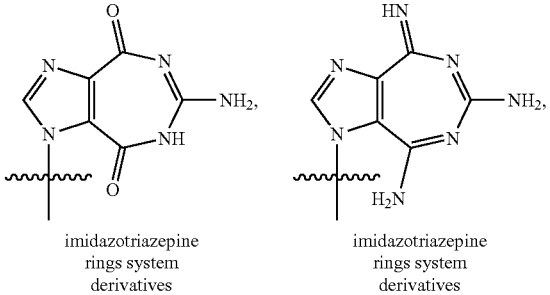

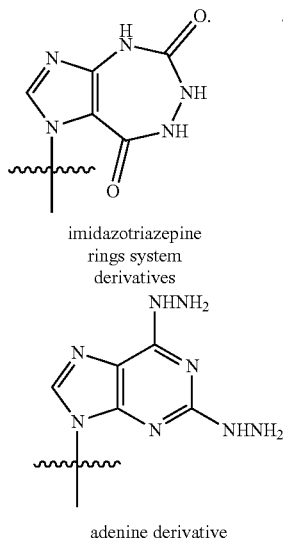

Embodiment V provides compounds according to Embodiment U, wherein A and B are independently —$CH_3$, —$CH(CH_3)_2$, —$CF_3$, —$(CH_2)_n$—$CF_3$, —$(CH_2)_n$-tetrazole, —$(CH_2)_n$-phenyl wherein the phenyl is optionally substituted with one or more groups selected from $C_1$-$C_3$ alkyl, —$C_1$-$C_3$ alkyl-C(O)OR$_3$, $C_1$-$C_3$ alkoxy, and mono- to per-halo $C_1$-$C_3$ alkyl.

Embodiment W provides compounds according to Embodiment U, wherein $R_1$ is —$CF_3$, —$CH_2$-phenyl, phenyl optionally substituted with halo, —CN, —$CF_3$, —C(O)OR$_3$, —$CH_2$—COOR$_3$, $C_1$-$C_3$ alkoxy, $C_1$-$C_4$ perfluoroalkyl, or $C_1$-$C_3$ alkyl.

Embodiment X provides compounds according to Embodiment U, wherein $R_2$ is phenyl or —$CH_2$-phenyl.

Embodiment Y provides compounds according to Embodiment U, wherein $R_3$ is —$CF_3$, phenyl optionally substituted with halo, —CN, —$CF_3$, —C(O)OR$_2$, —$CH_2$—COOR$_2$, $C_1$-$C_3$ alkoxy, $C_1$-$C_4$ perfluoroalkyl, or $C_1$-$C_3$ alkyl.

Embodiment Z provides compounds according to Embodiment U, wherein $R_4$ and $R_{4a}$ together with the nitrogen to which they are attached form -(AA)$_{1-4}$. Preferably, $R_4$ and $R_{4a}$ together with the nitrogen to which they are attached form -(AA)$_3$. More preferably, $R_4$ and $R_{4a}$ together with the nitrogen to which they are attached form -Arg-Arg-Arg.

Embodiment AA provides compounds according to Embodiment U, wherein $R_5$ and $R_{5a}$ are independently —CH$_2$-phenyl or phenyl.

Embodiment BB provides compounds according to Embodiment U, wherein $R_6$ and $R_{6a}$ are —CH$_2$-phenyl or phenyl.

Embodiment CC provides compounds according to Embodiment U, wherein $R_7$ is 4-methylphenyl, phenyl or —CF$_3$.

Embodiment DD provides compounds according to Embodiment U, wherein Base is selected from

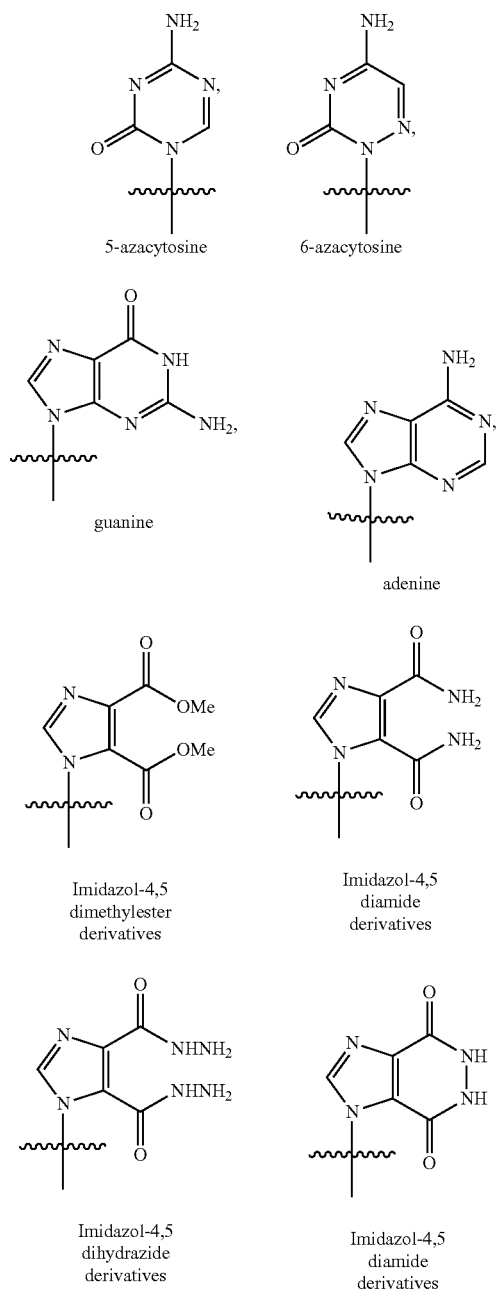

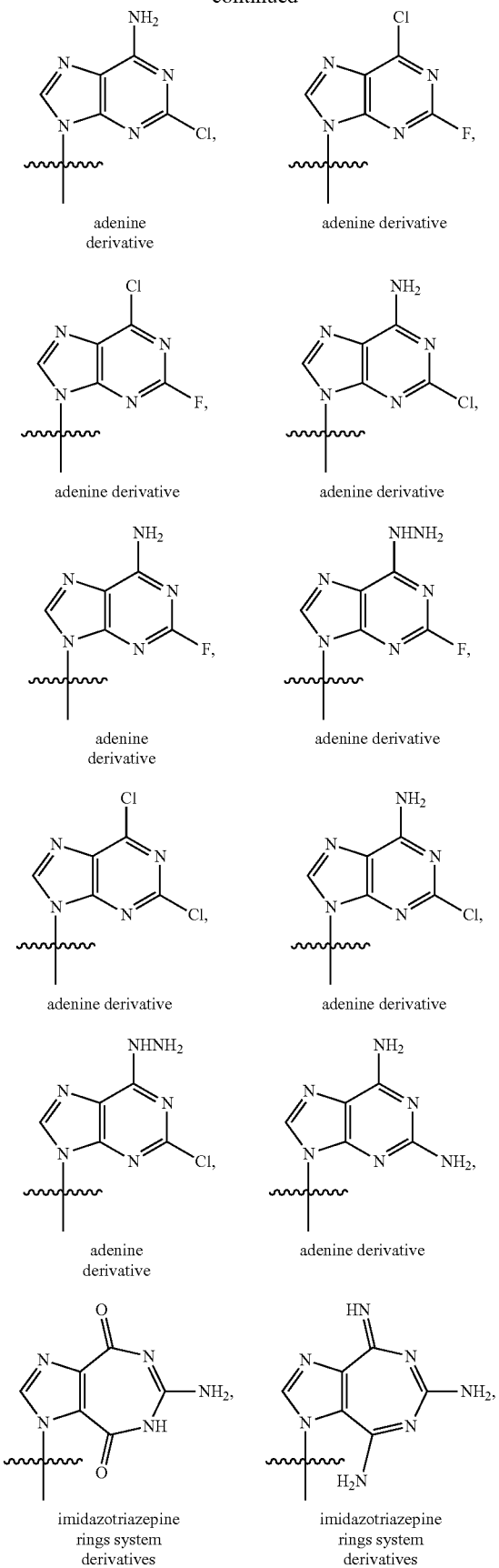

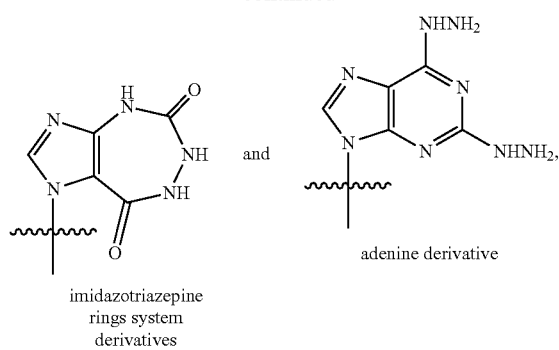 [SMILES: *n1cnc2c1C(=O)NNC(=O)N2 ; *n1cnc2c(NN)nc(NN)nc21]

imidazotriazepine rings system derivatives   and   adenine derivative

Embodiment EE provides compounds according to Embodiment U, wherein Base is selected from

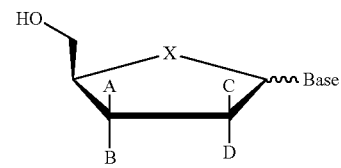

wherein
X is O or S;
one of A and B is $C_1$-$C_6$ alkyl;
the other of A and B is $CONH_2$, $CONR_6R_{6a}$, $CONHNH_2$, $CONHNHR_6$, —C(O)—$NR_4R_{4a}$, —C(O)$OR_2$, $(CH_2)n_1C(O)OR_2$, —C(O)—$R_3$, or —$(CH_2)_nM$;
C and D are independently —H, halo, azide, or —OH;
and Base is selected from the group consisting of

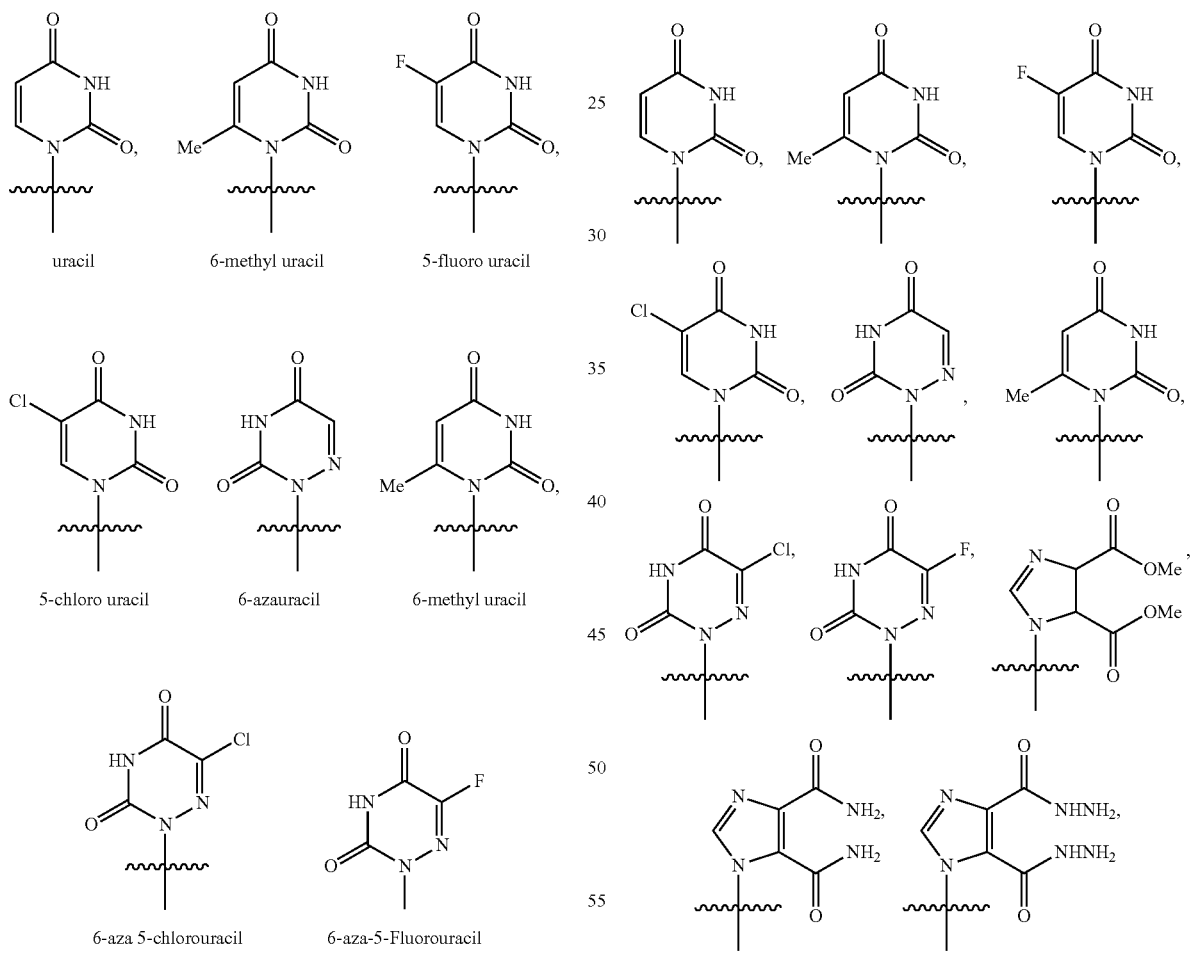

Embodiment FF provides compounds according to Embodiment U, wherein $R_9$ is $C_1$-$C_5$ alkyl, $C_1$-$C_3$ alkyl-aryl, or aryl, wherein the alkyl is optionally substituted with —OH. Preferably, $R_9$ is methyl, ethyl, tert-butyl, benzyl, phenyl, or —$CH_2CH_2OH$.

Embodiment GG provides compounds according to formulae I-IV, of the formula,

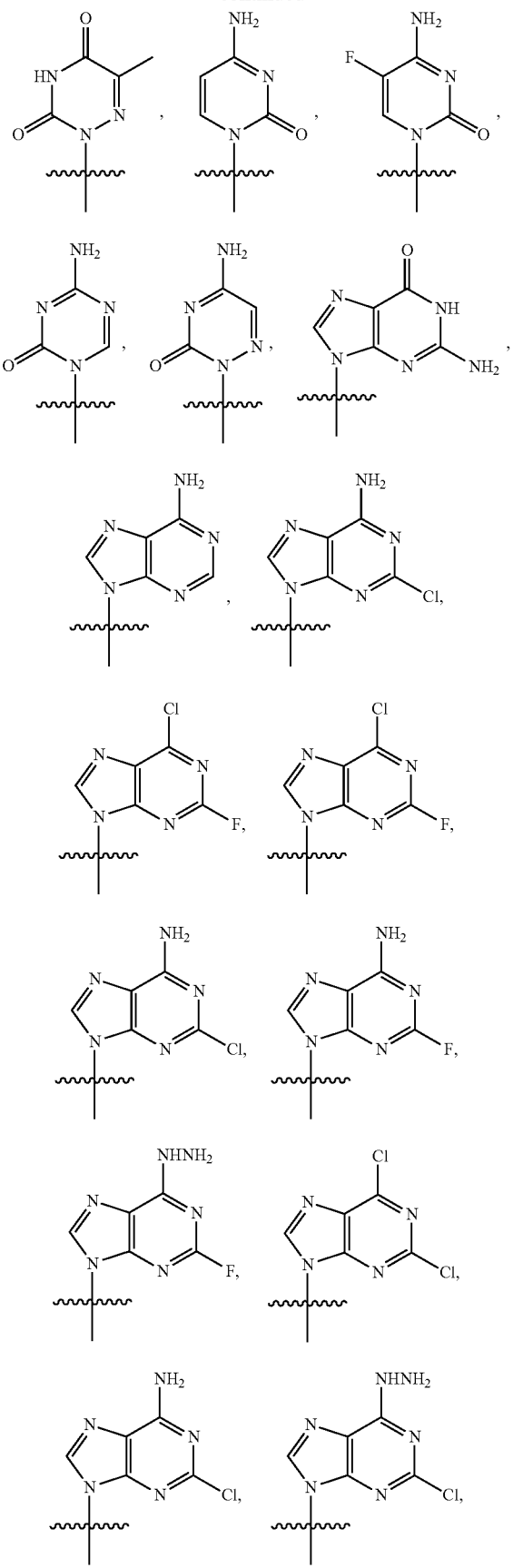

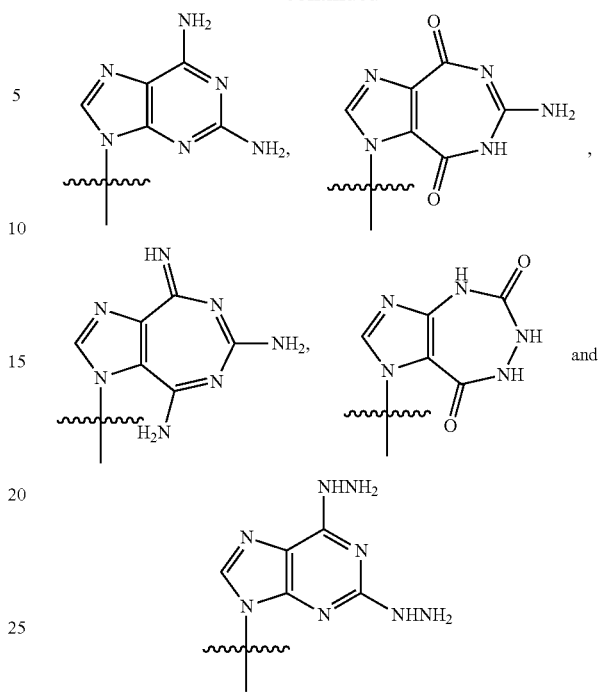

Embodiment HH provides compounds according to Embodiment GG, of the formula,

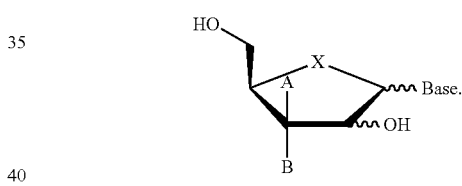

Embodiment II provides compounds according to Embodiment GG or HH, wherein M is —$OR_1$, —$SR_1$, —$CO_2R_2$, —$COR_3$, —$NH(CO)R_5$, —$NR_6R_{6a}$, —$CONR_4R_{4a}$, —$NHSO_2R_7$, —CO—$CH_2OH$, —$SOR_8$, —$SO_2NR_5R_{5a}$, —$O(CO)R_3$, or —$N_3$.

Embodiment JJ provides compounds according to Embodiment II, wherein M is —$OR_1$, —$SR_1$, —$CO_2R_2$, —$NH(CO)R_5$, or —$CONR_4R_{4a}$.

Embodiment KK provides compounds according to any one of Embodiments GG-JJ, wherein one of A and B is methyl, and the other of A and B is —$CONH_2$, —$CONR_6R_{6a}$, —$CONHNH_2$, —$CONHNHR_6$, —C(O)—$NR_4R_{4a}$, —C(O)$OR_2$, —$(CH_2)n_1C(O)OR_2$, —C(O)—$R_3$, or —$(CH_2)_nM$.

Embodiment LL provides compounds according to Embodiment GG or HH, wherein one of A and B is methyl, and the other of A and B is —$CONH_2$, —$CONR_6R_{6a}$, —$CONHNH_2$, —$CONHNHR_6$, —C(O)—$NR_4R_{4a}$, —C(O)$OR_2$, —$(CH_2)n_1C(O)OR_2$, —C(O)—$R_3$.

Embodiment MM provides compounds according to any one of Embodiments GG-LL, wherein X is O.

Embodiment NN provides compounds according to any one of Embodiments GG-MM, wherein the Base is selected from the groups consisting of,

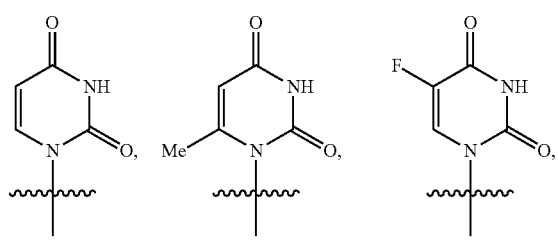
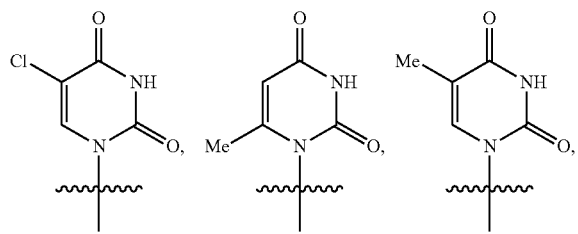
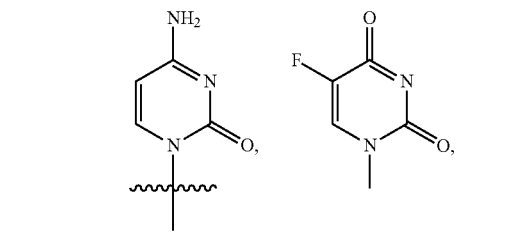
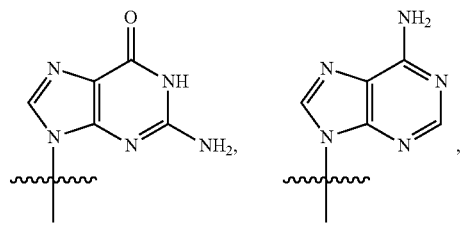
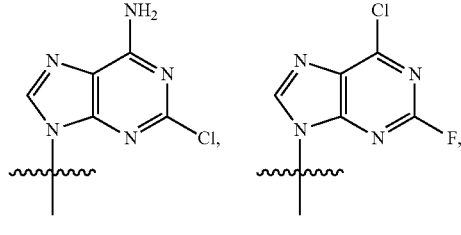
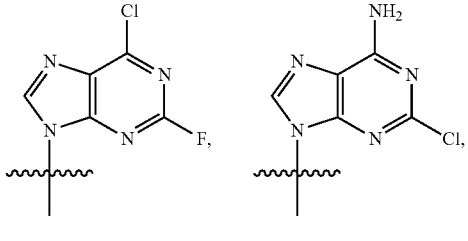
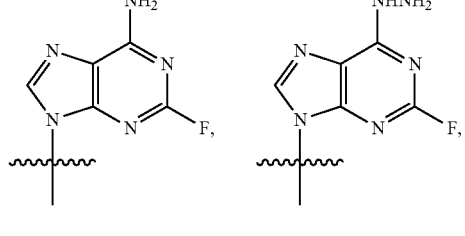
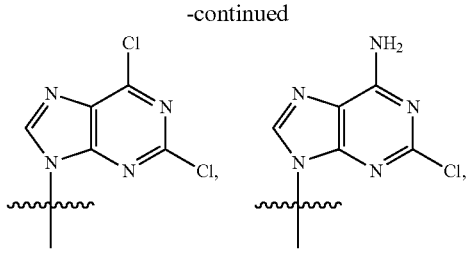
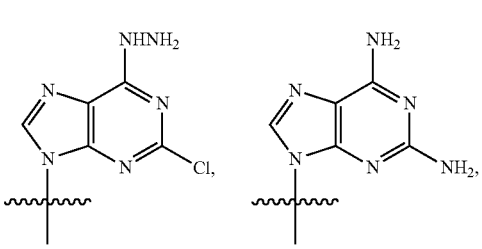
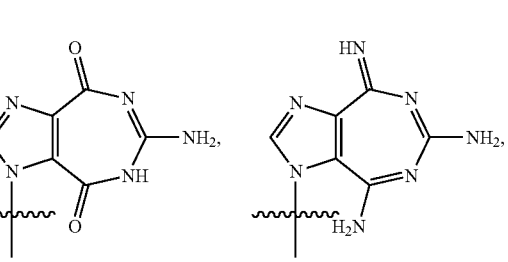
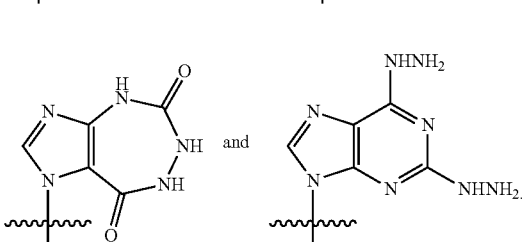
Embodiment OO provides compounds according to any one of Embodiments GG-NN, wherein the Base is selected from the groups consisting of,
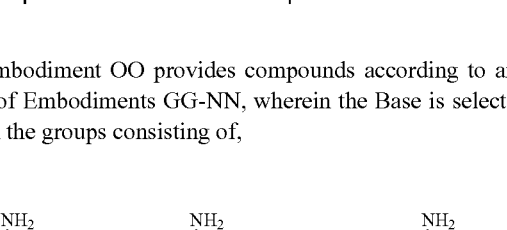
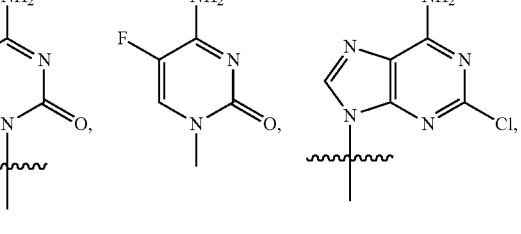
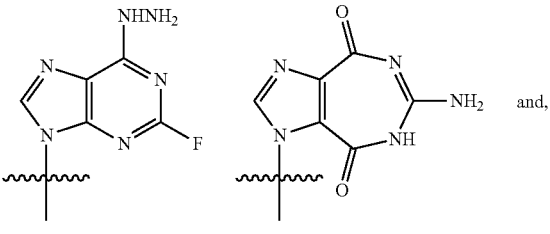

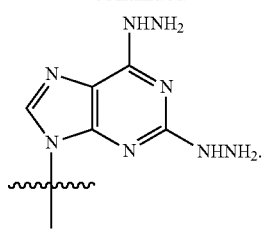

Embodiment PP provides compounds according to any one Embodiments GG-OO of the formula,

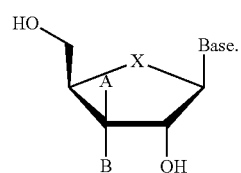

Embodiment QQ provides compounds according to any one Embodiments GG-OO of the formula,

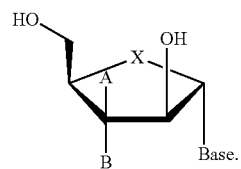

Embodiment RR provides compounds according to formulae XVII and XVIII of the formula,

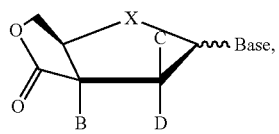

wherein
X is O or S;
B is $C_1$-$C_6$ alkyl, $C_2$-$C_6$ alkenyl, $C_2$-$C_6$ alkynyl, or mono- to per-halo $C_1$-$C_6$ alkyl;
C and D are independently —H, halo, azide, or —OH;
and Base is selected from the group consisting of

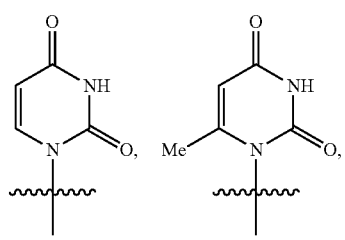

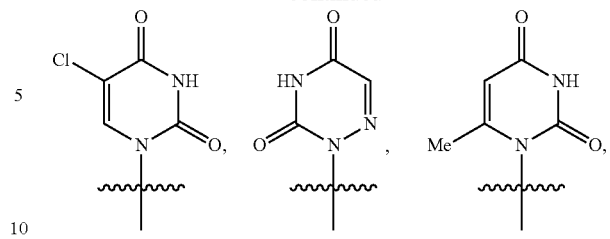

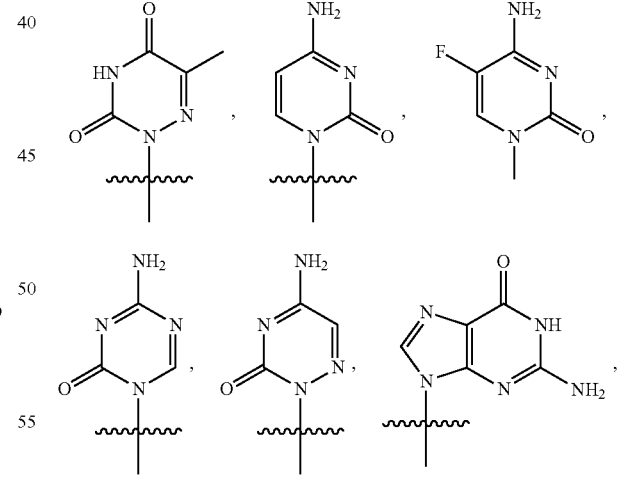

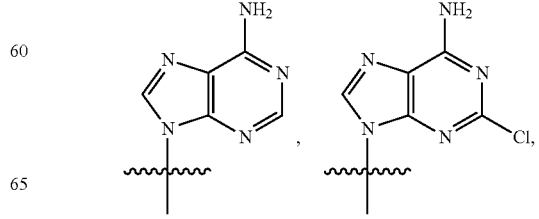

-continued
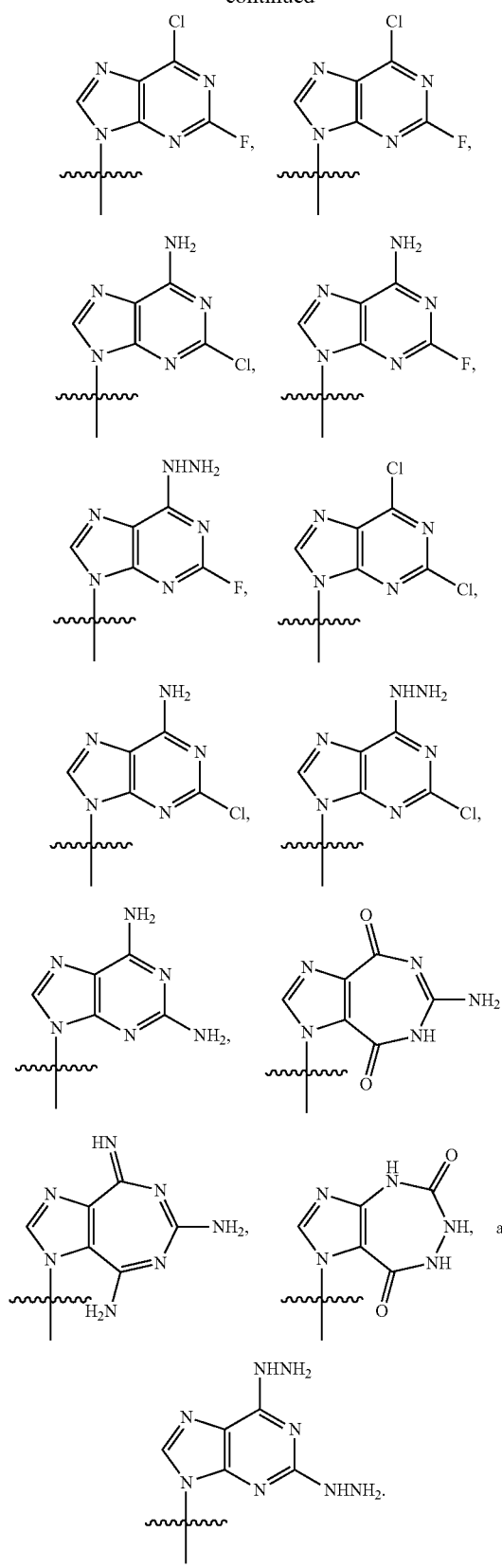
Embodiment SS provides compounds according to Embodiment RR of the formula,
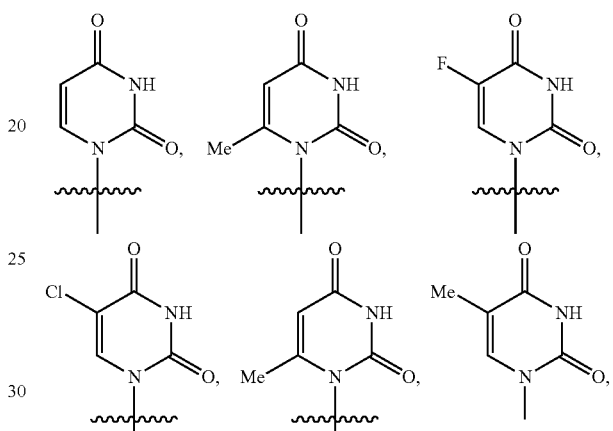
Embodiment TT provides compounds according to Embodiment RR or SS, wherein X is O.
Embodiment UU provides compounds according to any one of Embodiments RR-TT, wherein the Base is selected from the groups consisting of,
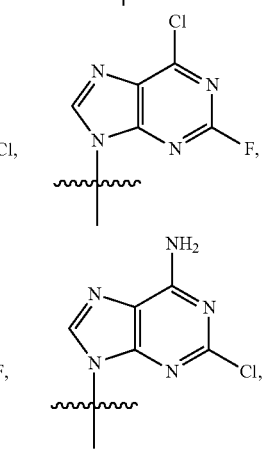

-continued

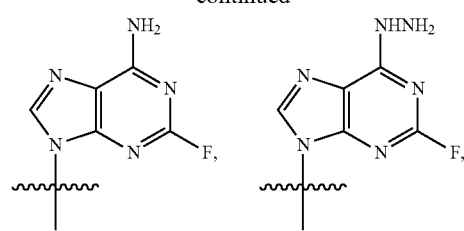

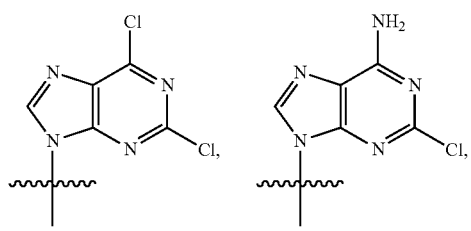

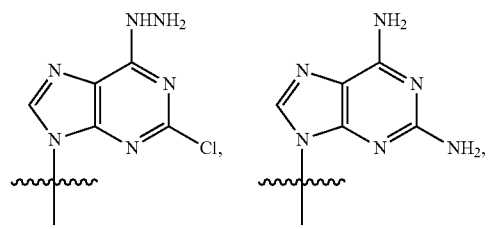

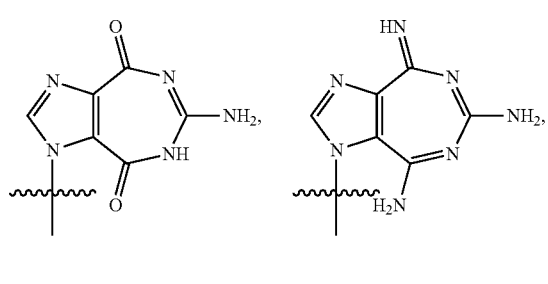

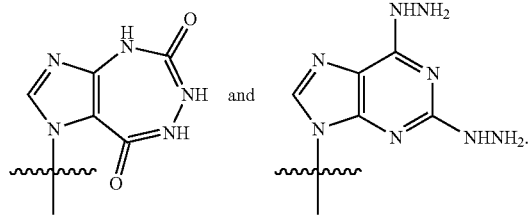

Embodiment UU provides compounds according to any one of Embodiments RR-TT SS, wherein the Base is selected from the groups consisting of,

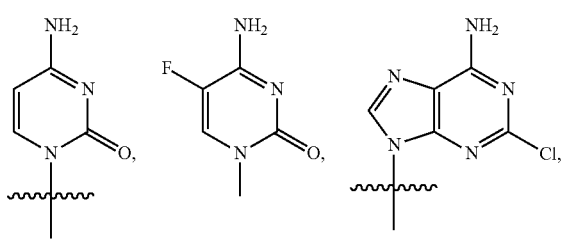

-continued

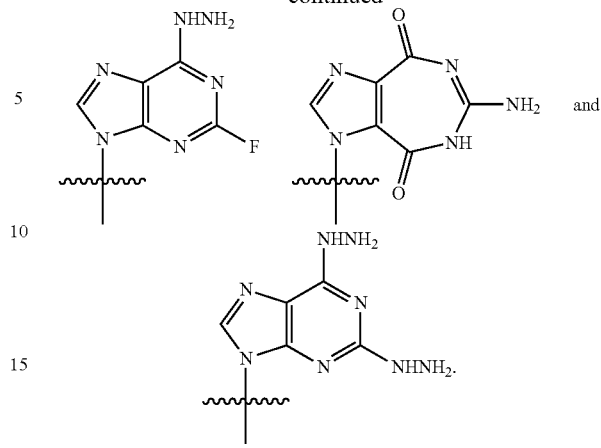

and

Embodiment VV provides compounds according to any one Embodiments RR-UU of the formula,

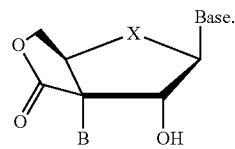

Embodiment WW provides compounds according to any one Embodiments RR-UU of the formula,

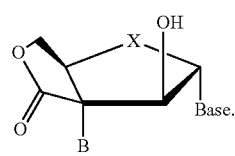

Embodiment XX provides compounds according to any one Embodiments RR-WW, wherein B is $C_1$-$C_6$ alkyl.

Embodiment YY provides compounds according to any one Embodiments RR-XX, wherein B is methyl.

In a second aspect, the invention comprises pharmaceutical compositions comprising a pharmaceutically acceptable carrier, excipient, or diluent and compound according to formulae I-XVI or pharmaceutically acceptable salts thereof.

In a third aspect, the invention comprises methods for inhibiting a virus or tumor comprising contacting a cell in which inhibition is desired with a compound according to formula I-XVI or a pharmaceutical composition according to the second aspect of the invention.

In a fourth aspect, the invention comprises methods for inhibiting a virus or tumor in a patient comprising administering to the patient a pharmaceutical composition according to formulae I-XVI.

In a fifth aspect, the invention comprises methods for treating a disease or condition in a patient, wherein the disease or condition involves a virus or is a tumor, comprising administering to the patient a pharmaceutical composition according to the second aspect of the invention. The disease or condition may be selected from ovarian cancer, cervical cancer, breast cancer, skin cancer, brain cancer, colorectal cancer, lung cancer, bone cancer, glioblastomas, influenza, or diseases caused by HPV, HIV, or HCV.

Definitions

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond, "- - -" means a single or double bond. When a group is depicted removed from its parent formula, the "⌇" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

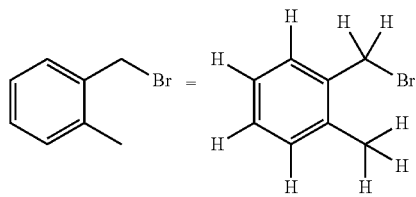

If a group R' (such as, R and $R_1$-$R_9$) is depicted as "floating" on a ring system, as for example in the formula:

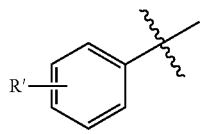

then, unless otherwise defined, a substituent R' may reside on any atom of the ring system, assuming replacement of a depicted, implied, or expressly defined hydrogen from one of the ring atoms, so long as a stable structure is formed.

If a group R' is depicted as floating on a fused ring system, as for example in the formulae:

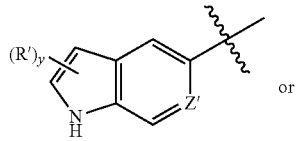

or

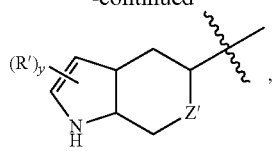

then, unless otherwise defined, a substituent R' may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, Z' equals =CH— or —$CH_2$—) from one of the ring atoms, so long as a stable structure is formed. In the example depicted, the R' group may reside on either the 5-membered or the 6-membered ring of the fused ring system. In the formula depicted above, when y is 2 for example, then the two R' groups may reside on any two atoms of the ring system, again assuming each replaces a depicted, implied, or expressly defined hydrogen on the ring.

When a group R' is depicted as existing on a ring system containing saturated carbons, as for example in the formula:

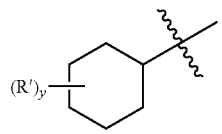

where, in this example, "y" can be more than one, assuming each replaces a currently depicted, implied, or expressly defined hydrogen on the ring; then, unless otherwise defined, where the resulting structure is stable, two R' groups may reside on the same carbon. A simple example is when R' is a methyl group; there can exist a geminal dimethyl on a carbon of the depicted ring (an "annular" carbon). In another example, two R' groups on the same carbon, including that carbon, may form a ring, thus creating a spirocyclic ring (a "spirocyclyl" group) structure with the depicted ring as for example in the formula:

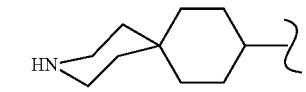

"Alkyl" is intended to include linear, branched, or cyclic hydrocarbon structures and combinations thereof, inclusively. For example, "$C_6$ alkyl" may refer to an n-hexyl, iso-hexyl, cyclobutylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. A "$C_0$" alkyl (as in "$C_0$-$C_6$-alkyl") is a covalent bond. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Alkyl also includes unsaturated hydrocarbon groups, such as alkenyl and alkynyl groups.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent group consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Aryl" refers to aromatic six- to fourteen-membered carbocyclic ring, and includes mono-, bicyclic, fused-polycyclic or fused ring system, or polycyclic groups, for example, benzene, naphthalene, acenaphthylene, anthracene, indane, tetralin, fluorene and the like. Aryl as substituents includes univalent or polyvalent substituents. As univalent substituents, the aforementioned ring examples are named, phenyl, naphthyl, acenaphthyl, anthracenyl, indanyl, tetralinyl, and fluorenyl.

When a group is referred to as "$C_1$-$C_6$ alkylaryl" or "$C_0$-$C_6$ alkylaryl", an aryl moiety is attached to a parent structure via an alkylene group. Examples include benzyl, phenethyl, and the like. Both the aryl and the corresponding alkylene portion of an "$C_1$-$C_6$ alkyl-aryl" or "$C_0$-$C_6$ alkyl-aryl" group may be optionally substituted.

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. The phrase "mono- to per-halogenated" when combined with another group refers to groups wherein one hydrogen, more than one hydrogen, or all hydrogens are replaced with a halo. For example, a "mono- to per-halogenated alkyl" would encompass groups such as —$CH_2F$, —$CH_2CHCl_2$ or —$CF_3$.

"Heteroatom" refers to O, S, N, or P.

"Heterocyclyl" and "heterocycloalkyl" refer to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —$S(O)_{0-2}$—, refers to —S— (sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Heteroaryl" refers specifically to an aromatic heterocyclyl group.

When a group is referred to as "$C_1$-$C_6$ alkylheterocyclyl," "$C_0$-$C_6$ alkyl-heterocyclyl," or "$C_1$-$C_6$ alkylheteroaryl," the heterocyclyl or heteroaryl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group may be optionally substituted. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms. Additionally, for simplicity, the number of annular atoms (including heteroatoms) in a heterocycle may be denoted as "$C_x$-$C_y$," (as in "$C_x$-$C_y$-heterocyclyl" and "$C_x$-$C_y$-heteroaryl" (and the like)), where x and y are integers. So, for example, $C_5$-$C_{14}$-heterocyclyl refers to a 5 to 14 membered ring system having at least one heteroatom and not a ring system containing 5 to 14 annular carbon atoms.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted $C_1$-$C_6$ alkylaryl," both the "$C_1$-$C_6$ alkyl" portion and the "aryl" portion of the molecule may or may not be substituted. A list of exemplary optional substitutions is presented below in the definition of "substituted."

"Substituted" alkyl, aryl, heteroaryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—$CO_2H$), carboalkoxy (that is, acyloxy or —$OC(=O)R$), carboxyalkyl (that is, esters or —$CO_2R$), carboxamido, benzyloxycarbonylamino (CBZ-amino), cyano, acyl, halogen, hydroxy, nitro, sulfanyl, sulfanyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that may or may not have one or more substituents, and each of the substituents may or may not have one or more substituents. But, the substituents of the substituents may not be substituted.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Thus, when a compounds is claimed without any stereochemistry designation, it is understood to include all possible stereoisomers, racemates, and as mixtures of enantiomers and diastereomers.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

When a particular group with its bonding structure is denoted as being bonded to two partners; that is, a divalent group, for example, —$OCH_2$—, then it is understood that either of the two partners may be bound to the particular group at one end, and the other partner is necessarily bound to the other end of the particular group, unless stated explicitly otherwise. Stated another way, divalent groups are not to be construed as limited to the depicted orientation, for example "—$OCH_2$—" is meant to mean not only "—$OCH_2$—" as drawn, but also "—$CH_2O$—."

Natural, non-natural, D- or L-amino acids ("AA") include all known naturally occurring amino acids as well as synthetic amino acids. Natural amino acids include, for example, D- and L-isomers of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Non-natural amino acids include (1) alpha-amino acid compounds of the form $NH_2$—CH(R)—COOH, wherein R is a substituent not present in a natural amino acid, including those of $R^o$ (below) which are not present in natural amino acids; and (2) beta-amino acid compounds of the form, $NH_2$—$CH_2$CH($R^o$)—COOH and $NH_2$—CH($R^o$)$CH_2$—COOH, where $R^o$ is a substituent of a natural amino acid or a non-natural alpha-amino acid, such as hydrogen, halogen, cyano, nitro, amino, hydroxy, thio, $C_1$-$C_6$ alkoxy, $C_1$-$C_6$alkylthio, $C_1$-$C_6$ alkylamino, di($C_1$-$C_6$ alkyl)amino, $C_1$-$C_6$ alkylcarbonyl, —C(O)H, —COOH, —$CONH_2$, —C(=NH)$NH_2$, —CON(H)($C_1$-$C_6$ alkyl), —CON($C_1$-$C_6$ alkyl)$_2$, —COO($C_1$-$C_6$ alkyl), $C_1$-$C_6$ alkyl, aryl, heteroaryl, $C_3$-$C_8$ cycloalkyl, heterocyclyl, —$C_1$-$C_6$ alkyl-aryl, —$C_1$-$C_6$ alkyl-heteroaryl, —$C_1$-$C_6$ alkyl-$C_3$-$C_8$ cycloalkyl, and —$C_1$-$C_6$ alkyl-heterocyclyl wherein the alkyl, aryl, heteroaryl, cycloalkyl, heterocyclyl, -alkyl-aryl, -alkyl-heteroaryl, -alkyl-cycloalkyl, and -alkyl-heterocyclyl groups are optionally substituted with one or more (e.g., 1, 2, or 3) groups which are each independently halogen, cyano, nitro, amino, hydroxy, thio, $C_1$-$C_6$ alkoxy, $C_1$-$C_6$alkylthio, $C_1$-$C_6$ alkylamino, di($C_1$-$C_6$ alkyl)amino, $C_1$-$C_6$ alkylcarbonyl, —C(O)H, —COOH, —$CONH_2$, —C(=NH)$NH_2$, —CON(H)($C_1$-$C_6$ alkyl), —CON($C_1$-$C_6$ alkyl)$_2$, —COO($C_1$-$C_6$ alkyl), $C_1$-$C_6$ alkyl, aryl, heteroaryl, $C_3$-$C_8$ cycloalkyl, heterocyclyl, —$C_1$-$C_6$ alkyl-aryl, —$C_1$-$C_6$ alkyl-heteroaryl, —$C_1$-$C_6$ alkyl-$C_3$-$C_8$ cycloalkyl, and —$C_1$-$C_6$ alkyl-heterocyclyl. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, and β-alanine.

Purine and pyrimidine derivatives include all naturally occurring purine and pyrimidine compounds, such as those that are found in nucleic acids. Purine and pyrimidine also include modified naturally occurring purines and pyrimidines, for example, modified with groups including, but not limited to, halo or alkyl groups. Particular examples of purine and pyrimidine derivatives include, but are not limited to,

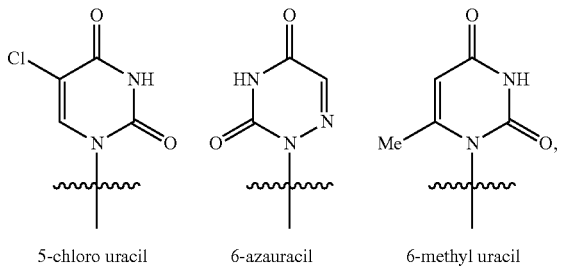

5-chloro uracil
6-azauracil
6-methyl uracil

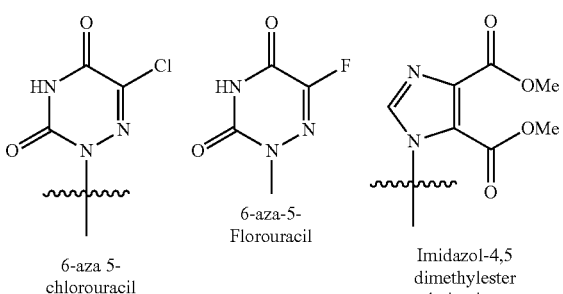

6-aza 5-chlorouracil
6-aza-5-Florouracil
Imidazol-4,5 dimethylester derivatives

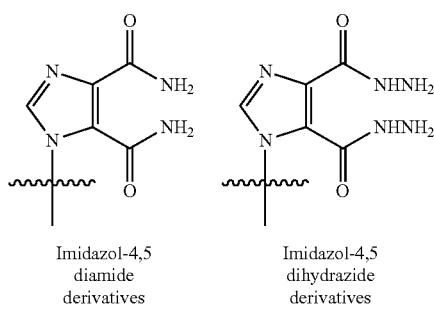

Imidazol-4,5 diamide derivatives
Imidazol-4,5 dihydrazide derivatives

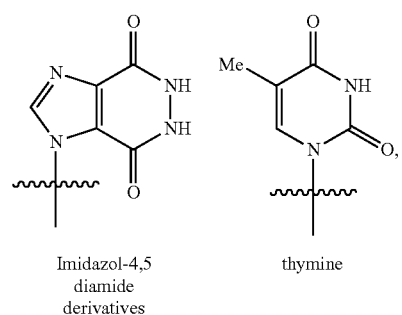

Imidazol-4,5 diamide derivatives
thymine

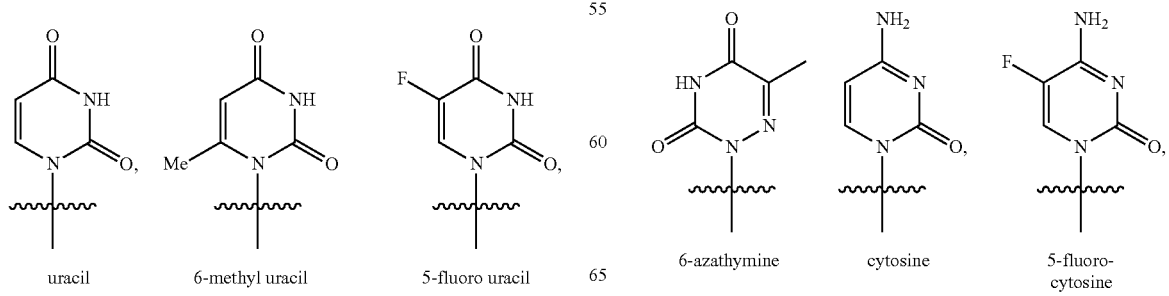

uracil
6-methyl uracil
5-fluoro uracil
6-azathymine
cytosine
5-fluoro-cytosine

-continued

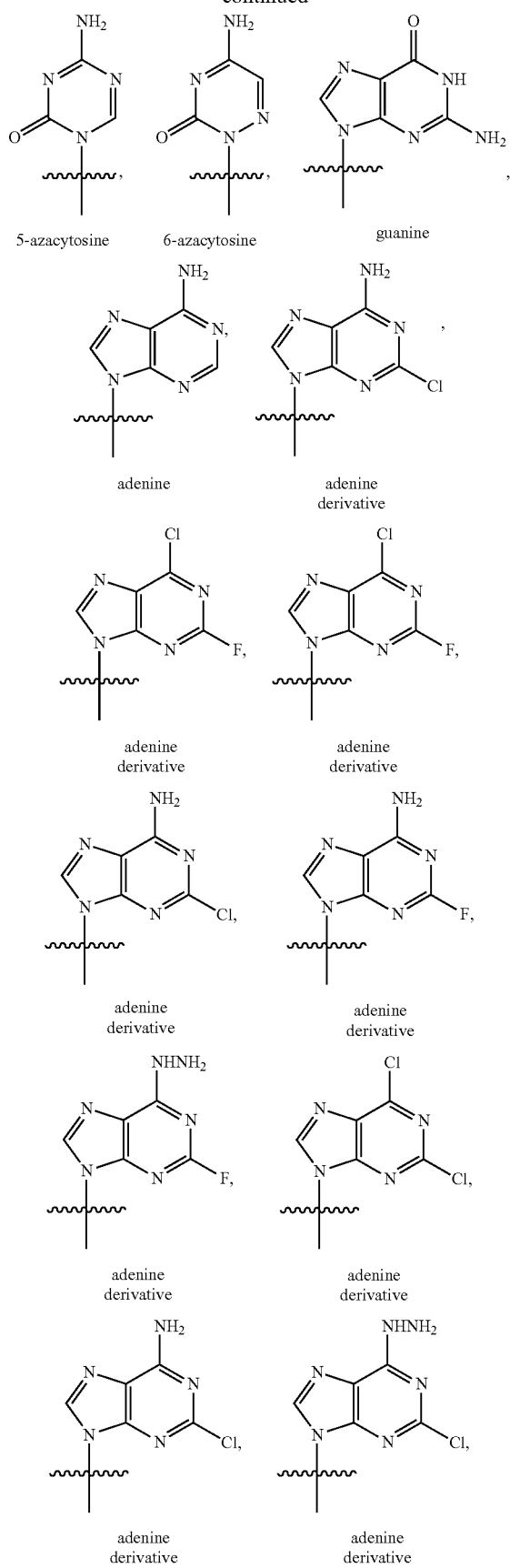

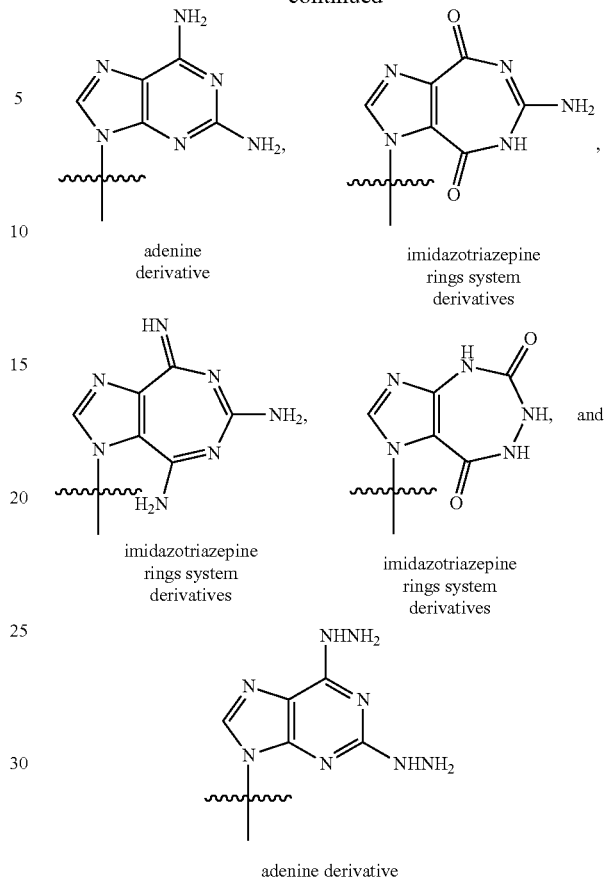

A "protecting group" or "protective group" is any molecule introduced into another molecule by chemical modification of a functional group in order to obtain chemoselectivity in a subsequent chemical reaction. For example, a protecting group may be attached to any of the functional groups of the compounds according formulae I-VIII, or their intermediates. For example, a carbonyl group may be protected by converted it to an acetal or cyclic ketal. The acetal or cyclic ketal is then called a protecting group for the carbonyl. The acetal or cyclic ketal can be converted back to the carbonyl by reacting with an aqueous acid. This is referred to as deprotection. Protecting groups for alcohols include acetyl, tetrahydropyranyl ether, methoxymethyl ether, β-methoxyethoxymethyl ether, p-methoxybenzyl ether, methylthiomethyl ether, and silyl ether. Amine protecting groups include carbobenzyloxy group, tert-butyloxycarbonyl, 9-fluorenylmethyloxycarbonyl, and benzyl. Carbonyl protecting groups includes acetals and acylals. Carboxylic acid protecting groups include ethyl esters, benzyl esters, and silyl esters.

In addition to the preferred embodiments recited hereinabove, also preferred are embodiments comprising combinations of preferred embodiments.

Methods for the preparation and/or separation and isolation of single stereoisomers from racemic mixtures or non-racemic mixtures of stereoisomers are well known in the art. For example, optically active (R)- and (S)-isomers or L- and D-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium and magnesium salts. Salts derived from pharmaceutically acceptable organic non-toxic bases include salts or primary, secondary, and tertiary amines, substituted amines including naturally occurring substituted amines, cyclic amines and basic ion exchange resin, such as isopropylamine, tri-methylamine, diethanolamine, diethylamine, triethylamine, tripropylamine, ethanolamine, 2-dimethylaminoethanol, 2-diethylamino-ethanol, tometheamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethylmorpholine, polyamine resins and the like. (See, for example, S. M. Berge, et al., "Pharmaceutical Salts," J. Pharm. Sci., 1977; 66:1-19 which is incorporated herein by reference.)

"Pharmaceutically acceptable salts" also refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the invention may also be prepared as prodrugs. Prodrugs refers to compounds that are transformed (typically rapidly) in vivo to yield the parent compound of the above formula I-XXVIII, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the invention can also be used as pharmacological tools. In addition to their use as inhibitors, the compounds of the invention can be used to investigate the function and structure of cellular and viral components. Thus, the compounds of the invention can be used to investigate the interaction of cellular entities, or the interaction of cellular entities with viruses.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

General Administration

In the second aspect, the invention provides pharmaceutical compositions comprising a nucleotide analogue according to the invention and a pharmaceutically acceptable carrier, excipient, or diluent. In certain other preferred embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

General Synthetic Procedures

The compounds of the invention can be prepared by methods well known to those skilled in the art using reagents readily available. For example, the compounds of the invention comprising a quaternary carbon center may be prepared according to Cardinal-David et al. ("Synthesis of tertiary and quaternary stereogenic centers: a diastereoselective tandem reaction sequence combining Mukaiyama and free radical-based allylation," *J. Org. Chem.* 2005, 70, 776-784), which is incorporated by references in its entirety. For example, the compounds of the invention can be prepared according to reaction Schemes 1-8.

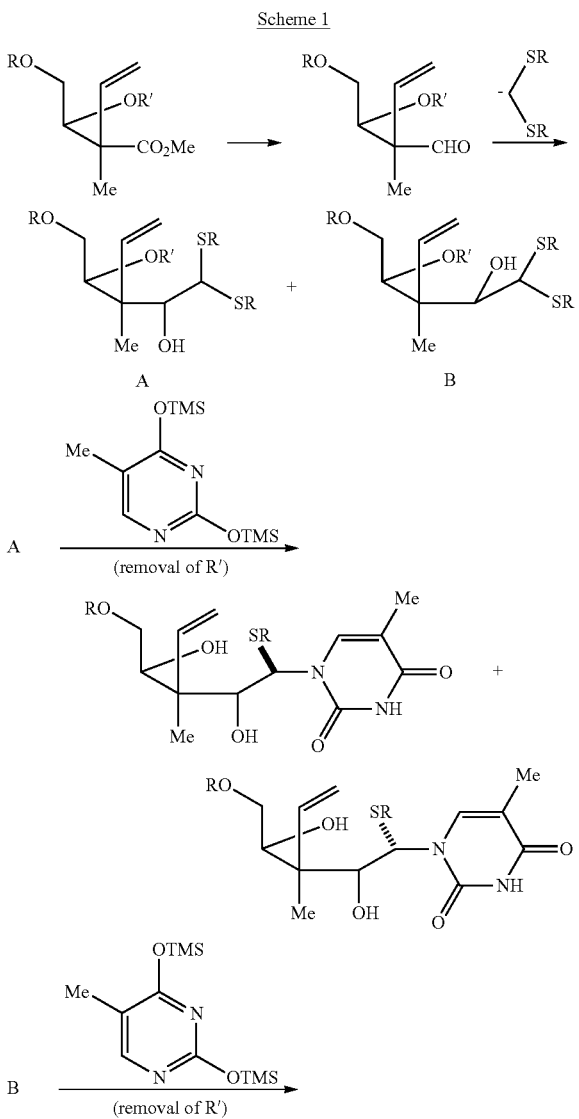

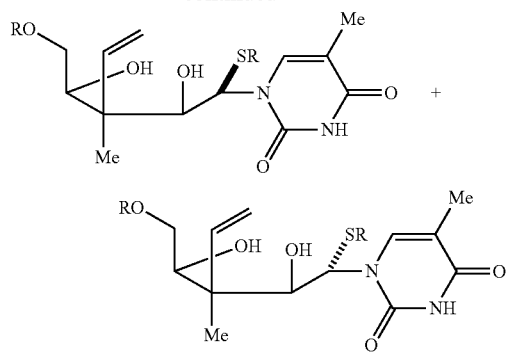
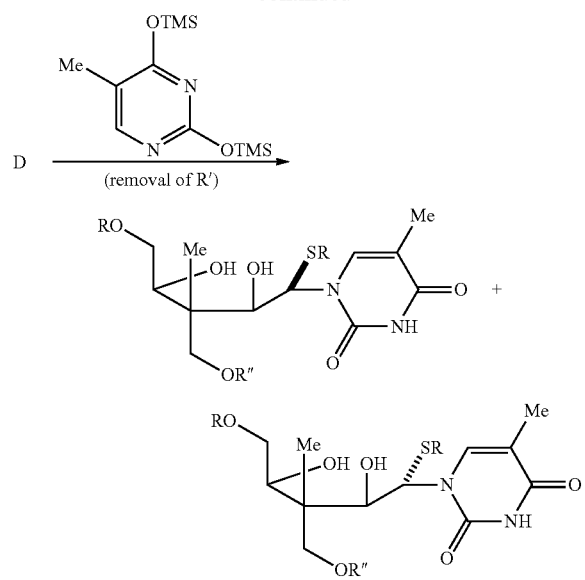
Scheme 2
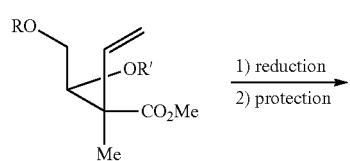
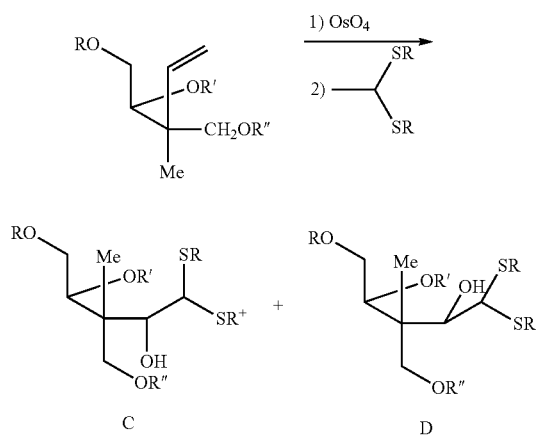
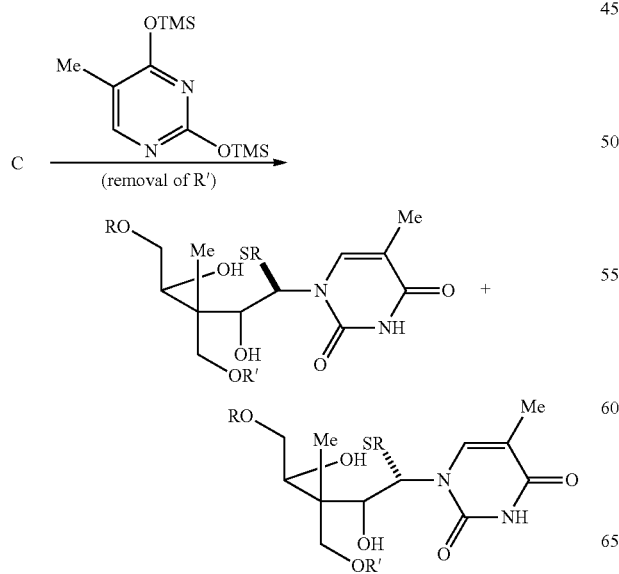
Scheme 3
Synthesis of Oxy derivatives
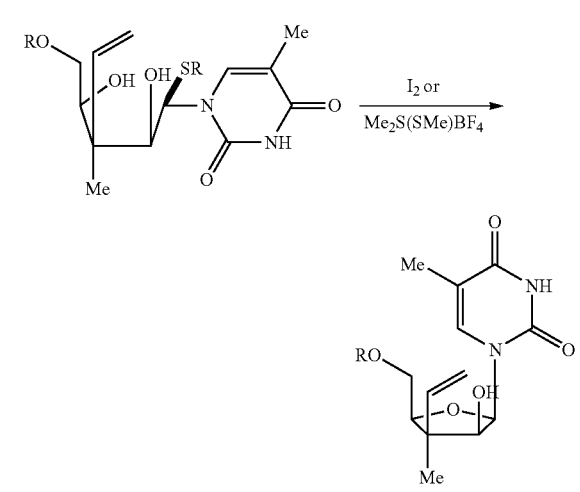

57
-continued
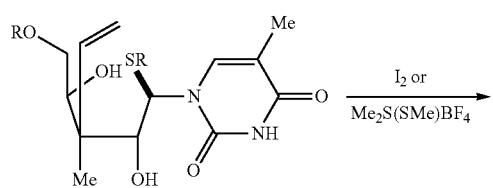
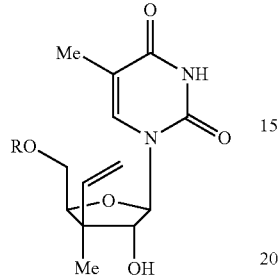
Scheme 4
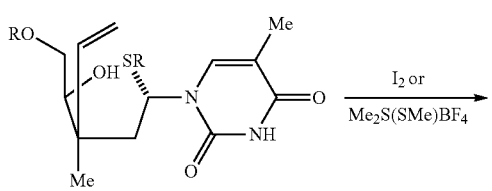
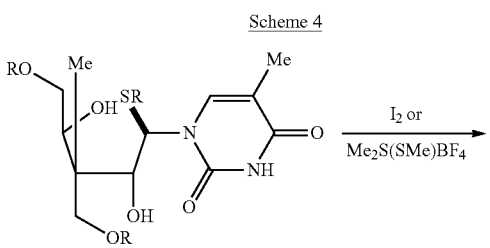
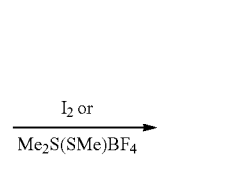
58
-continued
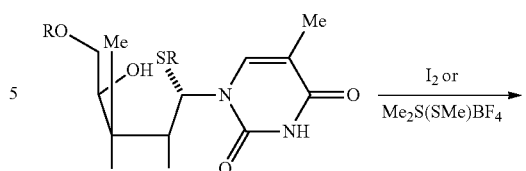
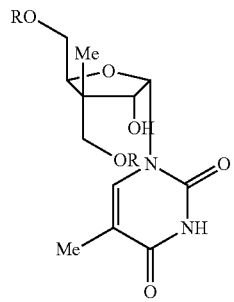
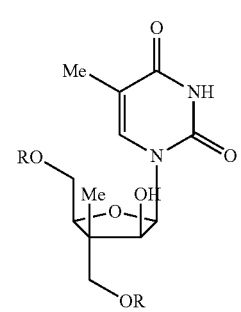
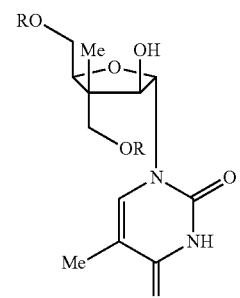

Scheme 5
Synthesis of the C-4 thio analogues
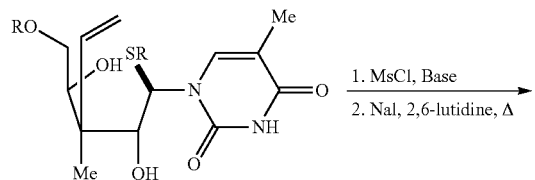
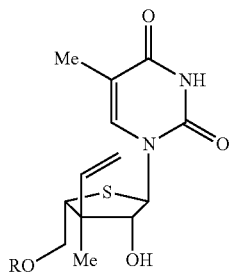
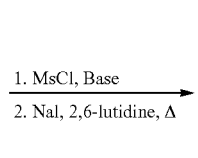
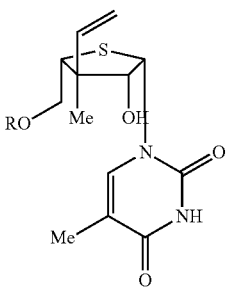
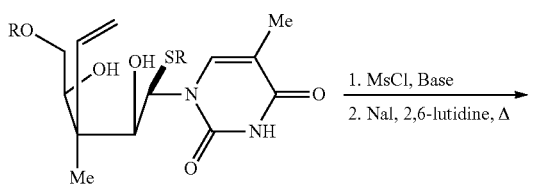
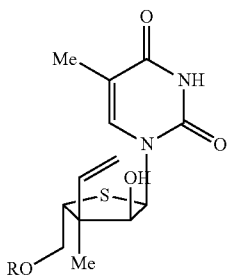
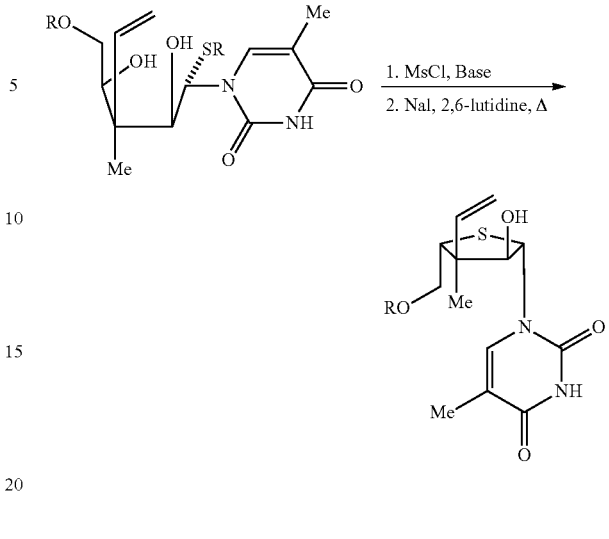
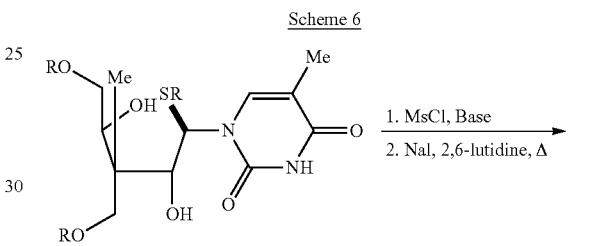
Scheme 6
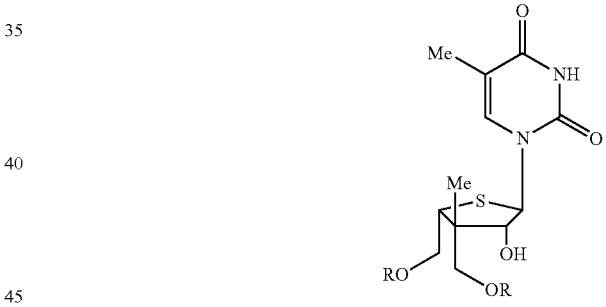
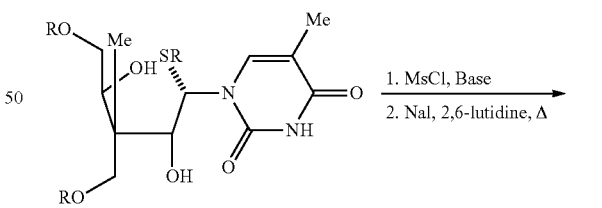
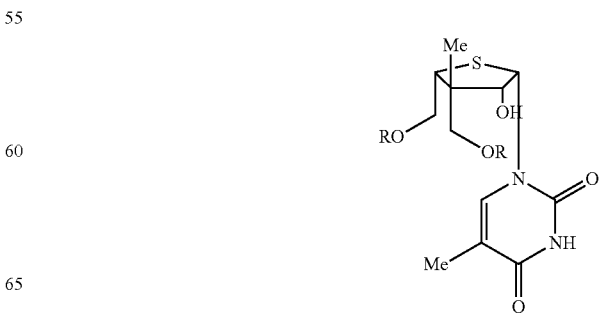

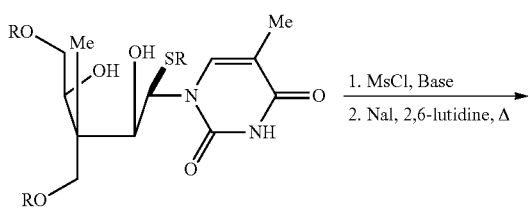
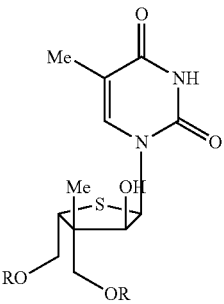
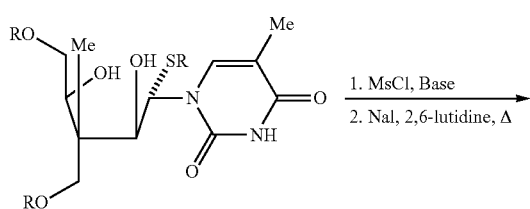
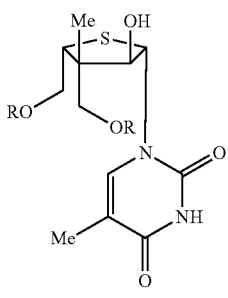
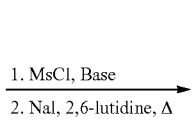
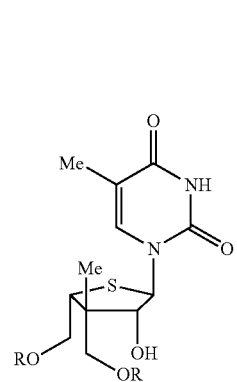
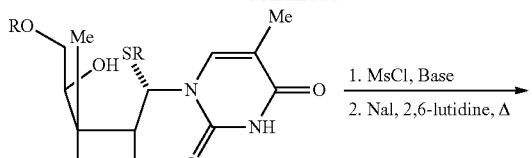
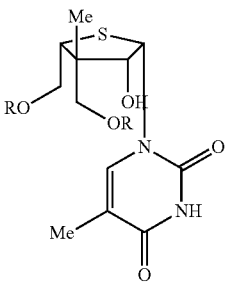
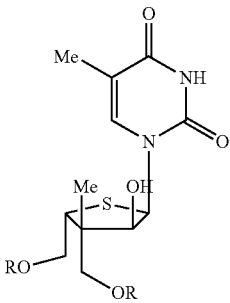
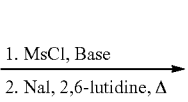
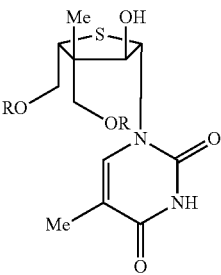

Scheme 7

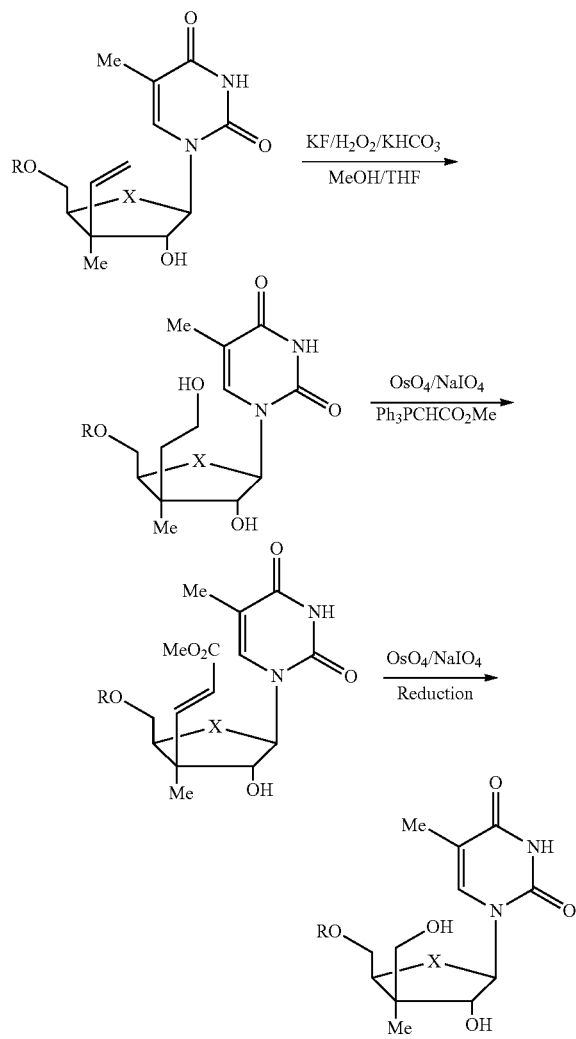

X = O, S

Scheme 8

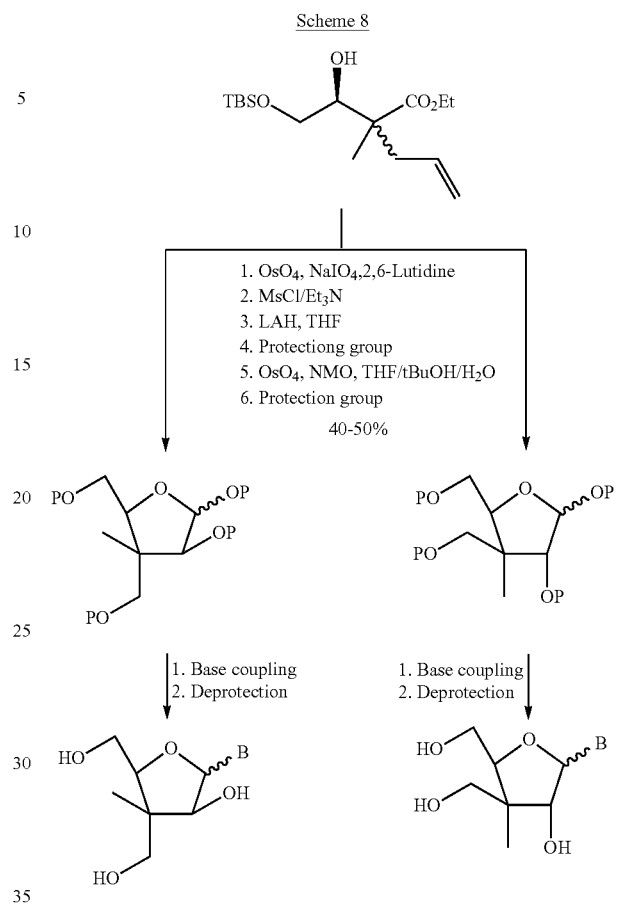

One skilled in the art would recognize that the compounds of the invention can also be made using other well known synthetic methods within the knowledge of those skilled in the art. For example, depending on the identity of the enantiomeric starting materials, the L-isomers or D-isomers in the 4' position of the compounds of the invention can be made. All such enantiomeric products are embodied by the compounds of the invention.

| LCB # | Structure | MW |
|---|---|---|
| 1056 | (structure shown) $C_2$ = 2:1; 1,2-trans/1,2-cis ≥ 20:1 | $C_{11}H_{17}N_3O_5$<br>Exact Mass: 271.12<br>Mol. Wt: 271.27 |
| 1077 | (structure shown) β | $C_{11}H_{17}N_5O_5$<br>Exact Mass: 299.1230<br>MW: 299.2832 |

-continued

| LCB # | Structure | MW |
|---|---|---|
| 1077 | (β) | $C_{11}H_{17}N_5O_5$<br>Exact Mass: 299.1230<br>MW: 299.2832 |
| 1079 | 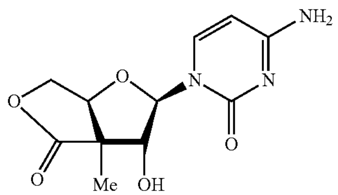 | $C_{11}H_{13}N_3O_5$<br>Exact Mass: 267.0855<br>MW: 267.2380 |
| 1080 | 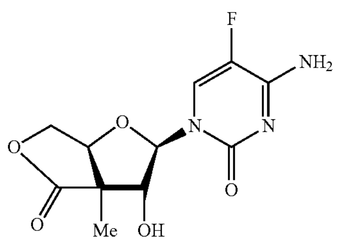 | $C_{11}H_{12}FN_3O_5$<br>Exact Mass: 285.0761<br>MW 285.2285 |
| 1082 | 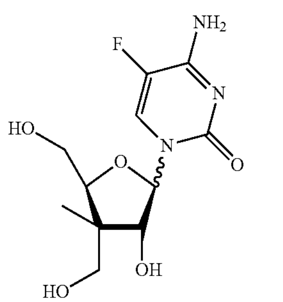 | $C_{11}H_{16}FN_3O_5$<br>Exact Mass: 289.1074<br>MW: 289.2602 |
| 1085 | 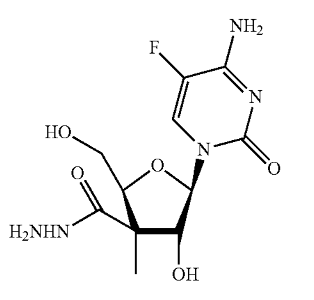 | $C_{11}H_{16}FN_5O_5$<br>Exact Mass: 317.1135<br>MW: 317.2736 |
| 1086 | (±) | $C_{14}H_{22}N_8O_5$<br>Exact Mass: 382.1713<br>MW: 382.3751 |

-continued

| LCB # | Structure | MW |
|---|---|---|
| 1087 | (structure) (±) | C₁₁H₁₆N₄O₅<br>Exact Mass: 284.11<br>MW: 284.27 |
| 1091 | (structure) | C₁₂H₁₆ClN₅O₄<br>Exact Mass: 329.0891<br>MW 329.7395 |
| 1094 | (structure) (±)<br>1094-A | C₁₂H₁₆ClN₅O₄<br>Exact Mass: 329.0891<br>MW: 329.7395 |
| | (structure) (±)<br>1094-B | |
| 1095 | (structure) (±) | C₁₁H₁₇N₃O₅<br>Exact Mass: 271.1168<br>MW: 271.2698 |
| 1096 | (structure) (±) | C₁₁H₁₆FN₃O₅<br>Exact Mass: 289.1074<br>MW: 289.2602 |

| LCB # | Structure | MW |
|---|---|---|
| 1097 | 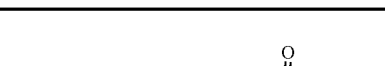 | $C_{13}H_{17}N_5O_6$<br>Exact Mass: 339.1179<br>MW: 339.3040 |

EXAMPLE 1

Synthesis of Sugar Scaffolds

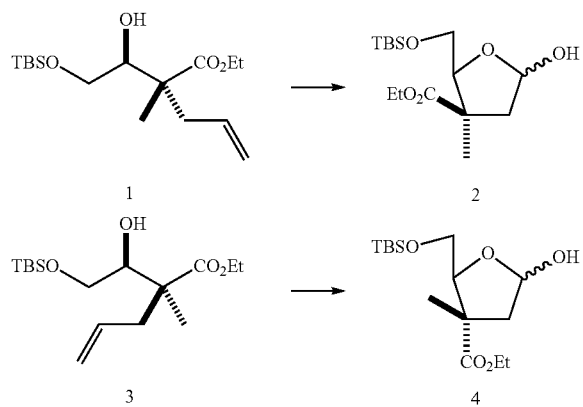

To compound 1 or 3 (1 equiv) in a 1,4-Dioxane/H$_2$O solution at room temperature is added sequentially 2,6-Lutidine (2 equiv), OsO$_4$ (0.01 equiv) and NaIO$_4$ (4 equiv). The reaction is stirred 5 h at room temperature before filtration on a Celite pad (Et$_2$O). The solids are washed with Et$_2$O. Most of ether is evaporated before addition of a saturated solution of Na$_2$S$_2$O$_3$ and stirring is continued overnight. Evaporation of volatiles and extraction with Et$_2$O (×4) and drying on MgSO$_4$. After evaporation of volatiles, the residue is used as a mix of anomers (89%).

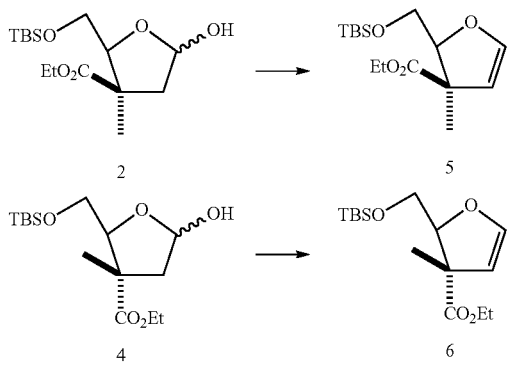

To a lactol 2 or 4 (1 equiv) solution in CH$_2$Cl$_2$ at 0° C. is added NEt$_3$ (3 equiv) and MsCl (1.2 equiv). Stirring for 2 h at 0° C. then 2 h at room temperature. The solution is refluxed for 18 h. At room temperature silica gel is added and stirred for 15 min before evaporation of most of CH$_2$Cl$_2$. The residue is rapidly percolated through a pad of silica gel (Hex/AcOEt 85:15) to yield the corresponding glycal (85%).

(±) (2S,3S)-ethyl 2-((tert-butyldimethylsilyloxy)methyl)-3-methyl-2,3-dihydrofuran-3-carboxylate 5

$^1$H NMR (500 MHz, CDCl$_3$) δ 6.51 (d, 1H, J=2.7 Hz), 5.16 (d, 1H, J=2.7 Hz), 4.97 (t, 1H, J=6.1 Hz), 4.34 (q, 2H, J=7.1 Hz), 4.03 (d, 2H, J=5.7 Hz), 1.46-1.44 (m, 6H), 1.07 (s, 9H), 0.26 (s, 6H); $^{13}$C NMR (125 MHz, CDCl$_3$) δ 175.3, 146.0, 107.1, 85.6, 62.1, 61.3, 54.3, 26.1, 18.8, 18.5, 14.4, −5.1, −5.2. HRMS (ESI) calcd for C$_{15}$H$_{29}$O$_4$Si: 301.1835, found: 301.1825 (−1.4 ppm).

(±) (2S,3R)-ethyl 2-((tert-butyldimethylsilyloxy)methyl)-3-methyl-2,3-dihydrofuran-3-carboxylate 6

$^1$H NMR (500 MHz, CDCl$_3$) δ 6.40 (d, 1H, J=2.7 Hz), 5.00 (d, 1H, J=2.7 Hz), 4.26 (dd, 1H, J=4.7 Hz, J=6.2 Hz), 4.15 (m, 2H), 3.88 (dd, 1H, J=6.4 Hz, J=11.0 Hz), 3.83 (dd, 1H, J=4.6 Hz, J=11.0 Hz), 1.44 (s, 3H), 1.28 (t, 3H, J=7.1 Hz), 0.90 (s, 9H), 0.07 (s, 3H), 0.06 (s, 3H).

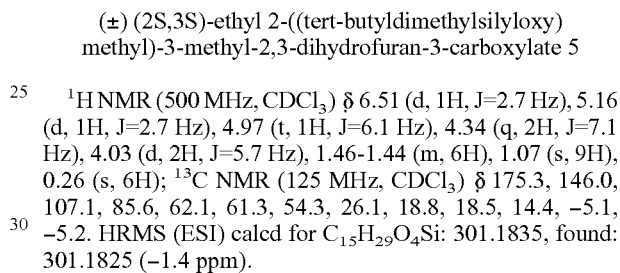

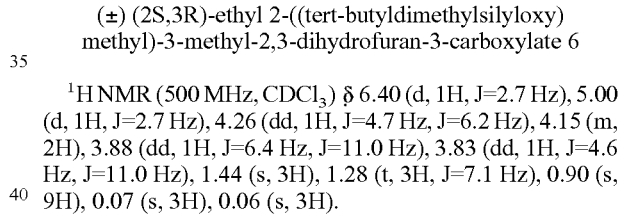

To a glycal (1 equiv) solution in THF at −40° C. is added LiAlH$_4$ (1.5 equiv). Temperature is gradually raised to 0° C. and stirred for 3 h at this temperature before addition of Na$_2$SO$_4$.10H$_2$O, Stirring for 30 min before MgSO$_4$ is added. The suspension is stirred overnight at room temperature before filtration on a pad of Celite. After evaporation, the crude diol (quant.) is used for the next step. To a solution of the diol (1 equiv) in CH$_2$Cl$_2$/pyridine at 0° C. is added BzCl (2.4 equiv) and DMAP (0.2 equiv). Stirring overnight at room temperature then evaporation of pyridine. The residue is dissolved in Hexanes and rapidly percolated through a pad of silica gel (Hex/AcOEt 90:10) to yield the corresponding benzoylated alcohols (quant.).

(2S,3R)-3-methyl-2,3-dihydrofuran-2,3-diyl] dimethanediyl dibenzoate 7

$^1$H NMR (500 MHz, CDCl$_3$) 8.04-8.12 (m, 4H), 7.56-7.62 (m, 2H), 7.43-7.49 (m, 4H), 6.42 (d, J=2.5 Hz, 1H), 4.92 (d, J=2.5 Hz, 1H), 4.76 (dd, J=4.0, 7.5 Hz, 1H), 4.62 (dd, J=4.0, 12.0 Hz, 1H), 4.54 (dd, J=8.0, 11.5 Hz, 1H), 4.34 (d, J=11.0 Hz, 1H), 4.26 (d, J=11.0 Hz, 1H), 1.30 (s, 3H) ppm; HRMS (ESI) calcd for C$_{21}$H$_{20}$NaO$_5$: 375.1203. Found: 375.1213 (+2.8 ppm).

(2S,3S)-3-methyl-2,3-dihydrofuran-2,3-diyl] dimethanediyl dibenzoate 8

$^1$H NMR (500 MHz, CDCl$_3$) 8.02-8.10 (m, 4H), 7.54-7.61 (m, 2H), 7.41-7.48 (m, 4H), 6.44 (d, J=2.5 Hz, 1H), 4.92 (d, J=2.5 Hz, 1H), 4.82 (dd, J=2.5 Hz, 1H), 4.68 (dd, J=8.0, 12.0 Hz, 1H), 4.50 (dd, J=4.0, 8.0 Hz, 1H), 4.36 (d, J=12.0 Hz, 1H), 4.25 (d, J=12.0 Hz, 1H), 1.39 (s, 3H); HRMS (ESI) calcd for C$_{21}$H$_{21}$O$_5$: 353.1384. Found: 353.1384 (+0.2 ppm).

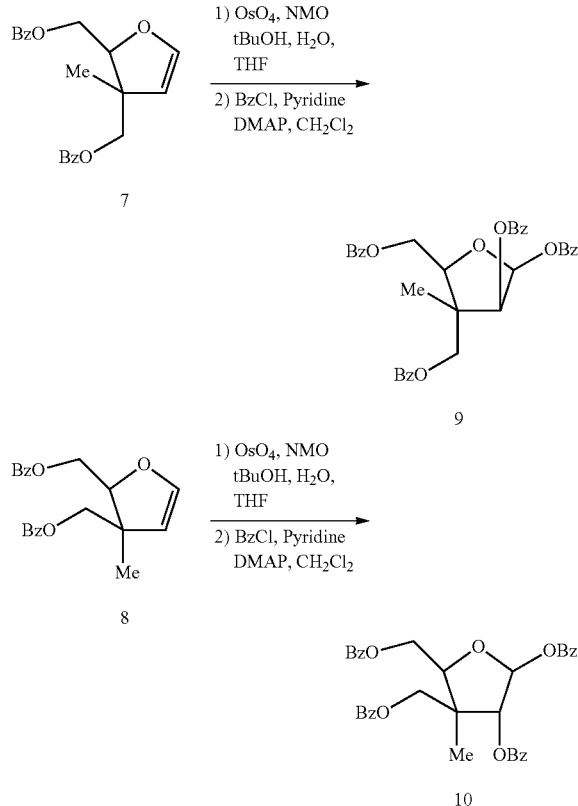

ture. Evaporation of volatiles, extraction with Et$_2$O (×4) and drying on MgSO$_4$. After evaporation of volatiles, the diol is used as a mix of anomers of diastereoisomers at C-2 in the next step. To a solution of the diol (1 equiv) in CH$_2$Cl$_2$/pyridine at 0° C. is added BzCl (2.4 equiv). Stirring overnight at room temperature then evaporation of pyridine. The residue is dissolved in Hexanes and rapidly percolated through a pad of silica gel (Hex/AcOEt 80:20) to yield the corresponding perbenzoylated compounds as a mixture of anomers (82%).

[(2S,3R,4S)-4,5-bis(benzoyloxy)-3-methyltetrahydrofuran-2,3-diyl]dimethanediyl dibenzoate 9

$^1$H NMR (500 MHz, CDCl$_3$) 7.92-8.15 (m, 16H$_{majo+mino}$), 7.32-7.66 (m, 24H$_{majo+mino}$), 6.90 (d, J=4.5 Hz, 1H$_{majo}$), 6.83 (d, J=4.5 Hz, 1H$_{mino}$), 6.66 (d, J=1.5 Hz, 1H$_{mino}$), 6.56 (s, 1H$_{majo}$), 5.96 (d, J=2.0 Hz, 1H$_{mino}$), 5.83 (s, 1H$_{majo}$), 5.78 (d, J=5.0 Hz, 1H$_{mino}$), 5.70 (d, J=4.5 Hz, 1H$_{majo}$), 4.42-4.87 (m, 20H$_{mino+majo}$), 1.63 (s, 3H$_{majo}$), 1.59 (s, 3H$_{mino}$), 1.52 (s, 3H$_{majo}$), 1.37 (s, 3H$_{mino}$); HRMS (ESI) calcd for (M+Na)$^+$: 617.1782. Found: 617.1798 (+2.5 ppm).

[(2S,3S,4R)-4,5-bis(benzoyloxy)-3-methyltetrahydrofuran-2,3-diyl]dimethanediyl dibenzoate 10

$^1$H NMR (500 MHz, CDCl$_3$) 7.92-8.15 (m, 16H$_{mino+majo}$), 7.34-7.67 (m, 24H$_{mino+majo}$), 6.93 (d, J=5.0 Hz, 1H$_{majo}$), 6.82 (d, J=5.0 Hz, 1H$_{mino}$), 6.66 (d, J=2.0 Hz, 1H$_{mino}$), 6.60 (s, 1H$_{majo}$), 5.98 (s, 1H$_{majo}$), 5.83 (d, J=2.0 Hz, 1H$_{mino}$), 5.80 (d, J=5.8 Hz, 1H$_{mino}$), 5.62 (d, J=5.5 Hz, 1H$_{mino}$), 4.54-4.97 (m, 20H$_{mino+majo}$), 1.64 (s, 3H$_{mino}$), 1.58 (s, 3H$_{majo}$), 1.57 (s, 3H$_{mino}$), 1.48 (s, 3H$_{majo}$); HRMS (ESI) calcd for (M+Na)$^+$: 617.1782. Found: 617.1799 (+2.8 ppm).

EXAMPLE 2

Synthesis of Silylated Nucleobases, Pyrimidine Bases

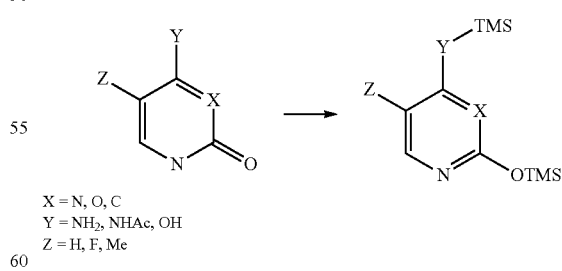

X = N, O, C
Y = NH$_2$, NHAc, OH
Z = H, F, Me

To the glycal (1 equiv) in a THF/$^t$BuOH/H$_2$O solution at room temperature is added sequentially OsO$_4$ (0.03 equiv) and NMO (3 equiv). The reaction is stirred overnight at room temperature before addition of a saturated solution of Na$_2$S$_2$O$_3$ and stirring is continued for 2 h at room tempera- To the free nucleobase (1 equiv) in suspension in CH$_2$Cl$_2$ (1 M) at room temperature is added N,O-Bis(trimethylsilyl)acetamide (3 equiv) and TMSCl (200 µl). Stirring is continued at room temperature until the solution becomes clear. Volatiles are then evaporated under high vacuum overnight.

EXAMPLE 3

Synthesis of Silylated Nucleobases, Purine Bases

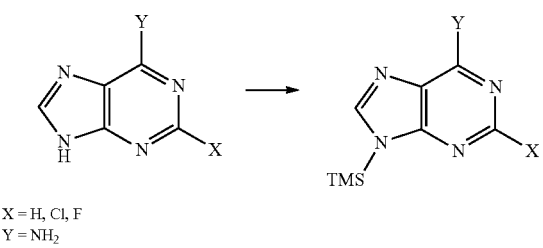

X = H, Cl, F
Y = NH₂

To the free nucleobase (1 equiv) in suspension in CH₂Cl₂ (1 M) at room temperature is added N,O-Bis(trimethylsilyl)acetamide (3 equiv) and TMSCl (200 µl). Stirring is continued at room temperature until the solution becomes clear. Volatiles are then evaporated under high vacuum overnight.

EXAMPLE 4

Synthesis of Nucleosides

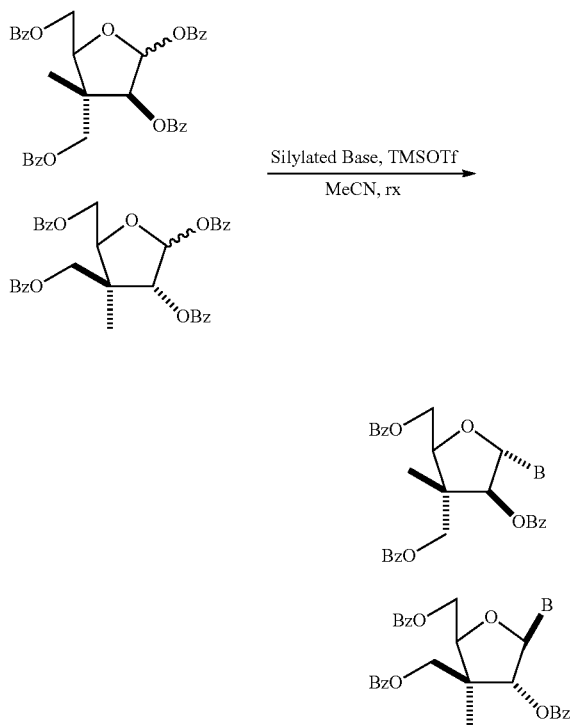

To the neat appropriate silylated nucleobase is added an acetonitrile solution of the appropriate perbenzoylated scaffold at room temperature. To this mixture is added TMSOTf (0.5 equiv) and temperature is raised to reflux for 18 h. After cooling down the reaction, evaporation of volatiles and flash chromatography with the appropriate solvent mixtures.

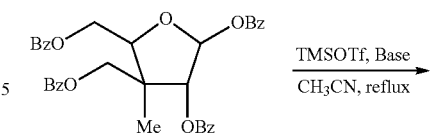

$^1$H NMR (500 MHz, CDCl₃) 8.16 (d, J=6.5 Hz, 1H), 8.08-8.13 (m, 2H), 8.04-8.08 (m, 2H), 7.93-7.99 (m, 2H), 7.62-7.68 (m, 2H), 7.46-7.58 (m, 5H), 7.33-7.39 (m, 2H), 6.16 (d, J=5.0 Hz, 1H), 5.91 (d, J=5.0 Hz, 1H), 4.80-4.94 (m, 1H), 4.76 (dd, J=5.5, 12.0 Hz, 1H), 4.71 (d, J=11.0 Hz, 1H), 4.59 (dd, J=3.5, 5.5 Hz, 1H), 4.50 (d, J=11.0 Hz, 1H), 1.53 (s, 3H); HRMS (ESI) calcd for (M+Na)⁺: 624.1753. Found: 624.1744 (−1.4 ppm)

$^1$H NMR (500 MHz, CDCl₃) 8.11 (d, J=7.5 Hz, 2H), 8.07 (d, J=7.5 Hz, 2H), 7.97 (d, J=7.5 Hz, 2H), 7.83 (d, J=7.5 Hz, 1H), 7.62-7.69 (m, 2H), 7.47-7.59 (m, 5H), 7.34-7.40 (m, 2H), 6.23 (d, J=5.5 Hz, 1H), 5.87 (d, J=6.5 Hz, 1H), 5.77 (d, J=7.5 Hz, 1H), 4.70 (dd, J=5.5 Hz, 1H), 4.66 (d, J=11.5 Hz, 1H), 4.60 (s, 1H), 4.50-4.56 (m, 2H), 1.51 (s, 3H); HRMS (ESI) calcd for (M+H)⁺: 584.2027. Found: 584.2033 (+0.9 ppm).

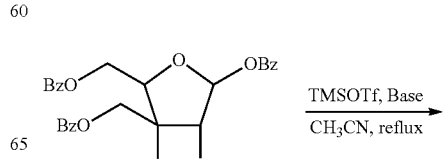

-continued

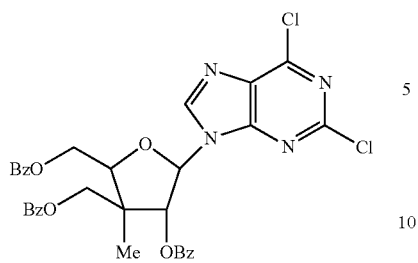

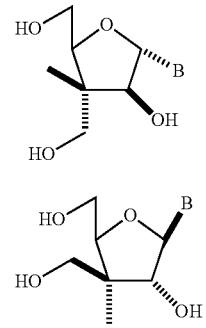

¹H NMR (500 MHz, CDCl₃) 8.34 (s, 1H), 7.88-8.08 (m, 6H), 7.64 (t, J=7.5 Hz, 1H), 7.54-7.62 (m, 2H), 7.43-7.52 (m, 4H), 7.38-7.43 (m, 2H), 6.32 (d, J=6.0 Hz, 1H), 6.29 (d, J=6.0 Hz, 1H), 4.94 (dd, J=3.5, 12.5 Hz, 1H), 4.77 (d, J=11.5 Hz, 1H), 4.68 (d, J=11.5 Hz, 1H), 4.67 (dd, J=6.5, 11.5 Hz, 1H), 4.56 (dd, J=3.0, 6.0 Hz, 1H), 1.60 (s, 3H); HRMS (ESI) calcd for (M+Na)⁺: 683.1071. Found: 683.1072 (+0.1 ppm).

The appropriate protected nucleoside is either deprotected with a methanolic solution of ammonia or with hydrazine in MeOH at room temperature. After completion, the solids are collected and washed to yield the corresponding nucleosides.

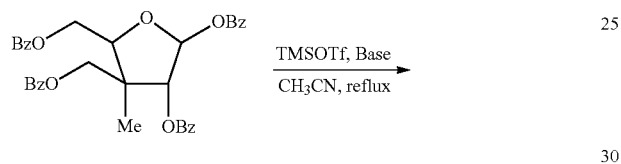

TMSOTf, Base
CH₃CN, reflux

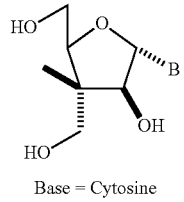

Base = Cytosine 4-amino-1-((2S,3S,4S,5S)-3-hydroxy-4,5-bis(hydroxymethyl)-4-methyltetrahydrofuran-2-yl)pyrimidin-2(1H)-one, LCB-1056

¹H NMR (500 MHz, CD₃OD) δ 8.05 (d, 1H, J=7.5 Hz), 5.92 (d, 1H, J=7.6 Hz), 5.85 (d, 1H, J=5.5 Hz), 4.19 (t, 1H, J=3.9 Hz), 4.13 (d, 1H, J=5.6 Hz), 3.80 (dd, 1H, J=3.5 Hz, J=11.9 Hz), 3.69 (dd, 1H, J=4.9 Hz, J=11.8 Hz), 3.51 (s, 1H), 1.11 (s, 3H); ¹³C NMR (125 MHz, CD₃OD) 166.5, 157.9, 141.9, 94.8, 91.6, 84.4, 82.0, 65.2, 47.2, 15.4; HRMS (ESI) calcd for $C_{11}H_{18}N_3O_5$: 272.1246, found: 272.1243 (1.0 ppm).

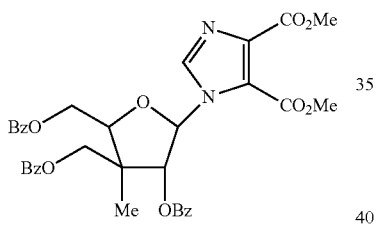

¹H NMR (500 MHz, CDCl₃) 8.04-8.16 (m, 5H), 7.98-8.04 (m, 2H), 7.53-7.68 (m, 3H), 7.44-7.53 (m, 4H), 7.37-7.45 (m, 2H), 6.51 (d, J=4.5 Hz, 1H), 5.90 (d, J=4.0 Hz, 1H), 4.86 (dd, J=3.5, 7.5 Hz, 1H), 4.66 (dd, J=6.5, 12.0 Hz, 1H), 4.50-4.60 (m, 2H), 4.43 (d, J=11.5 Hz, 1H), 3.89 (s, 3H), 3.74 (s, 3H), 1.42 (s, 3H); HRMS (ESI) calcd for (M+Na)⁺: 679.1898. Found: 679.1897 (−0.1 ppm).

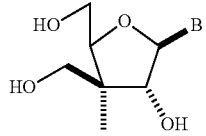

Base = Cytosine 4-amino-1-((2R,3R,4S,5S)-3-hydroxy-4,5-bis(hydroxymethyl)-4-methyltetrahydrofuran-2-yl)pyrimidin-2(1H)-one LCB-1056

¹H NMR (500 MHz, CD₃OD) δ 7.73 (d, 1H, J=7.5 Hz), 5.94 (d, 1H, J=7.7 Hz), 5.80 (d, 1H, J=6.2 Hz), 4.35-4.30 (m, 1H), 4.33 (m, 1H), 4.23 (d, 1H, J=6.2 Hz), 3.75-3.62 (m, 3H), 1.01 (s, 3H); ¹³C NMR (125 MHz, CD₃OD) δ 166.5, 157.9, 141.6, 95.0, 91.6, 84.5, 78.2, 64.9, 61.9, 48.6, 9.6.

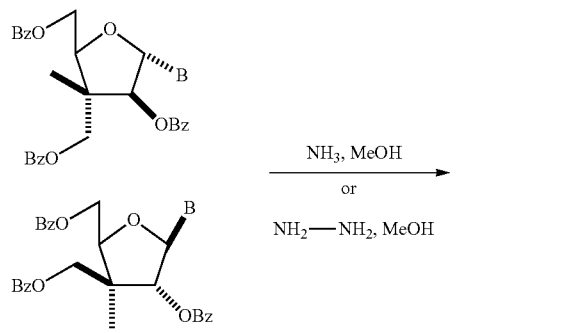

NH₃, MeOH
or
NH₂—NH₂, MeOH

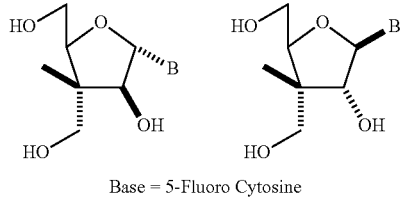

Base = 5-Fluoro Cytosine

LCB-1082

4-amino-5-fluoro-1-((2S,3S,4S,5S)-3-hydroxy-4,5-bis(hydroxymethyl)-4-methyltetrahydrofuran-2-yl)pyrimidin-2(1H)-one; 4-amino-5-fluoro-1-((2R,3R,4S,5S)-3-hydroxy-4,5-bis(hydroxymethyl)-4-methyltetrahydrofuran-2-yl)pyrimidin-2(1H)-one, LCB-1082

$^1$H NMR (500 MHz, CD$_3$OD) δ 7.90 (d, 1H, J=6.6 Hz), 7.75 (d, 1H, J=6.7 Hz), 6.14 (dd, 1H, J=1.6 Hz, J=3.1 Hz), 5.79 (dd, 1H, J=1.1 Hz, J=6.2 Hz), 4.35-4.29 (m, 2H), 4.20 (d, 1H, J=6.2 Hz), 4.11 (d, 1H, J=3.3 Hz), 3.77-3.66 (m, 4H), 3.52 (d, 1H, J=11.5 Hz), 3.50 (d, 1H, J=11.5 Hz), 1.08 (s, 3H), 1.00 (s, 3H); $^{13}$C NMR (125 MHz, CD$_3$OD) δ156.3, 125.7, 125.4, 91.5, 84.6, 84.5, 78.3, 64.8, 63.9, 61.3, 49.6, 48.6, 14.3, 9.0; HRMS (ESI) calcd for C$_{11}$H$_{17}$FN$_3$O$_5$: 290.1152, found: 290.1151 (1.7 ppm).

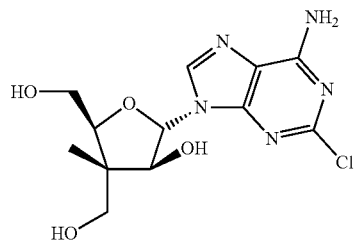

LCB-1091

((2S,3S,4S,5S)-5-(6-amino-2-chloro-9H-purin-9-yl)-4-hydroxy-3-methyltetrahydrofuran-2,3-diyl)dimethanol ((2S,3R,4R,5R)-5-(6-amino-2-chloro-9H-purin-9-yl)-4-hydroxy-3-methyltetrahydrofuran-2,3-diyl)dimethanol LCB-1091

$^1$H NMR (500 MHz, DMSO-d6) δ 8.43 (s, 1H$_{majo}$), 8.40 (s, 1H$_{mino}$), 7.90-7.80 (m, 2H), 5.84 (d, 1H$_{majo}$, J=7.4 Hz), 5.73 (d, 1H$_{mino}$, J=7.0 Hz), 5.60-5.50 (m, 1H$_{majo+mino}$); 5.19-5.13 (m, 1H$_{majo}$), 4.96-4.91 (m, 1H$_{mino}$), 4.86-4.77 (m, 1H$_{majo}$), 4.73-4.67 (m, 1H$_{mino}$), 4.50-4.45 (m, 1H$_{majo}$), 4.36 (dd, 1H$_{mino}$, J=4.6 Hz, J=7.0 Hz), 4.12-4.09 (m, 1H$_{majo+mino}$), 3.69-3.63 (m, 1Hmajo+mino), 3.62-3.49 (m, 2H$_{majo+mino}$), 3.47-3.41 (m, 1H$_{majo+mino}$), 1.08 (s, 3H$_{majo}$), 0.90 (s, 3H$_{mino}$) HRMS (ESI) calcd for C$_{12}$H$_{17}$ClN$_5$O$_4$: 290.1152, found: 330.0970 (2.1 ppm).

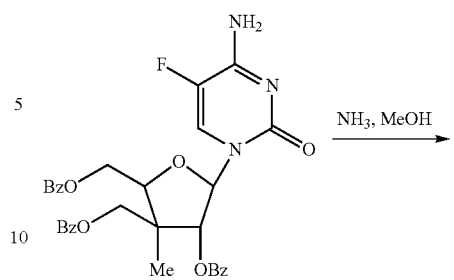

LCB-1096

4-amino-5-fluoro-1-((2R,3R,4S,5S)-3-hydroxy-4,5-bis(hydroxymethyl)-4-methyltetrahydrofuran-2-yl)pyrimidin-2(1H)-one, LCB-1096

$^1$H NMR (500 MHz, MeOD) 8.32 (d, J=6.0 Hz, 1H), 5.88 (d, J=6.0 Hz, 1H), 4.17 (d, J=6.0 Hz, 1H), 3.91 (d, J=4.1 Hz, 1H), 3.80-3.88 (m, 2H), 3.68 (d, J=11.0 Hz, 1H), 3.54 (d, J=11.0 Hz, 1H), 1.17 (s, 3H); HRMS (ESI) calcd for (M+H)$^+$: 290.1147. Found: 290.1153 (+2.2 ppm).

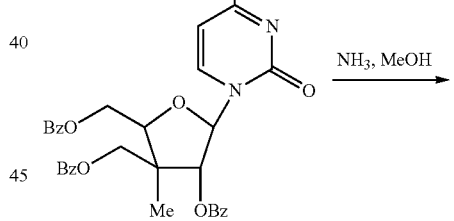

LCB-1095

4-amino-1-((2R,3R,4S,5S)-3-hydroxy-4,5-bis(hydroxymethyl)-4-methyltetrahydrofuran-2-yl)pyrimidin-2(1H)-one LCB-1095

$^1$H NMR (500 MHz, MeOD) 8.06 (d, J=7.0 Hz, 1H), 5.92 (d, J=7.5 Hz, 1H), 5.86 (d, J=6.0 Hz, 1H), 4.18 (d, J=4.5 Hz, 1H), 3.91 (t, J=4.0 Hz, 1H), 3.78-3.86 (m, 2H), 5.92 (d,

J=11.0 Hz, 1H), 5.86 (d, J=11.5 Hz, 1H), 1.18 (s, 3H); HRMS (ESI) calcd for (M+Na)+: 294.1060. Found: 294.1049 (−4.1 ppm).

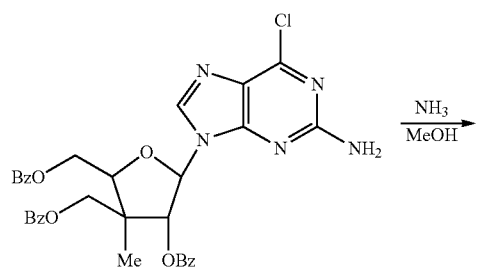

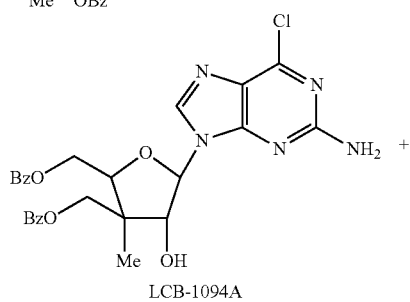

LCB-1094A

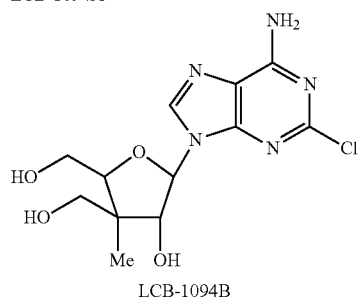

LCB-1094B ((2S,3S,4R,5R)-5-(2-amino-6-chloro-9H-purin-9-yl)-4-hydroxy-3-methyltetrahydrofuran-2,3-diyl)dimethanol (A), ((2S,3S,4R,5R)-5-(6-amino-2-chloro-9H-purin-9-yl)-4-hydroxy-3-methyltetrahydrofuran-2,3-diyl)dimethanol (B)

$^1$H NMR (500 MHz, DMSO) 8.70 (s, 1H$_{mino}$), 8.41 (s, 1H$_{majo}$), 7.82-7.89 (m, 4H$_{majo+mino}$), 5.84 (d, J=7.0 Hz, 1H$_{mino}$), 5.74 (d, J=7.5 Hz, 1H$_{majo}$), 5.46 (d, J=5.5 Hz, 1H$_{majo}$), 5.42 (d, J=6.0 Hz, 1H$_{mino}$), 5.10 (t, J=5.0 Hz, 1H$_{majo}$), 5.04 J=5.0 Hz, 1H$_{mino}$), 4.72-4.75 (m, 2H$_{mino+majo}$), 4.46-4.54 (m, 2H$_{mino+majo}$) 4.10 (m, 2H), 3.83 (m, 1H$_{mino}$), 3.79 (m, 1H$_{majo}$), 3.62-3.77 (m, 4H$_{mino+majo}$) 1.14 (s, 3H$_{mino}$), 1.12 (s, 3H$_{majo}$); HRMS (ESI) calcd for (M+Na)+: 352.0783. Found: 352.0784 (+0.3 ppm)

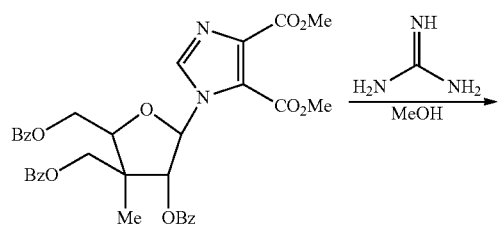

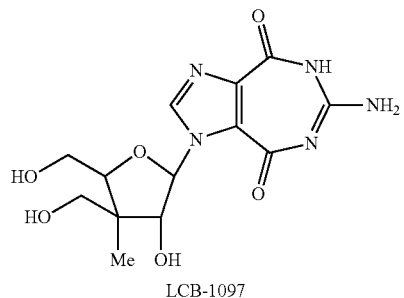

LCB-1097

6-amino-1-((2R,3R,4S,5S)-3-hydroxy-4,5-bis(hydroxymethyl)-4-methyltetrahydrofuran-2-yl)imidazo[4,5-e][1,3]diazepine-4,8(1H,5H)-dione LCB-1097

$^1$H NMR (500 MHz, MeOD) 8.36 (d, J=3.5 Hz, 1H), 6.44 (t, J=4.5 Hz, 1H), 4.20 (t, J=3.5 Hz, 1H), 4.01 (d, J=4.2 Hz, 1H), 3.84-3.91 (m, 2H), 3.60 (d, J=11.0 Hz, 1H), 3.46 (d, J=11.0 Hz, 1H), 1.19 (s, 3H); HRMS (ESI) calcd for (M+Na)+: 362.1071. Found: 362.1077 (+1.63 ppm).

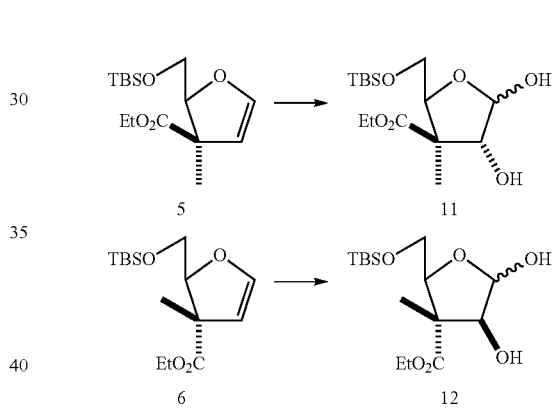

To the glycal (1 equiv) in a THF/$^t$BuOH/H$_2$O solution at room temperature is added sequentially OsO$_4$ (0.03 equiv) and NMO (3 equiv). The reaction is stirred overnight at room temperature before addition of a saturated solution of Na$_2$S$_2$O$_3$ and stirring is continued for 2 h at room temperature. Evaporation of volatiles, extraction with Et$_2$O (×4) and drying on MgSO$_4$. After evaporation of volatiles, the residue is used without any purification yielding the diol as a mix of anomers (82%).

(±) (2S,3S,4S)-ethyl 2-((tert-butyldimethylsilyloxy)methyl)-4,5-dihydroxy-3-methyltetrahydrofuran-3-carboxylate 11: HRMS (ESI) calcd for C$_{15}$H$_{30}$NaO$_6$Si: 357.1709, found: 357.1704 (0.2 ppm).

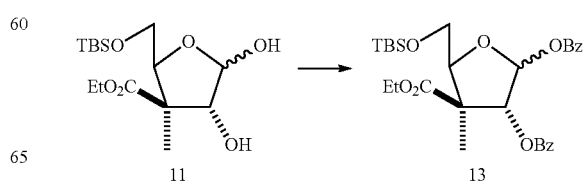

-continued

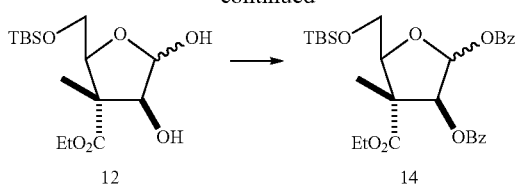

To a solution of the diol (1 equiv) in pyridine (1 M) at 0° C. is added BzCl (2.4 equiv). Stirring overnight at room temperature then evaporation of pyridine. The residue is dissolved in Hexanes and rapidly percolated through a pad of silica gel (Hex/AcOEt 20:80) to yield the corresponding perbenzoylated compound as a mix of anomers (quant.).

(±) (3R,4S,5S)-5-((tert-butyldimethylsilyloxy)methyl)-4-(ethoxycarbonyl)-4-methyltetrahydrofuran-2,3-diyl dibenzoate 13

$^1$H NMR (500 MHz, CDCl$_3$) δ 8.17 (m, 2H$_{mino}$), 8.09 (m, 2H$_{mino}$), 7.99 (m, 4H$_{majo}$), 7.71 (m, 1H), 7.58 (m, 5H$_{majo+mino}$), 7.47 (m, 2H$_{majo}$), 7.39 (m, 4H$_{majo}$), 6.82 (d, 1H$_{majo}$, J=5.0 Hz), 6.49 (d, 1H$_{mino}$, J=3.9 Hz), 6.40 (d, 1H$_{mino}$, J=3.9 Hz), 6.11 (d, 1H$_{majo}$, J=5.0 Hz), 4.33 (t, 1H$_{majo}$, J=3.3 Hz), 4.26 (t, 1H$_{mino}$, J=3.9 Hz), 4.20 (m, 4H$_{majo}$), 3.95 (m, 3H$_{mino}$), 3.81 (dd, 1H$_{mino}$, J=3.4 Hz, J=11.1 Hz), 1.76 (s, 3H$_{majo}$), 1.65 (s, 3H$_{mino}$), 1.28 (t, 3H$_{majo}$, J=7.1 Hz), 1.22 (t, 3H$_{majo}$, J=7.1 Hz), 0.94 (s, 9H$_{majo}$), 0.92 (s, 9H$_{mino}$), 0.13 (s, 3H$_{majo}$), 0.09 (s, 3H$_{majo}$), 0.07 (s, 3H$_{mino}$), 0.04 (s, 3H$_{mino}$); HRMS (ESI) calcd for C$_{29}$H$_{38}$NaO$_8$Si: 565.2234, found: 565.2231 (0.5 ppm).

(±) (3S,4R,5S)-5-((tert-butyldimethylsilyloxy)methyl)-4-(ethoxycarbonyl)-4-methyltetrahydrofuran-2,3-diyl dibenzoate 14

$^1$H NMR (500 MHz, CDCl$_3$) δ 8.19 (dd, 2H, J=1.3 Hz, J=8.4 Hz), 8.07 (dd, 2H, J=1.2 Hz, J=8.3 Hz), 8.03 (dd, 2H, J=1.3 Hz, J=8.3 Hz), 7.98 (dd, 2H, J=1.3 Hz, J=8.3 Hz), 7.89 (dd, 2H, J=1.3 Hz, J=8.3 Hz), 7.70 (m, 1H), 7.64-7.59 (m, 1H), 7.58-7.53 (m, 1H), 7.51-7.46 (m, 3H), 7.42-7.38 (m, 2H), 7.30-7.26 (m, 2H), 6.76 (d, 1H, J=4.5 Hz), 6.56 (d, 1H, J=2.5 Hz), 6.45 (s, 1H), 6.06 (d, 1H, J=2.5 Hz), 5.60 (s, 1H), 5.59 (d, 1H, J=4.5 Hz), 5.10 (t, 1H, J=5.3 Hz), 5.01 (t, 1H, J=5.9 Hz), 4.13 (dq, 2H, J=1.7 Hz, J=7.2 Hz), 4.09 (q, 2H, J=7.2 Hz), 3.96-3.85 (m, 4H), 1.69 (s, 3H), 1.62 (s, 3H), 1.54 (s, 3H), 1.15-1.10 (m, 6H), 0.92 (s, 9H), 0.89 (s, 9H), 0.13 (s, 3H), 0.11 (s, 3H), 0.09 (s, 3H), 0.08 (s, 3H); $^{13}$C NMR (125 MHz, CDCl$_3$) δ 171.3, 171.2, 165.2, 165.2, 165.0, 164.9, 134.8, 133.9, 133.7, 133.7, 133.4, 130.8, 130.2, 130.1, 130.0, 130.0, 130.0, 129.8, 129.7, 129.3, 129.2, 129.1, 128.8, 128.7, 128.7, 128.4, 100.2, 95.0, 84.4, 83.8, 82.6, 79.7, 62.8, 62.2, 61.6, 61.5, 53.2, 53.0, 26.0, 26.0, 25.9, 25.9, 18.5, 18.4, 17.0, 15.9, 14.2, 14.2, −5.2, −5.2, −5.3, −5.3; HRMS (ESI) calcd for C$_{29}$H$_{38}$NaO$_8$Si: 565.2234, found: 565.2215 (−2.2 ppm).

EXAMPLE 5

Synthesis of Silylated Nucleobases, Pyrimidine Bases

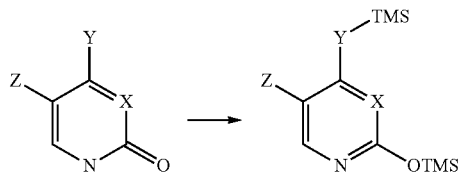

X = N, O, C
Y = NH$_2$, NHAc, OH
Z = H, F, Me

To the free nucleobase (1 equiv) in suspension in CH$_2$Cl$_2$ (1 M) at room temperature is added N,O-Bis(trimethylsilyl)acetamide (3 equiv) and TMSCl (200 µl). Stirring is continued at room temperature until the solution becomes clear. Volatiles are then evaporated under high vacuum overnight.

EXAMPLE 6

Synthesis of Silylated Nucleobases, Purine Bases

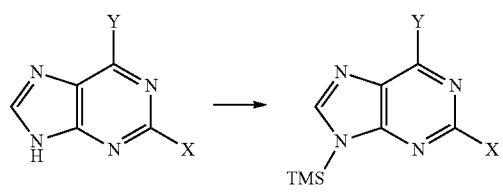

X = H, Cl, F
Y = NH$_2$

To the free nucleobase (1 equiv) in suspension in CH$_2$Cl$_2$ (1 M) at room temperature is added N,O-Bis(trimethylsilyl)acetamide (3 equiv) and TMSCl (200 µl). Stirring is continued at room temperature until the solution becomes clear. Volatiles are then evaporated under high vacuum overnight.

EXAMPLE 7

Synthesis of Nucleosides

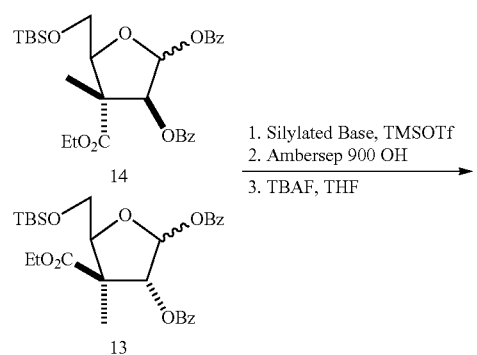

1. Silylated Base, TMSOTf
2. Ambersep 900 OH
3. TBAF, THF

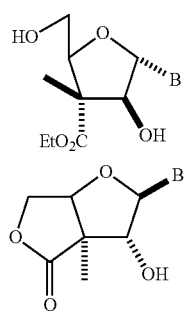

To the neat appropriate silylated nucleobase is added an acetonitrile solution of the appropriate perbenzoylated scaffold at room temperature. To this mixture is added TMSOTf (0.5 equiv) and temperature is raised to reflux for 18 h. After cooling down and evaporation of volatiles, the residue is dissolved in MeOH and Ambersep 900 (OH) resin is added. Stirring is continued until completion of reaction (TLC). After filtration and evaporation of solvents, the residue is dissolved in THF at room temperature and a 1M solution of TBAF (1M, 1.5 equiv). Stirring is continued at room temperature overnight then volatiles are evaporated and the residue is purified by flash chromatography with the appropriate solvent mixtures to yield the corresponding monocyclic or bicyclic nucleoside.

LCB-1079

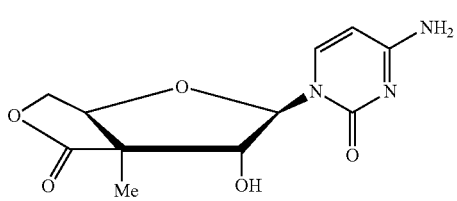

(±) 4-amino-1-((2R,3R,3αR,6αS)-3-hydroxy-3α-methyl-4-oxohexahydrofuro[3,4-β]furan-2-yl)pyrimidin-2(1H)-one: LCB-1079

$^1$H NMR (500 MHz, CD$_3$OD) δ 7.47 (d, 1H, J=7.5 Hz), 5.88 (d, 1H, J=7.5 Hz), 5.72 (d, 1H, J=1.7 Hz), 4.72 (d, 1H, J=3.0 Hz), 4.65 (d, 1H, J=11.3 Hz), 4.53 (dd, 1H, J=3.1 Hz, J=11.3 Hz), 4.43 (d, 1H, J=1.4 Hz), 1.34 (s, 3H); HRMS (ESI) calcd for C$_{11}$H$_{14}$N$_3$O$_5$: 268.0933, found: 268.0930 (1.0 ppm).

LCB-1080

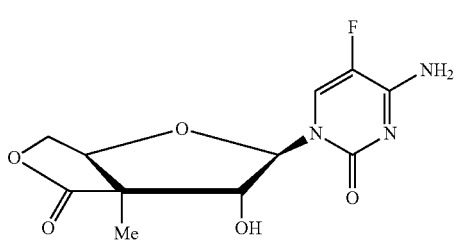

(±) 4-amino-5-fluoro-1-((2R,3R,3αR,6αS)-3-hydroxy-3α-methyl-4-oxohexahydrofuro[3,4-β]furan-2-yl)pyrimidin-2(1H)-one: LCB-1080

$^1$H NMR (500 MHz, CD$_3$OD) δ 7.57 (d, 1H, J=6.6 Hz), 5.66 (s, 1H), 4.76-4.70 (m, 2H), 4.54 (dd, 1H, J=3.0 Hz, J=11.5 Hz), 4.46 (s, 1H), 1.35 (s, 1H); HRMS (ESI) calcd for C$_{11}$H$_{13}$FN$_3$O$_5$: 286.0839, found: 286.0826 (−2.6 ppm).

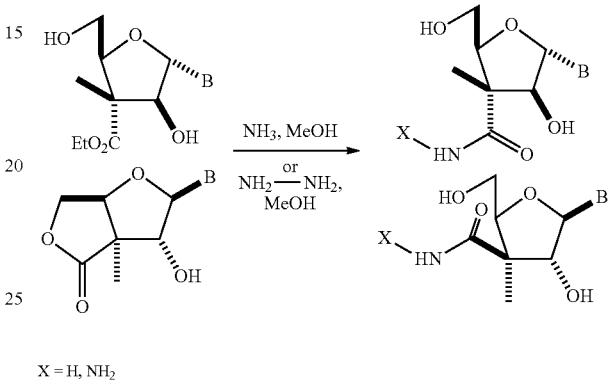

X = H, NH$_2$

The appropriate protected nucleoside is either deprotected with a methanolic solution of ammonia or with hydrazine in MeOH at room temperature. After completion, the solids are collected and washed with MeOH to yield the corresponding nucleoside.

LCB-1085

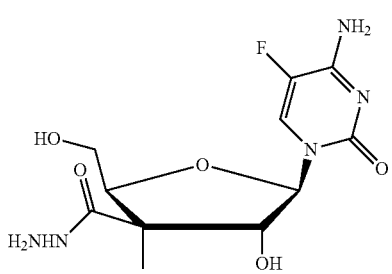

(2S,3R,4R,5R)-5-(4-amino-5-fluoro-2-oxopyrimidin-1(2H)-yl)-4-hydroxy-2-(hydroxymethyl)-3-methyltetrahydrofuran-3-carbohydrazide: LCB-1085

$^1$H NMR (500 MHz, DMSO-d6) δ 8.86 (bs, 1H), 8.40 (d, 1H, J=7.3 Hz), 7.85 (bs, 1H), 7.61 (bs, 1H), 5.80 (d, 1H, J=4.9 Hz), 5.53 (d, 1H, J=6.0 Hz), 4.95 (t, 1H, J=5.1 Hz), 4.49 (t, 1H, J=6.0 Hz), 4.31 (bs, 1H), 3.72 (t, 1H, J=4.2 Hz), 3.48 (t, 2H, J=4.6 Hz), 1.22 (s, 3H); $^{13}$C NMR (125 MHz, DMSO-d6) δ173.3, 158.1, 158.0, 137.9, 135.9, 127.3, 127.0, 89.8, 87.4, 77.8, 62.0, 17.2; HRMS (ESI) calcd for C$_{11}$H$_{17}$FN$_5$O$_5$: 318.1202, found: 318.1214 (−1.8 ppm).

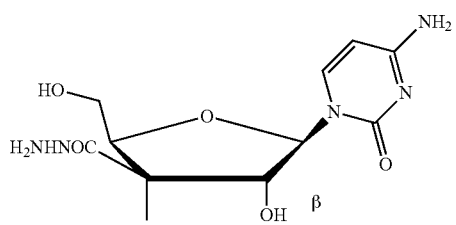

LCB-1077

(2S,3R,4R,5R)-5-(4-amino-2-oxopyrimidin-1(2H)-yl)-4-hydroxy-2-(hydroxymethyl)-3-methyltetrahydrofuran-3-carbohydrazide: LCB-1077

$^1$H NMR (500 MHz, CD$_3$OD) δ 8.13 (d, 1H, J=7.6 Hz), 5.94 (d, 1H, J=6.3 Hz), 5.94 (d, 1H, J=7.3 Hz), 4.73 (d, 1H, J=6.4 Hz), 4.00-3.96 (m, 1H), 3.80 (dd, 1H, J=4.8 Hz, J=12.1 Hz), 3.68 (dd, 1H, J=3.1 Hz, J=11.9 Hz), 1.43 (s, 3H); HRMS (ESI) calcd for C$_{11}$H$_{17}$N$_5$O$_5$: 300.1308, found: 300.1297 (−1.5 ppm).

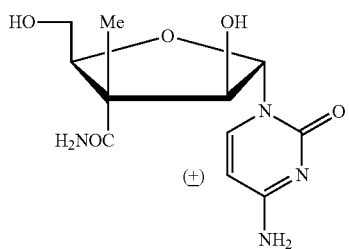

LCB-1087

(2S,3S,4S,5S)-5-(4-amino-2-oxopyrimidin-1(2H)-yl)-4-hydroxy-2-(hydroxymethyl)-3-methyltetrahydrofuran-3-carboxamide: LCB-1087

$^1$H NMR (500 MHz, CD$_3$OD) δ 8.07 (d, 1H, J=7.5 Hz), 5.93 (d, 1H, J=7.5 Hz), 5.82 (d, 1H, J=5.3 Hz), 4.64 (t, 1H, J=3.9 Hz), 4.34 (d, 1H, J=5.3 Hz), 3.89 (dd, 1H, J=3.5 Hz, J=12.0 Hz), 3.77 (dd, 1H, J=3.6 Hz, J=11.4 Hz), 1.34 (s, 3H); HRMS (ESI) calcd for C$_{11}$H$_{17}$N$_4$O$_5$: 285.1199, found: 285.1200 (2.5 ppm).

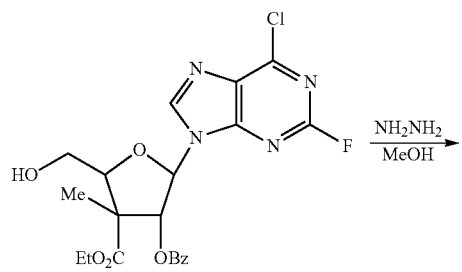

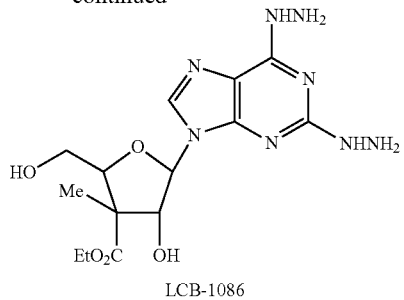

LCB-1086

(±) (2S,3R,4R,5R)-ethyl 5-(2-fluoro-6-hydrazinyl-9H-purin-9-yl)-4-hydroxy-2-(hydroxymethyl)-3-methyltetrahydrofuran-3-carboxylate LCB-1086: $^1$H NMR (500 MHz, DMSO) 8.62-8.71 (m, 1H), 7.94-8.00 (m, 1H), 7.34-7.44 (m, 1H), 5.96-6.04 (m, 1H), 5.80-5.88 (m, 1H), 5.38-5.48 (m, 1H), 4.56-4.64 (m, 1H), 4.40-4.56 (m, 1H), 4.26-4.33 (m, 1H), 4.16-4.21 (m, 2H), 3.61-3.68 (m, 1H), 3.50-3.58 (m, 1H), 1.40 (s, 3H), 1.25 (t, J=7.0 Hz, 3H) ppm. HRMS (ESI) calcd for C$_{14}$H$_{23}$N$_8$O$_5$ (M+H): 383.1791, found: 383.1792 (1.6 ppm)

EXAMPLE 8

Biological Assay, MTT Cell Proliferation Assay

The antiviral and antitumor activities of the compounds of the invention were evaluated by a cellular proliferation assay. The MTT [3-(4,5-dimethylthiazol-2-yl)-2,5-diphenyltetrazolium bromide] assay, first described by Mosmann (Mosmann T., "Rapid colorimetric assay for cellular growth and survival: application to proliferation and cytotoxicity assays," J. Immunol. Methods 1983 Dec. 16; 65(1-2):55-63, and incorporated by reference in its entirety) is based on the ability of a mitochondrial dehydrogenase enzyme from viable cells to cleave the tetrazolium rings of the pale yellow MTT. The cleavage reaction form a dark blue formazan crystals which is largely impermeable to cell membranes and accumulation within healthy cells. Solubilisation of the cells by the addition of a detergent liberates and solubilizes the crystals. The number of surviving cells is directly proportional to the level of the formazan product created. The color can then be quantified using a simple colorimetric assay. The results can be read on a multiwell scanning spectrophotometer (ELISA reader).

In Tables 1 and 2, IC$_{50}$ values are presented for various cell lines in micromolar units (μm), "Gemci" is Gemcitabine, and "5-FU" is 5-fluorouracil.

| Cell Line | Physiological Origin |
|---|---|
| 1A6 | Urinary bladder |
| 22 Rv1 | Prostate |
| 786-O | Kidney |
| BxPC-3 | Pancreas |
| Colo 829 | Skin |
| DLD-1 | Colon |
| HCC 143 | Mammary gland; breast |
| HCT 116 | Colon |
| HL-60 | Acute promyelocytic leukemia |
| MCF7 | Mammary gland; breast |
| MOLT-4 | Acute lymphoblastic leukemia |
| NCI H1395 | Lung |
| NCI H2052 | Tumor stage 4 derived from pleural effusion |
| OVCAR3 | Ovary |

-continued
| Cell Line | Physiological Origin |
|---|---|
| PFSK-1 | Brain |
| ZR-75-1 | Mammary gland; breast |
TABLE 1
|  | 1A6 | 22Rv1 | 786-O | BxPC-3 | Colo 829 | DLD-1 | HCC1143 | HCT 116 |
|---|---|---|---|---|---|---|---|---|
| 5-FU | 300 | 50 | 110 | 220 | 170 | 470 | 340 | 25 |
| Gemci. | 5 | >500 | >500 | <0.5 | <0.5 | >500 | 400 | <0.5 |
| 1056 | >500 | n/a | >500 | >500 | >500 | >500 | >500 | >500 |
| 1077 | 480 | >500 | 150 | >500 | 320 | 480 | >500 | >500 |
| 1077 | 450 | n/a | 80 | >500 | n/a | >500 | 460 | >500 |
| 1079 | 350 | n/a | 460 | 160 | n/a | 440 | 480 | 410 |
| 1080 | >500 | n/a | >500 | n/a | >500 | >500 | >500 | n/a |
| 1082 | >500 | n/a | >500 | n/a | >500 | >500 | >500 | n/a |
| 1085 | >100 | >100 | >100 | >100 | >100 | >100 | >100 | >100 |
| 1086 | >100 | >100 | >100 | 90 | >100 | >100 | >100 | >100 |
| 1087 | >500 | >500 | >500 | >500 | >500 | >500 | >500 | >500 |
| 1091 | >500 | >500 | >500 | >500 | >500 | >500 | >500 | >500 |
| 1094 | >500 | >500 | >500 | >500 | >500 | >500 | >500 | >500 |
| 1095 | >500 | >500 | >500 | >500 | 460 | >500 | >500 | >500 |
| 1096 | >500 | >500 | >500 | >500 | >500 | >500 | >500 | >500 |
| 1097 | >500 | >500 | >500 | >500 | >500 | >500 | >500 | >500 |
TABLE 2
|  | HL-60 | MCF7 | MOLT-4 | NCI H1395 | NCI H2052 | OVCAR3 | PFSK-1 | ZR-75-1 |
|---|---|---|---|---|---|---|---|---|
| 5-FU | 25 | 40 | 20 | >500 | >500 | 35 | 460 | >500 |
| Gemci. | <0.5 | >500 | <0.5 | <0.5 | >500 | 5 | >500 | >500 |
| 1056 | >500 | >500 | 110 | 440 | >500 | >500 | >500 | >500 |
| 1056 | >500 | >500 | 440 | >500 | >500 | >500 | >500 | >500 |
| 1056 | >500 | >500 | 440 | >500 | >500 | >500 | >500 | >500 |
| 1077 | 360 | >500 | >500 | >500 | n/a | 420 | >500 | 460 |
| 1077 | >500 | >500 | >500 | >500 | >500 | >500 | >500 | >500 |
| 1079 | 250 | 280 | 260 | >500 | 310 | 280 | 130 | 380 |
| 1080 | >500 | >500 | >500 | >500 | >500 | n/a | >500 | >500 |
| 1082 | >500 | >500 | >500 | >500 | >500 | n/a | >500 | >500 |
| 1085 | >100 | >100 | 80 | >100 | >100 | >100 | >100 | >100 |
| 1086 | >100 | >100 | >100 | >100 | n/a | >100 | 98 | >100 |
| 1087 | >500 | >500 | >500 | >500 | n/a | >500 | >500 | >500 |
| 1090 | >100 | >100 | >100 | >100 | >100 | >100 | >100 | >100 |
| 1090 | >100 | >100 | >100 | 95 | >100 | >100 | >100 | >100 |
| 1091 | >500 | >500 | >500 | >500 | >500 | >500 | >500 | >500 |
| 1094 | >500 | >500 | >500 | >500 | >500 | >500 | >500 | >500 |
| 1095 | >500 | 430 | >500 | >500 | >500 | >500 | >500 | >500 |
| 1096 | >500 | >500 | >500 | >500 | >500 | >500 | >500 | >500 |
| 1097 | >500 | >500 | >500 | >500 | >500 | >500 | >500 | 210 |
What is claimed is:
1. A compound of the formula
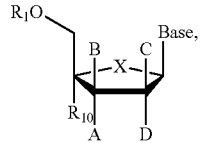
I
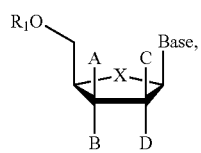
II
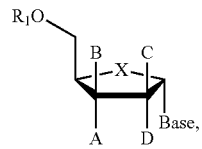
III
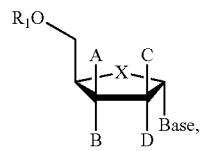
IV

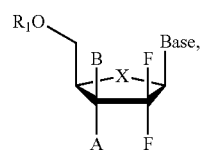 I-F
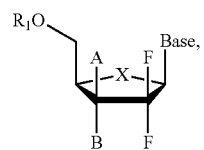 II-F
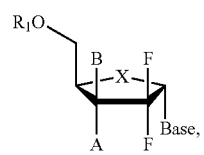 III-F
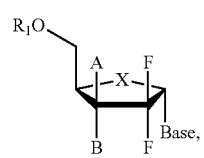 IV-F
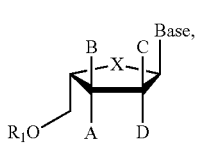 V
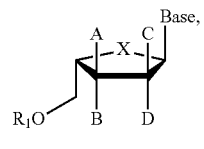 VI
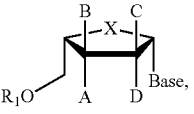 VII
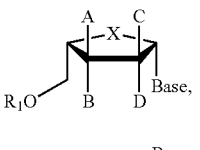 VIII
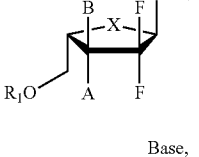 V-F
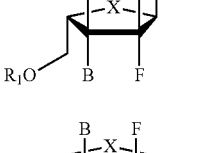 VI-F
 VII-F
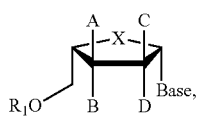 VIII-F
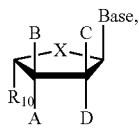 IX
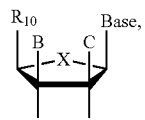 X
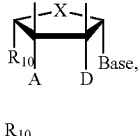 XI
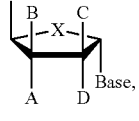 XII
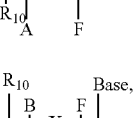 IX-F
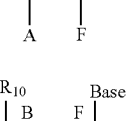 X-F
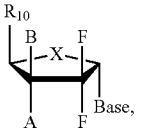 XI-F
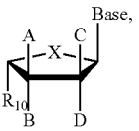 XII-F
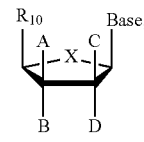 XIII
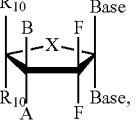 XIV -continued XV 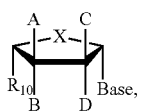

XVI 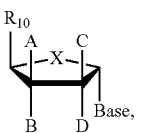

XIII-F 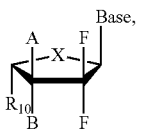

XIV-F 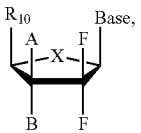

XV-F 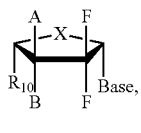

XVI-F 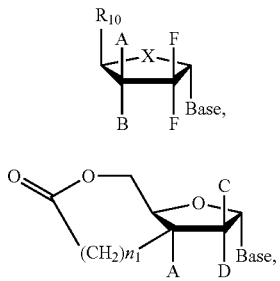

XVII 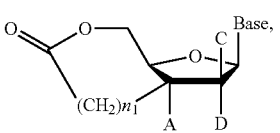

XVIII 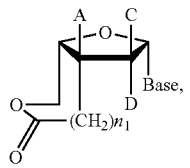

XIX 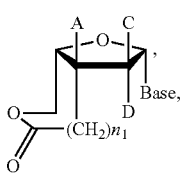

XX 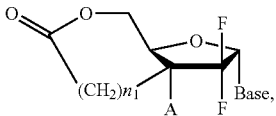

XVII-F

XVIII-F 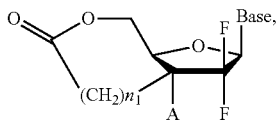

XIX-F 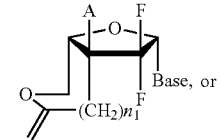

XX-F 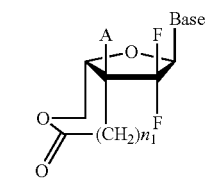

or a pharmaceutically acceptable salts thereof, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —$C(O)$—$NR_4R_{4a}$, —$C(O)OR_2$, —$(CH_2)n_1C(O)OR_2$, —$C(O)$—$R_3$, or —$(CH_2)_nM$, with the proviso that when A is $CH_3$ or $CF_3$, B cannot be $CH_3$;

M is —$OR_1$, halo, mono- to per-halo $C_1$-$C_6$ alkyl, —$SR_1$, aryl, —$CO_2R_2$, —$COR_3$, heterocyclyl, heteroaryl, —$NH(CO)R_5$, —$NR_6R_{6a}$, —$CONR_4R_{4a}$, —$NHSO_2R_7$, —$CO$—$CH_2OH$, —$SOR_8$, —$SO_2NR_5R_{5a}$, —$O(CO)R_3$, —$N_3$, or $C_2$-$C_6$ alkynyl, wherein each of the alkyl, heterocyclyl, aryl, and heteroaryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl;

n is 1 to 3;

$n_1$ is 0 to 3;

$R_1$ is —H, —$CH_2$—$P(O)(OH)_2$, —$P(O)(OH)_2$, —$P(O)(OR_2)_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl;

$R_2$ is —H, aryl, —$C_1$-$C_6$ alkylaryl, or $C_1$-$C_6$ alkyl;

$R_3$ is —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_2$, —$C_1$-$C_6$ alkyl-$C(O)OR_2$, $C_1$-$C_6$ alkoxy, and mono- to per-halo $C_1$-$C_6$ alkyl;

$R_4$ and $R_{4a}$ are independently —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl; or $R_4$ and $R_{4a}$ together with the nitrogen to which they are attached form -$(AA)_x$-, wherein x is 1 to 5, and AA is a natural, non-natural, D- or L-amino acid, wherein -$(AA)_x$ is terminated by a protected or unprotected carboxyl group;

$R_5$ and $R_{5a}$ are independently —H, aryl, $C_1$-$C_6$ alkylaryl, $C_1$-$C_6$ alkyl, or $C_1$-$C_6$ alkoxy;

$R_6$ and $R_{6a}$ are independently —H, aryl, $C_1$-$C_6$ alkylaryl, or $C_1$-$C_6$ alkyl;

$R_7$ is $C_1$-$C_6$ alkyl, aryl, $C_1$-$C_6$ alkylaryl, or mono- to per-halo $C_1$-$C_6$ alkyl;

$R_8$ is $C_1$-$C_6$ alkyl, aryl, $C_1$-$C_6$ alkylaryl, or mono- to per-halo $C_1$-$C_6$ alkyl;

$R_9$ is H or $C_1$-$C_6$ alkyl;

C and D are independently —H, halo, azido, —$OR_2$, CN, $CF_3$, —$(CH_2)nCO_2R_9$, $C(O)NR_4R_{4a}$, or —$CONR_6R_{6a}$, with the proviso that C and D cannot simultaneously be —OH;

X is O or S;

$R_{10}$ is —$C(O)OR_3$, —$CH_2$—$C(O)OR_3$, —$CONH_2$, —$CONHR_6$, —$CONHNH_2$, —$CONHNHR_6$, —$CONR_4R_{4a}$, —$CONR_6R_{6a}$, —$CH_2$—$P(O)(OH)_2$, —$P(O)(OH)_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl;

and Base is a purine derivative or a pyrimidine derivative.

2. The compound of claim 1, wherein at least one of C and D is —H.

3. The compound of claim 1, wherein one of C and D is —H and the other is fluoro, azido, —$NR_4R_{4a}$, or $OR_2$.

4. The compound of claim 1, wherein

A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —$C(O)$—$NR_4R_{4a}$, —$C(O)OR_2$, —$(CH_2)n_1C(O)OR_2$, —$C(O)$—$R_3$, or —$(CH_2)_nM$;

M is —$OR_1$, halo, mono- to per-halo $C_1$-$C_6$ alkyl, —$SR_1$, aryl, —$CO_2R_2$, —$COR_3$, heterocyclyl, heteroaryl, —$NH(CO)R_5$, —$NR_6R_{6a}$, —$CONR_4R_{4a}$, —$NHSO_2R_7$, —$CO$—$CH_2OH$, —$SOR_8$, —$SO_2NR_5R_{5a}$, —$O(CO)R_3$, —$N_3$, or $C_2$-$C_6$ alkynyl, wherein each of the alkyl, heterocyclyl, aryl and heteroaryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl;

n is 1 to 3;

$n_1$ is 0 to 3;

$R_1$ is —H, —$CH_2$—$P(O)(OH)_2$, —$P(O)(OH)_2$, —$P(O)(OR_2)_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl;

$R_2$ is —H, aryl, —$C_1$-$C_6$ alkylaryl, or $C_1$-$C_6$ alkyl;

$R_3$ is —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_2$, —$C_1$-$C_6$ alkyl-$C(O)OR_2$, $C_1$-$C_6$ alkoxy, and mono- to per-halo $C_1$-$C_6$ alkyl;

$R_4$ and $R_{4a}$ are independently —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl; or $R_4$ and $R_{4a}$ together with the nitrogen to which they are attached form -$(AA)_x$-, wherein x is 1 to 5, and AA is a natural, non-natural, D- or L-amino acid, wherein -$(AA)_x$ is terminated by a protected or unprotected carboxyl group:

$R_5$ and $R_{5a}$ are independently —H, aryl, $C_1$-$C_6$ alkylaryl, $C_1$-$C_6$ alkyl, or $C_1$-$C_6$ alkoxy;

$R_6$ and $R_{6a}$ are independently —H, aryl, $C_1$-$C_6$ alkylaryl, or $C_1$-$C_6$ alkyl;

$R_7$ is $C_1$-$C_6$ alkyl, aryl, $C_1$-$C_6$ alkylaryl, or mono- to per-halo $C_1$-$C_6$ alkyl;

$R_8$ is $C_1$-$C_6$ alkyl, aryl, $C_1$-$C_6$ alkylaryl, or mono- to per-halo $C_1$-$C_6$ alkyl;

$R_9$ is H or $C_1$-$C_6$ alkyl;

C and D are independently —H, halo, azido, —$OR_2$, —CN, —$CF_3$, —$(CH_2)nCO_2R_9$, —$C(O)NR_4R_{4a}$, or —$CONR_6R_{6a}$ X is O or S;

$R_{10}$ is —$C(O)OR_3$, —$CH_2$—$C(O)OR_3$, —$CONH_2$, —$CONHR_6$, —$CONHNH_2$, —$CONHNHR_6$, —$CONR_4R_{4a}$, —$CONR_6R_{6a}$, —$CH_2$—$P(O)(OH)_2$, —$P(O)(OH)_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —$C(O)OR_3$, —$C_1$-$C_6$ alkyl-$C(O)OR_3$, $C_1$-$C_6$ alkoxy, and mono- to per-halo $C_1$-$C_6$ alkyl; and Base is selected from

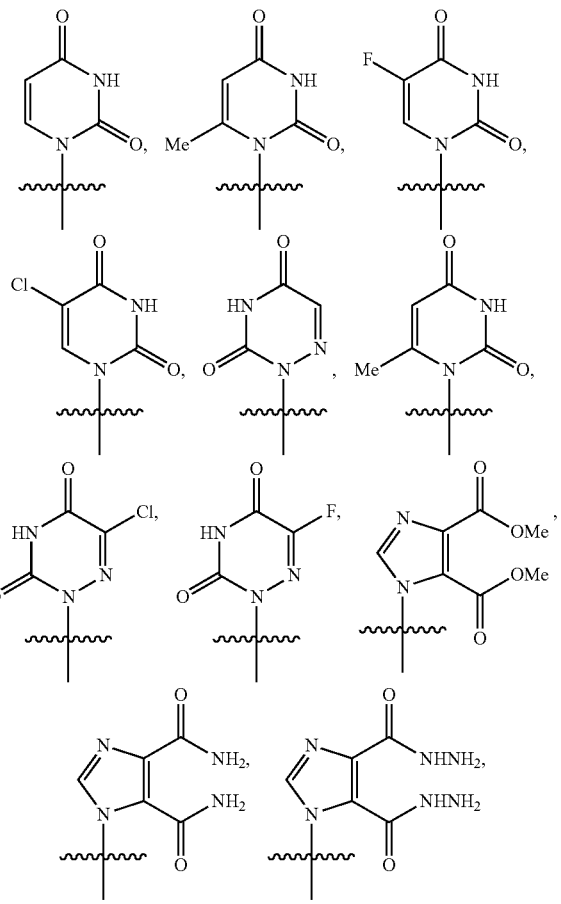

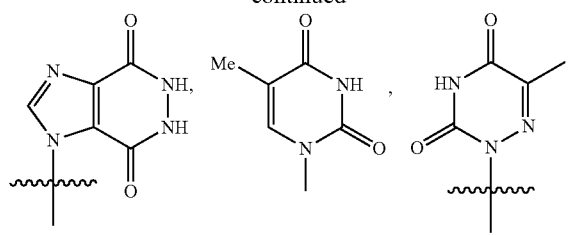

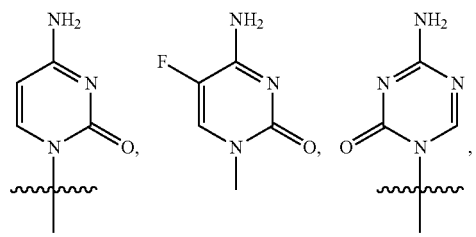

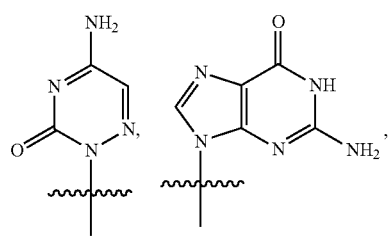

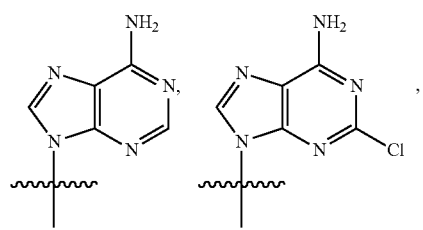

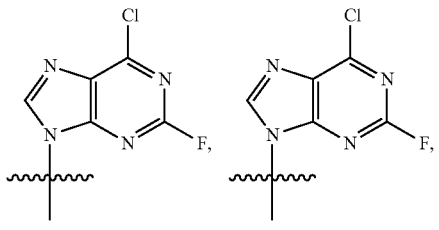

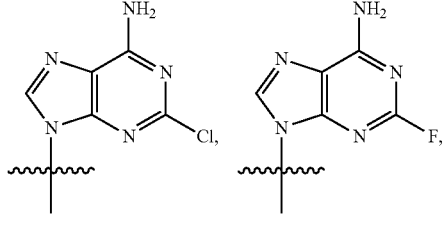

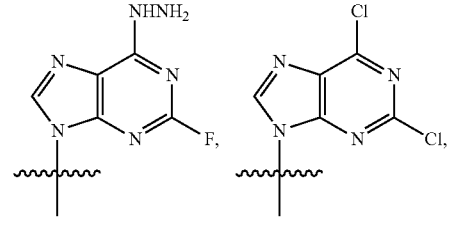

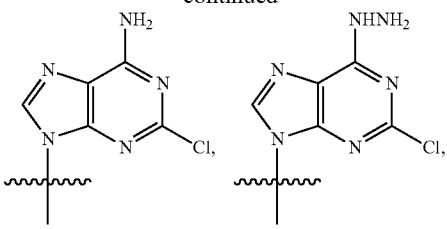

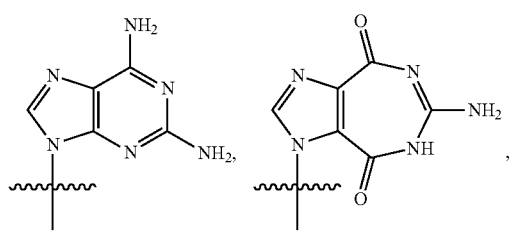

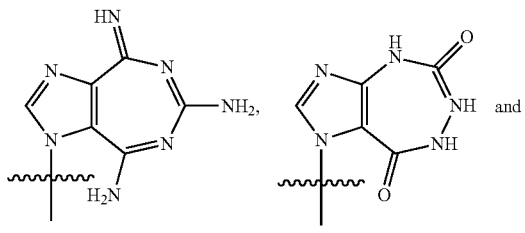

and

5. The compound of claim 4, wherein:

A and B are
independently —CH$_3$, —CH(CH$_3$)$_2$, —CF$_3$, —(CH$_2$)$_n$—CF$_3$, —(CH$_2$)$_n$-tetrazole, —(CH$_2$)$_n$-phenyl wherein the phenyl is optionally substituted with one or more groups selected from C$_1$-C$_3$ alkyl, —C$_1$-C$_3$ alkyl-C(O)OR$_3$, C$_1$-C$_3$ alkoxy, and mono- to perhalo C$_1$-C$_3$ alkyl;

R$_1$ is —CF$_3$, —CH$_2$-phenyl, phenyl optionally substituted with
halo, —CN, —CF$_3$, —C(O)OR$_3$, —CH$_2$—COOR$_3$, C$_1$-C$_3$ alkoxy, C$_1$-C$_4$ perfluoroalkyl, or C$_1$-C$_3$ alkyl, R$_2$ is phenyl or —CH$_2$-phenyl;

R$_3$ is —CF$_3$, phenyl optionally substituted with halo, —CN, —CF$_3$, —C(O)OR$_2$, —CH$_2$—COOR$_2$, C$_1$-C$_3$ alkoxy, C$_1$-C$_4$ perfluoroalkyl, or C$_1$-C$_3$ alkyl;

R$_4$ and R$_{4a}$ together with the nitrogen to which they are attached form -(AA)$_{1-4}$, -(AA)$_3$, or -Arg-Arg-Arg;

R$_5$ and R$_{5a}$ are independently —CH$_2$-phenyl or phenyl;

R$_6$ and R$_{6a}$ are —CH$_2$-phenyl or phenyl;

R$_7$ is 4-methylphenyl, phenyl or —CF$_3$;

and

Base is selected from:
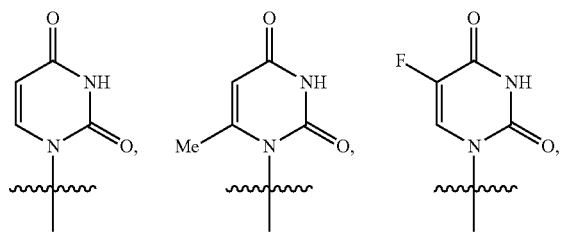
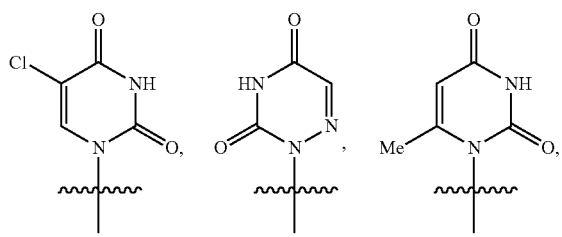
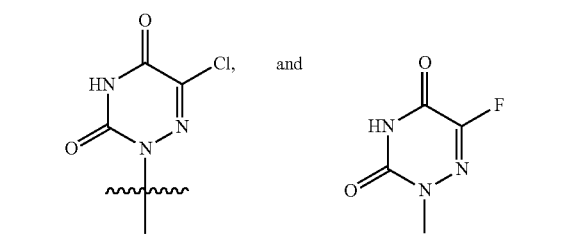
or selected from:
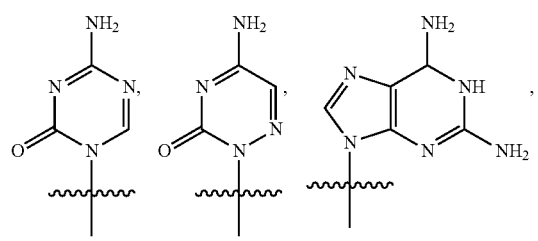
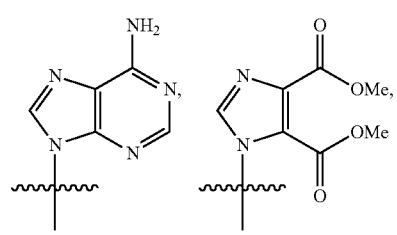
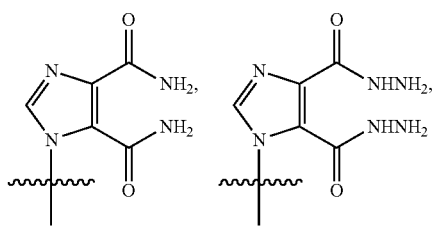
-continued
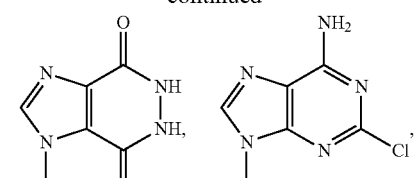
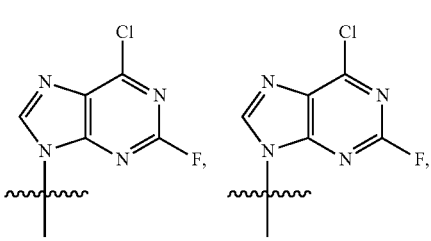
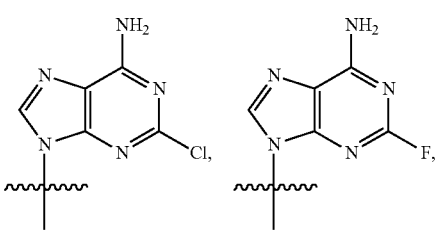
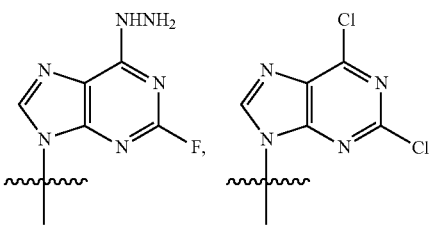
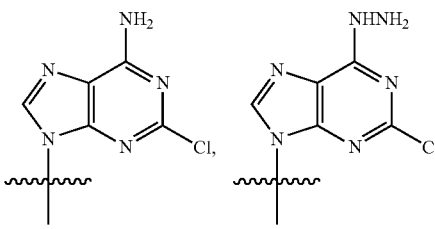
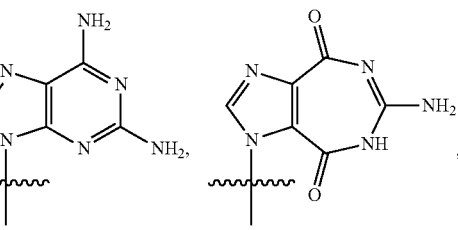
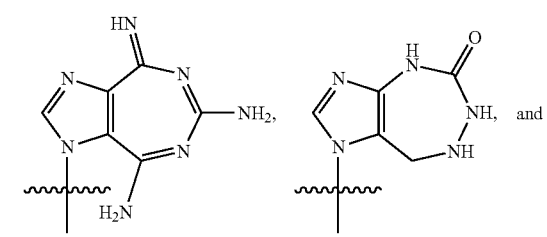
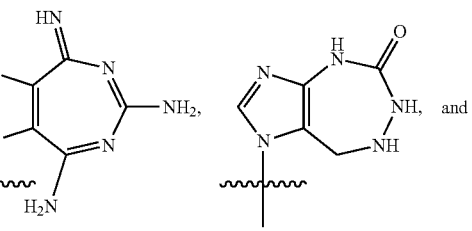

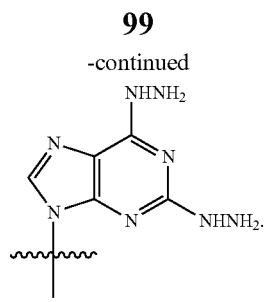
6. The compound according to claim 1, of the formula,
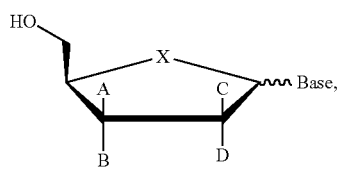
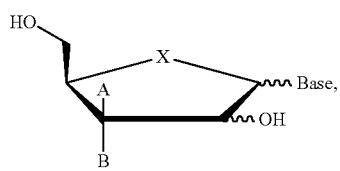
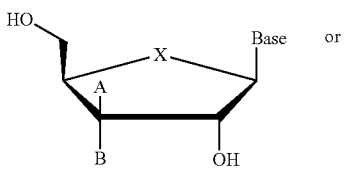
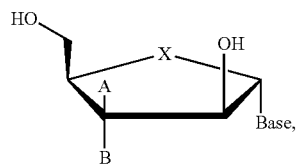
wherein
X is O or S;
one of A and B is $C_1$-$C_6$ alkyl;
the other of A and B is $CONH_2$, $CONR_6R_{6a}$, $CONHNH_2$, $CONHNHR_6$, —C(O)—$NR_4R_{4a}$, —C(O)$OR_2$, $(CH_2)n_1$C(O)$OR_2$, —C(O)—$R_3$, or —$(CH_2)_n$M;
C and D are independently —H, halo, azido, or —OH;
and Base is selected from the group consisting of
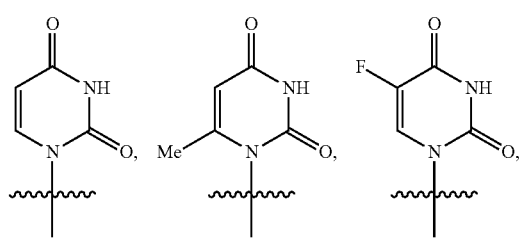
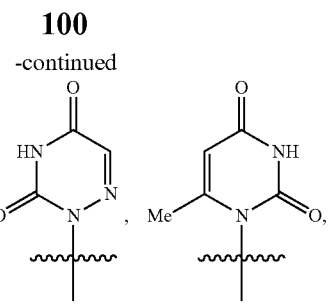
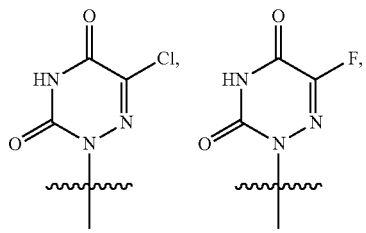
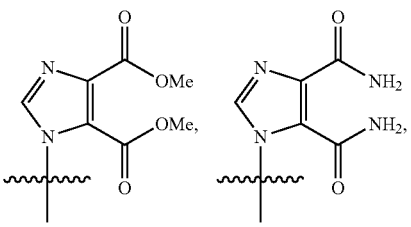
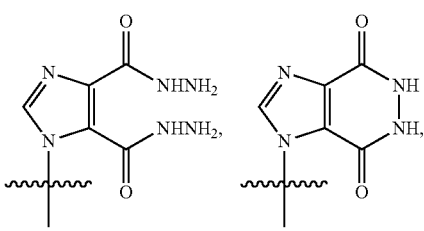
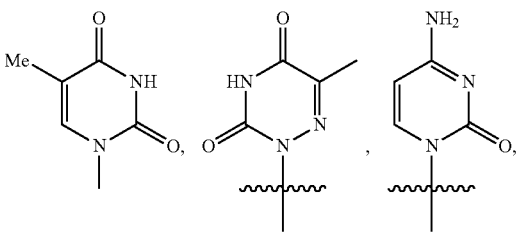
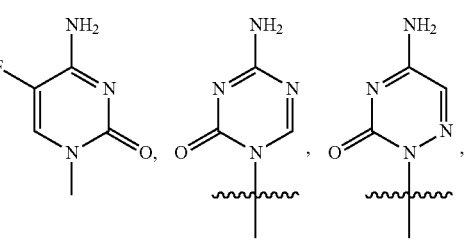
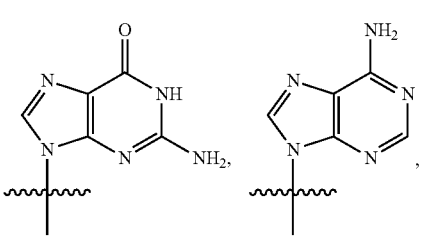

-continued
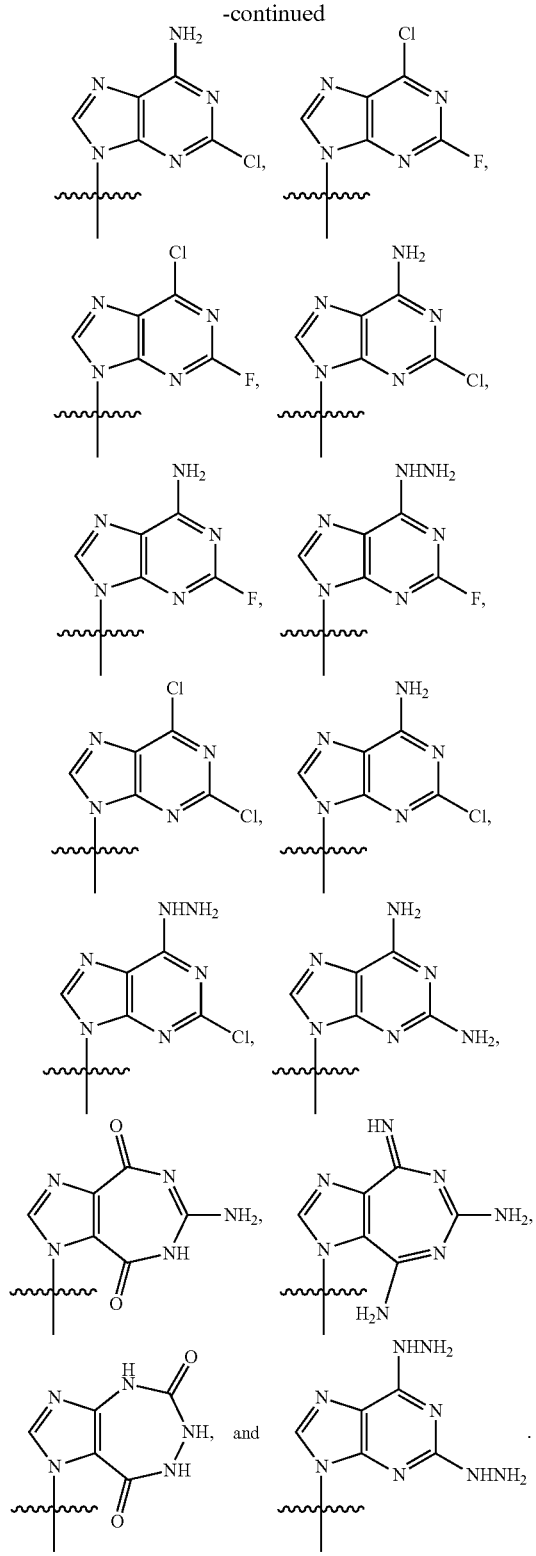
7. The compound according to claim 6, wherein:
M is —OR$_1$, —SR$_1$, —CO$_2$R$_2$, —COR$_3$, —NH(CO)R$_5$, —NR$_6$R$_{6a}$, —CONR$_4$R$_{4a}$, —NHSO$_2$R$_7$, —CO—CH$_2$OH, —SOR$_8$, —SO$_2$NR$_5$R$_{5a}$, —O(CO)R$_3$, or —N$_3$;
one of A and B is methyl, and the other of A and B is CONH$_2$, CONR$_6$R$_{6a}$, CONHNH$_2$, CONHNHR$_6$,
—C(O)—NR$_4$R$_{4a}$, —C(O)OR$_2$, (CH$_2$)n$_1$C(O)OR$_2$, —C(O)—R$_3$, or —(CH$_2$)$_n$M;
X is O;
and
Base is selected from:
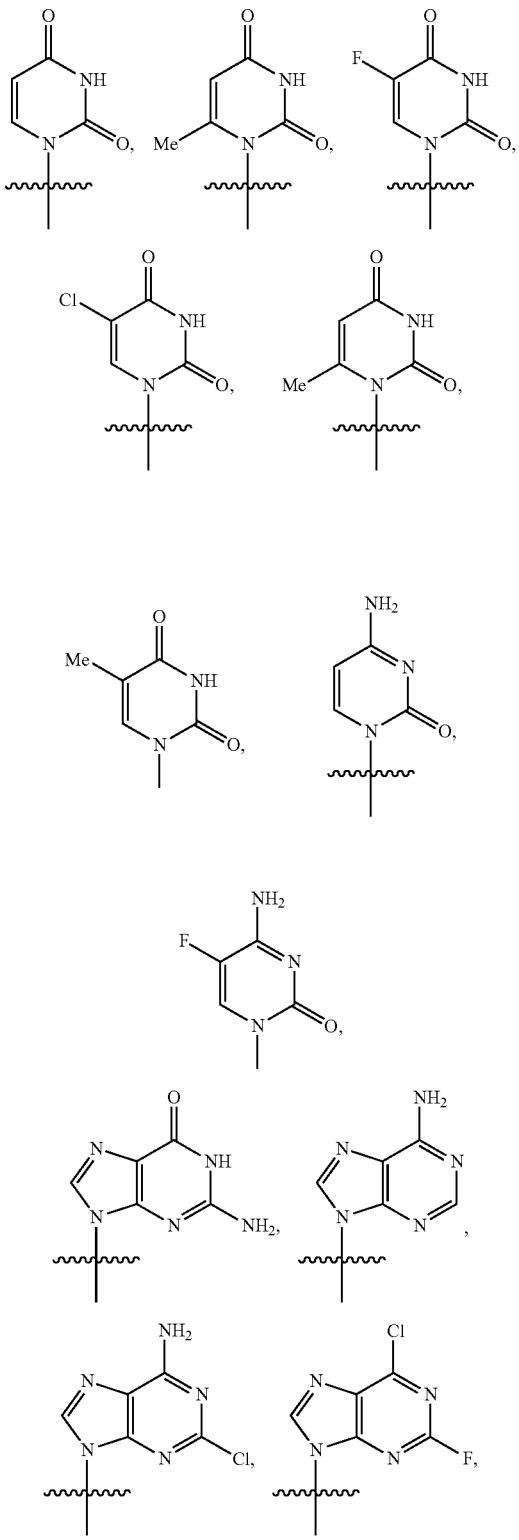

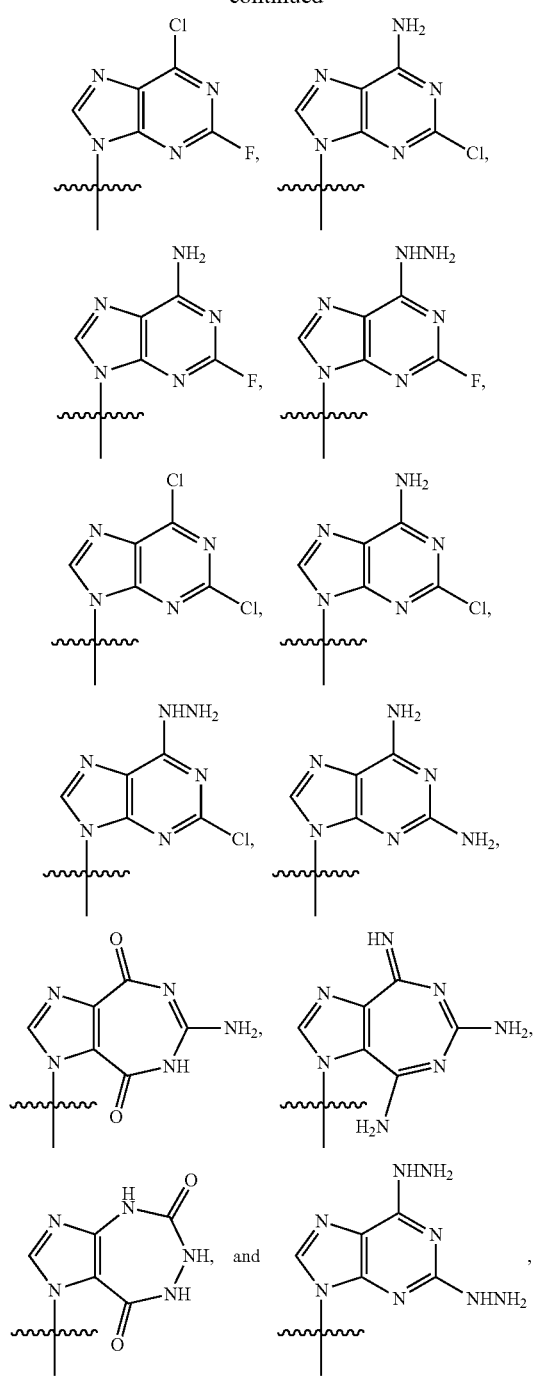
or selected from:
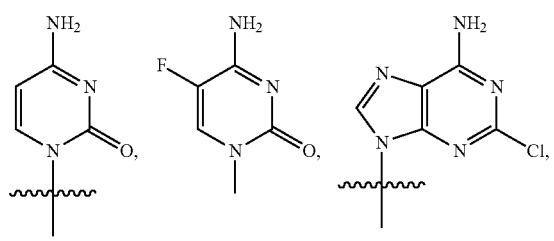
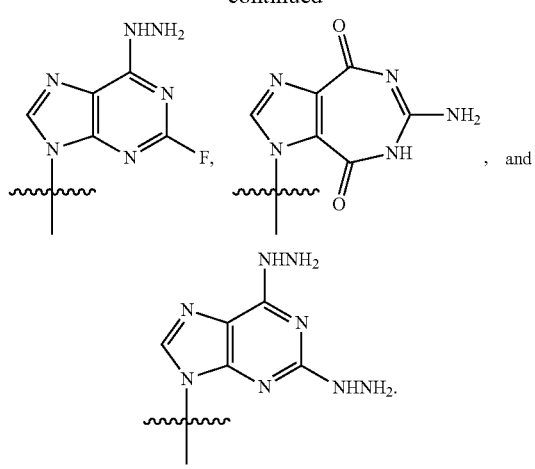
8. The compound according to claim 1 of the formula,
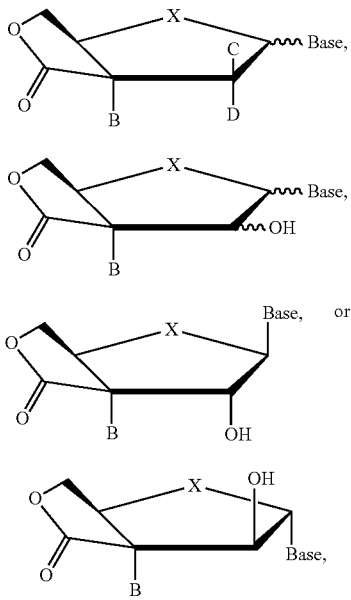
wherein
X is O or S;
B is $C_1$-$C_6$ alkyl, $C_2$-$C_6$ alkenyl, $C_2$-$C_6$ alkynyl, or mono- to per-halo $C_1$-$C_6$ alkyl;
C and D are independently —H, halo, azido, or —OH;
and Base is selected from the group consisting of
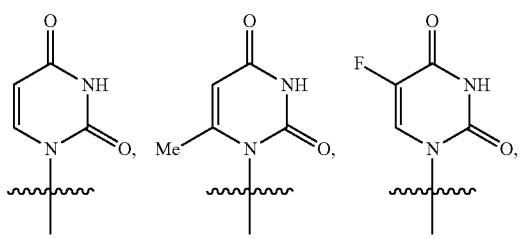

-continued
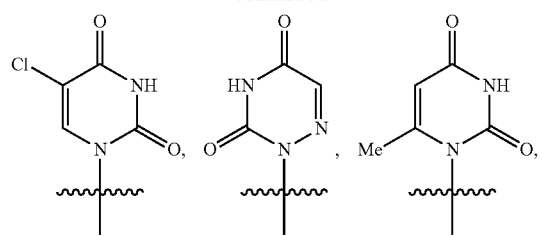
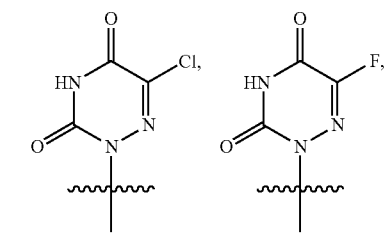
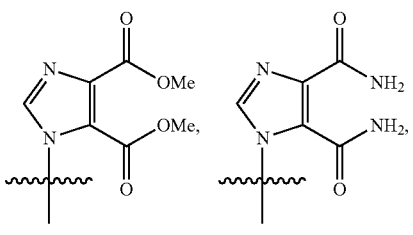
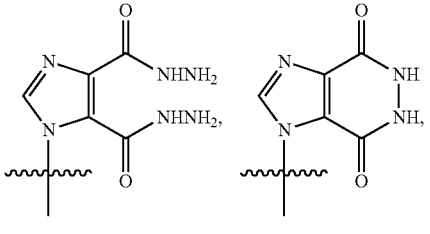
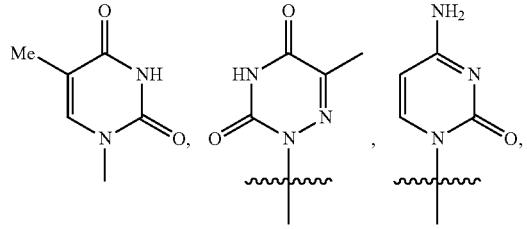
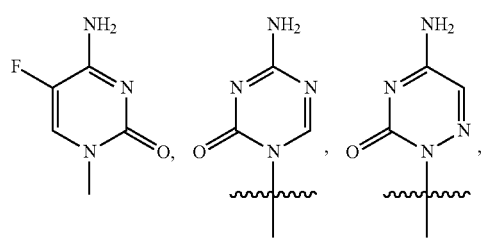
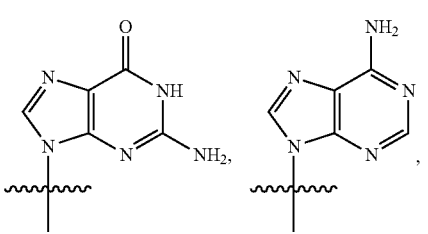
-continued
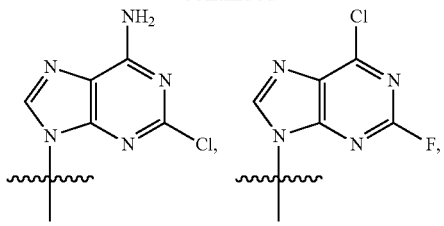
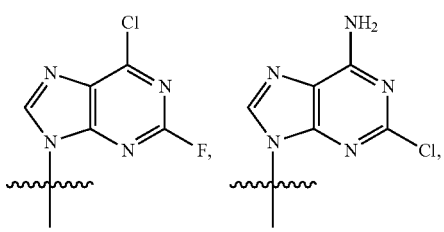
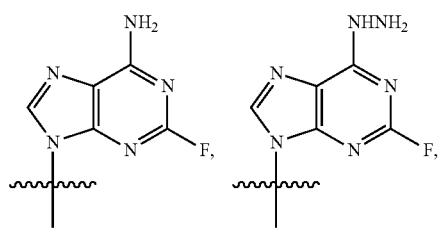
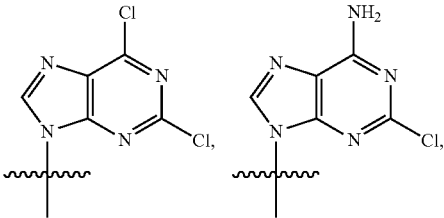
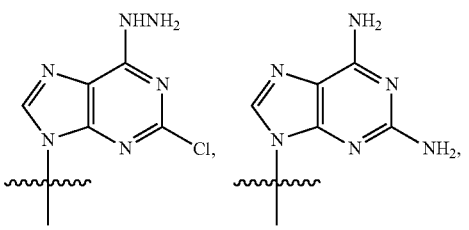
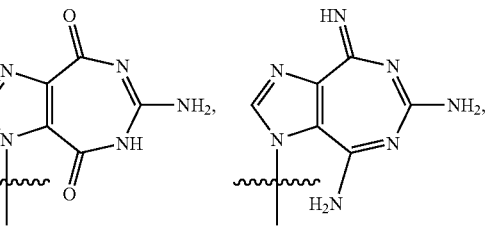
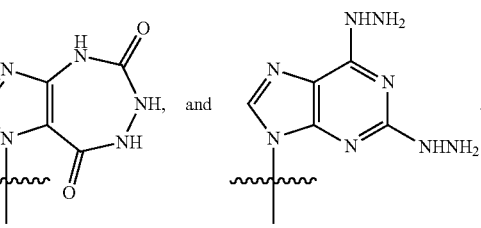
9. The compound of claim 8, wherein:
X is O;

Base is selected from:
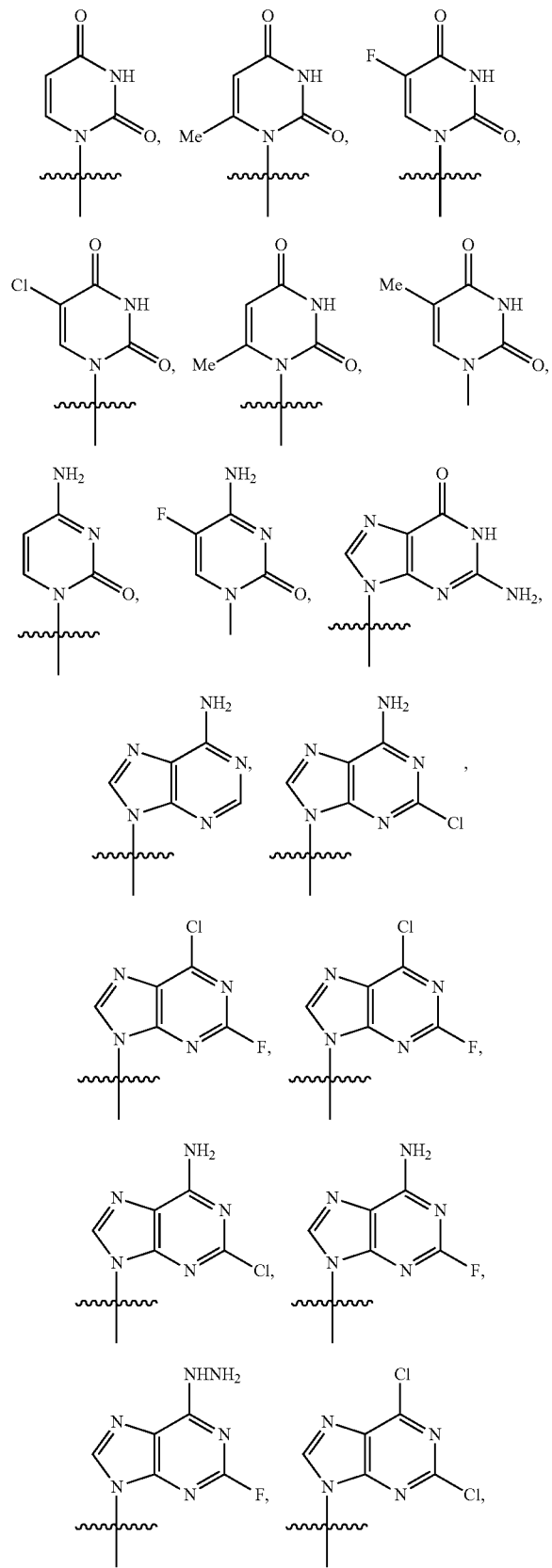
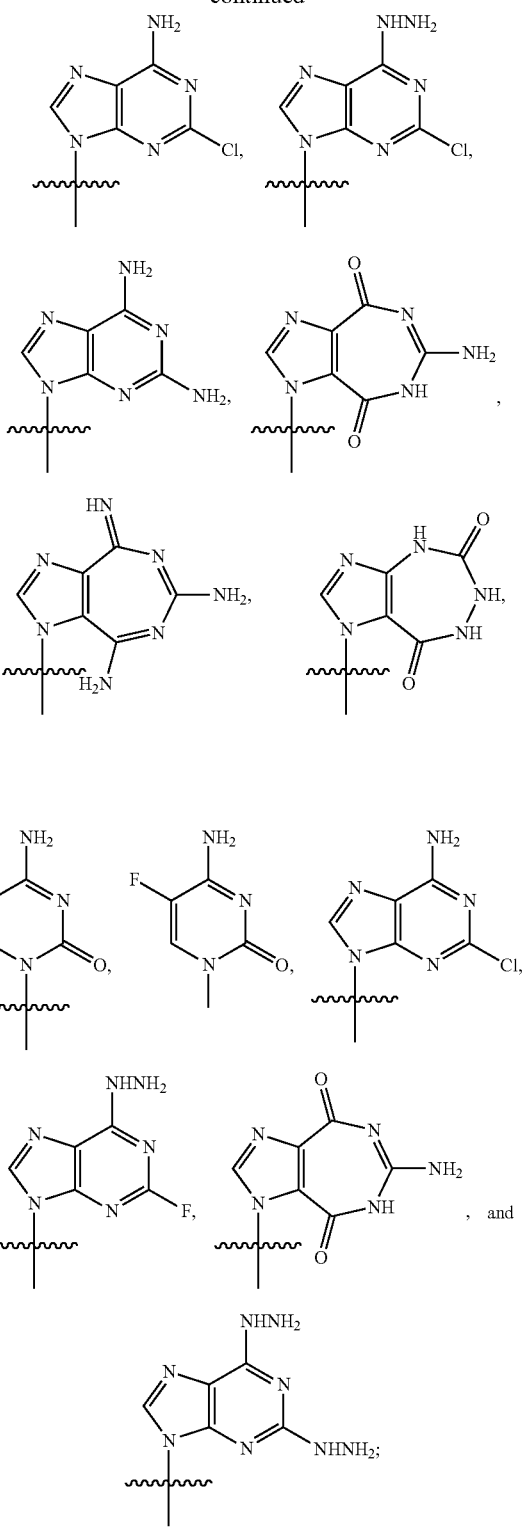
and
B is $C_1$-$C_6$ alkyl.
10. A pharmaceutical composition comprising a pharmaceutically acceptable carrier, excipient, or diluent and a compound according to claim 1 or a pharmaceutically acceptable salt thereof.

11. A compound of the formula

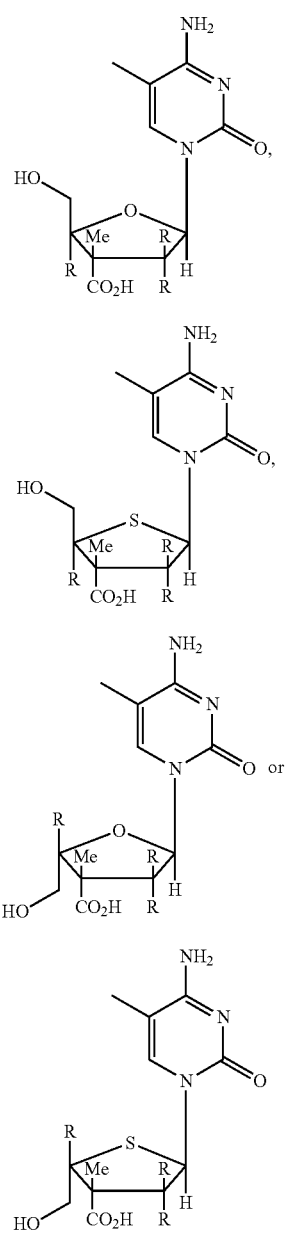

or a pharmaceutically acceptable salts thereof, wherein R is —H or —OH, with the proviso that at least one of the geminal R groups is —H.

12. A pharmaceutical composition comprising a pharmaceutically acceptable carrier, excipient, or diluent and a compound according to claim 11 or a pharmaceutically acceptable salts thereof.

13. A method for treating a disease or a condition in a patient in need thereof comprising administering an effective amount of a compound according to claim 1 wherein the disease or condition is ovarian cancer, cervical cancer, breast cancer, skin cancer, brain cancer, colorectal cancer, lung cancer, bone cancer, or glioblastoma.

14. A method for treating a disease or a condition in a patient in need thereof wherein the disease or condition is ovarian cancer, cervical cancer, breast cancer, skin cancer, brain cancer, colorectal cancer, lung cancer, bone cancer, or glioblastoma, comprising administering an effective amount of a compound of the formula:

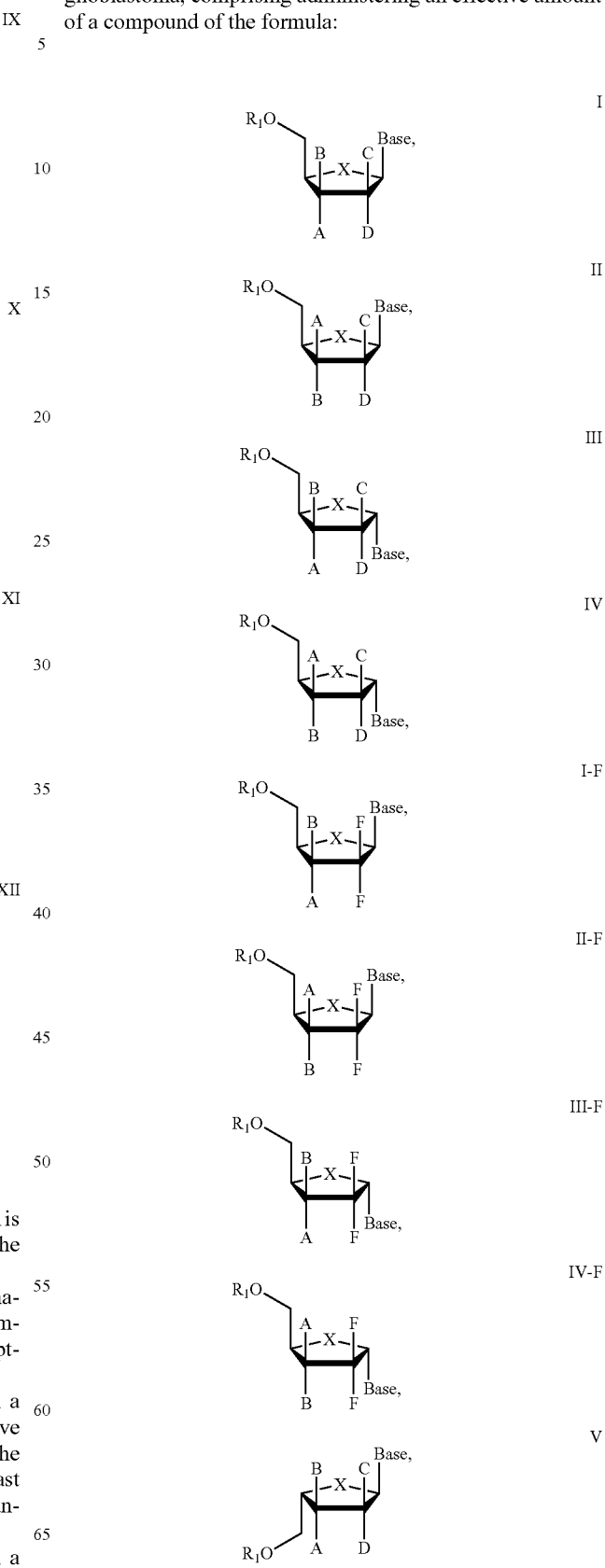

-continued
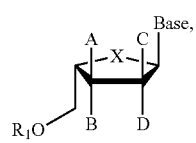
VI
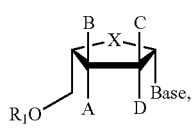
VII
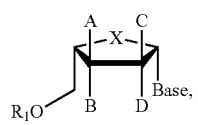
VIII
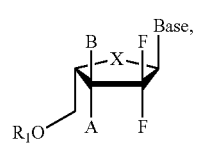
V-F
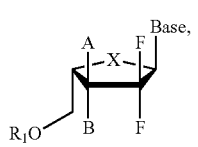
VI-F
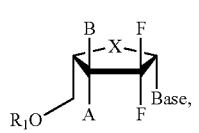
VII-F
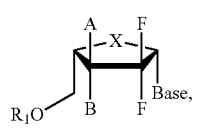
VIII-F
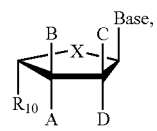
IX
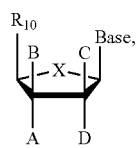
X
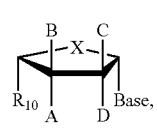
XI
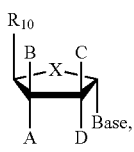
XII
-continued
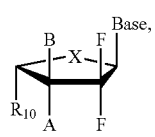
IX-F
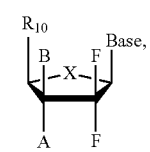
X-F
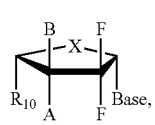
XI-F
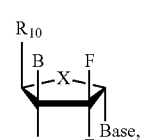
XII-F
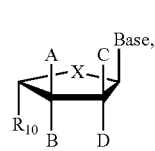
XIII
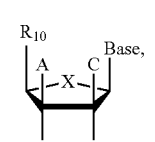
XIV
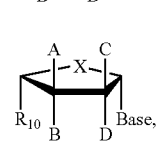
XV
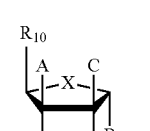
XVI
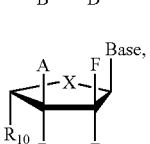
XIII-F
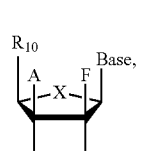
XIV-F
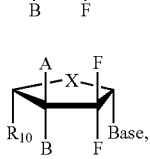
XV-F

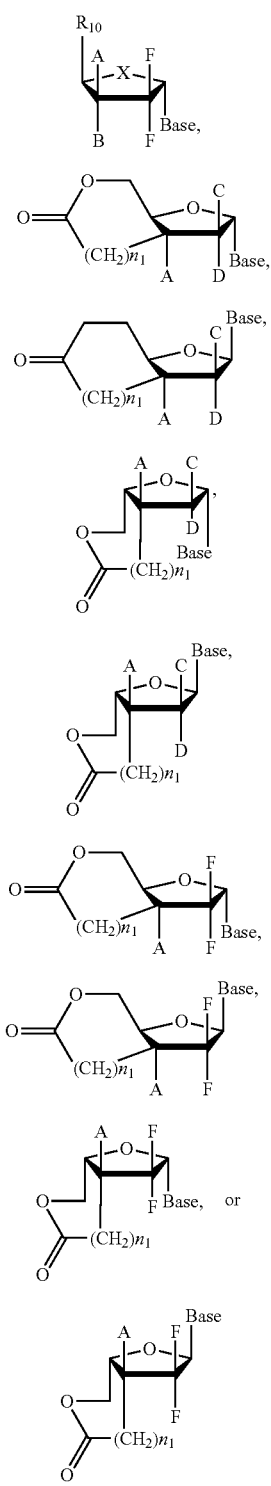

or a pharmaceutically acceptable salt thereof, wherein
A and B are independently $C_1$-$C_6$ alkyl, $C_2$-$C_6$ alkenyl, $C_2$-$C_6$ alkynyl, mono- to per-halo $C_1$-$C_6$ alkyl, —$CONH_2$, —$CONR_6R_{6a}$, —$CONHNH_2$, —$CONHNHR_6$, —C(O)-$NR_4R_{4a}$, —C(O)$OR_2$, —$(CH_2)n_1C(O)OR_2$, —C(O)-$R_3$, or -$(CH_2)_nM$;

M is —$OR$, halo, mono- to per-halo $C_1$-$C_6$ alkyl, -$SR_1$, aryl, —$CO_2R_2$, —$COR_3$, heterocyclyl, heteroaryl, —NH(CO)$R_5$, —$NR_6R_{6a}$, —$CONR_4R_{4a}$, —$NHSO_2R_7$, —CO—$CH_2OH$, —$SOR_8$, —$SO_2NR_5R_{5a}$, —O(CO)$R_3$, —$N_3$, or $C_2$-$C_6$ alkynyl, wherein each of the alkyl, heterocyclyl, aryl, and heteroaryl is optionally substituted with one or more groups selected from $C_1$-$C_6$ alkyl, halo, —CN, —C(O)$OR_3$, —$C_1$-$C_6$ alklyl—C(O)$OR_3$, $C_1$-$C_6$ alkoxy, and mono- to per-halo $C_1$-$C_6$ alkyl;

n is 1 to 3;

$n_1$ is 0 to 3;

$R_1$ is —H, —$CH_2$-P(O)(OH)$_2$, —P(O)(OH)$_2$, —P(O)(OR$_2$)$_2$, $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

$R_2$ is —H, aryl, —$C_1$-$C_6$ alkylaryl, or $C_1$-$C_6$ alkyl;

$R_3$ is —H C1-C6 alkyl, —$(CH_2)_mC(O)OR_2$ wherein m is 0 to 4, mono- to per-halo $C_1$-$C_6$ alkyl, aryl, or -$C_1$-$C_6$ alkylaryl, wherein each of the alkyl and aryl is optionally substituted with one or more groups selected from $C_1$-$C_6$ alkyl, halo, —CN, —C(O)$OR_2$, —$C_1$-$C_6$ alkyl-C(O)$OR_2$, $C_1$-$C_6$ alkoxy, and mono- to per-halo $C_1$-$C_6$ alkyl;

$R_4$ and $R_{4a}$ are independently —H, $C_1$-$C_6$ alkyl, —$(CH_2)_mC(O)OR_2$ wherein m is 0 to 4, mono- to per-halo $C_1$-$C_6$ alkyl, aryl, or —$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl; or $R_4$ and $R_{4a}$ together with the nitrogen to which the are attached form -$(AA)_x$ wherein x is 1 to 5, and AA is a natural, non-natural, D- or L- amino acid, wherein -$(AA)_x$ is terminated by a protected or unprotected carboxyl group;

$R_5$ and $R_{5a}$ are independently —H, aryl, $C_1$-$C_6$ alkylaryl, $C_1$-$C_6$ alkyl, or $C_1$-$C_6$ alkoxy;

$R_6$ and $R_{6a}$ are independently —H, aryl, $C_1$-$C_6$ alkylaryl, or $C_1$-$C_6$ alkyl;

$R_7$ is $C_1$-$C_6$ alkyl, aryl, $C_1$-$C_6$ alkylaryl, or mono- to per-halo $C_1$-$C_6$ alkyl;

$R_8$ is $C_1$-$C_6$ alkyl, aryl, $C_1$-$C_6$ alkylaryl, or mono- to per-halo $C_1$-$C_6$ alkyl;

$R_9$ is H or $C_1$-$C_6$ alkyl;

C and D are independently —H, halo, azido, —$OR_2$, CN, $CF_3$, $(CH_2)nCO_2R_9$, C(O)$NR_4R_{4a}$, or —$CONR_6R_{6a}$, with the proviso that C and D cannot simultaneously be —OH;

X is O or S;

$R_{10}$ is —C(O)$OR_3$, —$CH_2$-C(O)$OR_3$, —$CONH_2$, —$CONHR_6$, —$CONHNH_7$, —$CONHNHR_6$, —$CONR_4R_{4a}$, —$CONR_6R_{6a}$, —$CH_2$-P(O)(OH)$_2$, —P(O)(OH)$_2$, $C_1$-$C_6$ alkyl, aryl, or -$C_1$-$C_6$ alkylaryl, wherein each of the alkyl and aryl is optionally substituted with one or more groups selected from $C_1$-$C_6$ alkyl, halo, —CN, —C(O)$OR_3$, —$C_1$-$C_6$ alkyl-C(O)$OR_3$, $C_1$-$C_6$ alkoxy, and mono- to per-halo $C_1$-$C_6$ alkyl;

and Base is a purine derivative or a pyrimidine derivative.

* * * * *